United States Patent
Grunwald et al.

(10) Patent No.: US 7,022,075 B2
(45) Date of Patent: Apr. 4, 2006

(54) USER INTERFACE FOR HANDHELD IMAGING DEVICES

(75) Inventors: Sorin Grunwald, Palo Alto, CA (US); Robert Stanson, LaSalle (CA); Soo Hom, Milpitas, CA (US); Ailya Batool, Santa Clara, CA (US); Glen W. McLaughlin, Saratoga, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 0 days.

(21) Appl. No.: 10/697,148

(22) Filed: Oct. 29, 2003

(65) Prior Publication Data

US 2004/0138569 A1    Jul. 15, 2004

Related U.S. Application Data

(63) Continuation of application No. 10/081,542, filed on Feb. 20, 2002, now abandoned, which is a continuation-in-part of application No. 09/860,209, filed on May 18, 2001, now Pat. No. 6,569,102, which is a continuation of application No. 09/378,175, filed on Aug. 20, 1999, now Pat. No. 6,251,073.

(51) Int. Cl.
    *A61B 8/14*     (2006.01)

(52) U.S. Cl. .................................................. 600/446

(58) Field of Classification Search ........ 600/437–472; 128/916; 367/7, 11, 130, 138; 382/128; 705/3
See application file for complete search history.

(56) References Cited

U.S. PATENT DOCUMENTS

| 4,564,019 A | 1/1986 | Miwa |
|---|---|---|
| 4,648,276 A | 3/1987 | Klepper et al. |
| 4,693,319 A | 9/1987 | Amemiya |
| 5,161,535 A * | 11/1992 | Short et al. ................. 600/437 |
| 5,295,485 A | 3/1994 | Shinomura et al. |
| 5,425,366 A | 6/1995 | Reinhardt et al. |
| 5,442,940 A | 8/1995 | Secker et al. |
| 5,476,010 A | 12/1995 | Fleming et al. |
| 5,483,963 A | 1/1996 | Butler et al. |
| 5,541,468 A | 7/1996 | Frey et al. |
| 5,559,301 A | 9/1996 | Bryan, Jr. et al. |
| 5,590,658 A | 1/1997 | Chiang et al. |
| 5,617,862 A | 4/1997 | Cole et al. |
| 5,621,903 A | 4/1997 | Luciw et al. |

(Continued)

OTHER PUBLICATIONS

K. Rigby, et al., "Realtime Adaptive Imaging," IEEE Ultrasonics Symposium, 1988, p. 1603-06.

(Continued)

*Primary Examiner*—Ali Imam
(74) *Attorney, Agent, or Firm*—Carr & Ferrell LLP

(57) ABSTRACT

A Graphical User Interface (GUI) for an ultrasound system. The ultrasound system has operational modes and the GUI has corresponding icons, tabs, and menu items image and information fields. The User Interface (UI) provides several types of graphical elements with intelligent behavior, such as being context sensitive and adaptive, called active objects, for example, tabs, menus, icons, windows of user interaction and data display and an alphanumeric keyboard. In addition the UI may also be voice activated. The UI further provides for a touchscreen for direct selection of displayed active objects. In an embodiment, the UI is for a medical ultrasound handheld imaging instrument. The UI provides a limited set of hard and soft keys with adaptive functionality that can be used with only one hand and potentially with only one thumb.

53 Claims, 36 Drawing Sheets

U.S. PATENT DOCUMENTS

| | | |
|---|---|---|
| 5,633,912 A | 5/1997 | Tsoi |
| 5,640,960 A | 6/1997 | Jones et al. |
| 5,694,562 A | 12/1997 | Fisher |
| 5,699,244 A | 12/1997 | Clark, Jr. et al. |
| 5,714,971 A | 2/1998 | Shalit et al. |
| 5,722,412 A | 3/1998 | Pflugrath et al. |
| 5,727,174 A | 3/1998 | Aparicio, IV et al. |
| 5,738,099 A | 4/1998 | Chang |
| 5,745,716 A | 4/1998 | Tchao et al. |
| 5,748,927 A | 5/1998 | Stein et al. |
| 5,749,072 A | 5/1998 | Mazurkiewicz et al. |
| 5,754,179 A | 5/1998 | Hocker et al. |
| 5,774,540 A | 6/1998 | Davidson et al. |
| 5,782,769 A | 7/1998 | Hwang et al. |
| 5,805,159 A | 9/1998 | Bertram et al. |
| 5,817,024 A | 10/1998 | Ogle et al. |
| 5,839,442 A | 11/1998 | Chiang et al. |
| 5,851,186 A | 12/1998 | Wood et al. |
| 5,873,830 A | 2/1999 | Hossack et al. |
| 5,901,246 A | 5/1999 | Hoffberg et al. |
| 5,919,138 A | 7/1999 | Ustuner |
| 5,923,325 A | 7/1999 | Barber et al. |
| 5,951,479 A | 9/1999 | Holm et al. |
| 5,964,709 A | 10/1999 | Chiang et al. |
| 5,997,478 A | 12/1999 | Jackson et al. |
| 6,055,439 A | 4/2000 | Helin et al. |
| 6,055,861 A | 5/2000 | Banata, Jr. et al. |
| 6,063,030 A | 5/2000 | Vara et al. |
| 6,117,079 A | 9/2000 | Brackett et al. |
| 6,126,608 A | 10/2000 | Kemme et al. |
| 6,135,960 A | 10/2000 | Holmberg |
| 6,141,011 A | 10/2000 | Bodnar et al. |
| 6,230,043 B1 | 5/2001 | Johnson |
| 6,251,073 B1 | 6/2001 | Imran et al. |
| 6,413,217 B1 | 7/2002 | Mo |
| D461,814 S | 8/2002 | Felix et al. |
| D462,446 S | 9/2002 | Felix et al. |
| D467,002 S | 12/2002 | Felix et al. |
| D469,539 S | 1/2003 | Felix et al. |
| 6,512,854 B1 * | 1/2003 | Mucci et al. ............ 382/275 |
| D469,877 S | 2/2003 | Felix et al. |
| 6,569,102 B1 | 5/2003 | Imran et al. |
| 6,674,879 B1 * | 1/2004 | Weisman et al. ........ 382/128 |
| 2001/0000668 A1 | 5/2001 | Bodnar |
| 2001/0000964 A1 | 5/2001 | Alexander |
| 2001/0004260 A1 | 6/2001 | Bauer et al. |
| 2002/0138002 A1 | 9/2002 | Tarakci et al. |
| 2002/0173721 A1 | 11/2002 | Grunwald et al. |
| 2002/0188199 A1 | 12/2002 | McLaughlin et al. |
| 2003/0013959 A1 | 1/2003 | Grunwald et al. |

OTHER PUBLICATIONS

A. Pesavento, et al., "Compression of Ultrasound RF Data," IEEE Proc. Ultrasonics Symposium, 1997.

Fabian, Christopher, et al., "Development of a Parallel Acquisition System for Ultrasound Research," Dept. of Electrical Eng., University of Virginia, 2001, pp. 1-9.

Fabian, Christopher, et al., "Development of a Parallel Acquisition System of Ultrasound Research," IEEE Proc. Ultrasonics Symposium, 2001.

* cited by examiner

USER INTERFACE FOR HANDHELD IMAGING DEVICES

CROSS REFERENCES TO RELATED APPLICATIONS

This application is a continuation application of U.S. patent application Ser. No. 10/081,542 filed Feb. 20, 2002 now abandoned and entitled "User Interface for Handheld Imaging Devices" which is a continuation-in-part application of U.S. patent application Ser. No. 09/860,209 filed May 18, 2001, now U.S. Pat. No. 6,569,102, and entitled "Miniaturized Ultrasound Apparatus and Method" which is a continuation of U.S. patent application Ser. No. 09/378,175 filed Aug. 20, 1999, now U.S. Pat. No. 6,251,073, and entitled "Miniaturized Ultrasound Apparatus and Method."

This application is related to U.S. patent application Ser. No. 09/872,541 filed May 31, 2001 and entitled "System and Method for Phase Inversion Ultrasonic Imaging"; U.S. patent application Ser. No. 10/039,910 filed Oct. 20, 2001 and entitled "System and Method for Coupling Ultrasound Generating Elements to Circuitry"; U.S. patent application Ser. No. 29/147,576 filed Aug. 31, 2001, now design patent number D469,539 and entitled "Handheld Ultrasonic Display Device"; U.S. patent application Ser. No. 29/147,660 filed Aug. 31, 2001, now U.S. design patent number D469,877 and entitled "Handheld Ultrasonic Display Device with Cover"; U.S. patent application Ser. No. 29/148,421 filed Sep. 19, 2001, now U.S. design patent number D467,002 and entitled "Handheld Ultrasonic Transducer with Curved Bulb Grip"; U.S. patent application Ser. No. 29/148,532 filed Sep. 19, 2001, now U.S. design patent number D462,446 and entitled "Handheld Ultrasonic Transducer with Bulb Grip"; U.S. patent application Ser. No. 29/149,730 filed Oct. 15, 2001, now U.S. design patent number D461,814 and entitled "Docking Station."

All of the aforementioned applications are assigned to the same assignee and are incorporated herein by reference.

BACKGROUND OF THE INVENTION

1. Field of the Invention

The present invention relates to user interfaces in general and more specifically to a user interface for an ultrasound imaging device and to a handheld ultrasound imaging device.

2. Description of Prior Art

Ultrasonic imaging is a frequently used method of analysis for examining a wide range of materials. Ultrasonic imaging is especially common in medicine because of its relatively non-invasive nature, low cost and fast response times. Typically, ultrasonic imaging is accomplished by generating and directing ultrasonic sound waves (an ultrasonic beam or signal) into a medium under investigation using a set of ultrasound generating transducers and then observing reflections generated at the boundaries of dissimilar materials, such as tissues within a patient, also using a set of ultrasound receiving transducers. A single transducer, however, may be used rather than an array of transducers. The receiving and generating transducers may be arranged in arrays and the same transducer may be used for both receiving and generating ultrasonic signals. The reflections are converted to electrical signals by the receiving transducers and then processed, using techniques known in the art, to determine the locations of echo sources. The resulting data is displayed using a display device, such as a monitor.

Typically, the ultrasonic signal transmitted into the medium under investigation is generated by applying continuous or pulsed electronic signals to an ultrasound generating transducer. The transmitted ultrasonic signal is most commonly in the range of 40 kHz to 30 MHz. The ultrasonic signal propagates through the medium under investigation and reflects off interfaces, such as boundaries, between adjacent tissue layers. Scattering of the ultrasonic signal is the deflection of the ultrasonic signal in random directions. Attenuation of the ultrasonic signal occurs when some of the ultrasonic signal is lost while the signal travels. Reflection of the ultrasonic signal is the bouncing off of the ultrasonic signal from an object and changing its direction of travel. Transmission of the ultrasonic signal is the passing of the ultrasonic signal through a medium. As it travels, the ultrasonic signal is scattered, attenuated, reflected, and/or transmitted. The portions of the reflected ultrasonic signals that return to the transducers are detected as echoes. The detecting transducers convert the echo signals into electronic signals and, after amplification and digitization, furnish these ultrasonic signals to a beam former. The beam former calculates locations of echo sources and typically includes simple filters and signal averagers. After beam forming, the calculated positional information is used to generate two-dimensional data that can be presented as an image.

As an ultrasonic signal propagates through a medium under investigation, additional harmonic frequency components are generated. These components are analyzed and associated with the visualization of boundaries or image contrast agents designed to re-radiate ultrasonic signals at specific harmonic frequencies. Unwanted reflections within the ultrasound device can cause noise and the appearance of artifacts (i.e., image features that result from the imaging system and not from the medium under investigation) in the image. Artifacts may obscure the underlying image of the medium under investigation.

The ultrasonic signal intensity as a function of position may oscillate rather than fall off monotonically as a function of distance from the center of the beam that forms the ultrasonic signal. These oscillations in ultrasonic signal intensity are often called "side lobes." In the prior art, the term "apodisation" refers to the process of affecting the distribution of ultrasonic signal intensity to reduce side lobes. In the remainder of this specification, however, the term "apodisation" is used to refer to tailoring the distribution of ultrasonic signal intensity for a desired beam characteristic such as having a Guassian or sinc function (without the side lobes) distribution of ultrasonic signal intensity.

Steering refers to changing the direction of an ultrasonic signal. Aperture refers to the size of the transducer or group of transducers being used to transmit or receive an ultrasonic signal.

The prior art process of producing, receiving and analyzing an ultrasonic signal (or beam) is called beam forming. The production of ultrasonic signals optionally includes apodisation, steering, focusing and aperture control. Using a prior art data analysis technique, each ultrasonic signal is used to generate a one-dimensional set of echolocation data. In a typical implementation, a plurality of ultrasonic beams is used to scan a multi-dimensional volume. Imaging, in general, and ultrasound imaging, in particular, are utilized in many medical procedures in order to detect a patient's condition. For example, ultrasonic imaging is commonly used to detect and monitor the growth and health of fetuses or to detect and assist in the diagnosis of liver and kidney pathology.

Many medical ultrasound imaging systems have been designed, manufactured and successfully used, each varying in presentation, complexity, and ergonomics. In some cases, the user interfaces are cumbersome to operate. Even more cumbersome are those user interfaces requiring two hands to operate or transport resulting in encumbrance of using the system for real-time examinations. Other examples of difficulties that arise in the case of a handheld device are navigation and selection of the user interface items using one hand or one thumb. It may be desirable, in handheld ultrasound devices, the user interface allow for quick and efficient interaction supported by intelligent user interface behavior, context sensitivity, data dependent optimization and the ability to self-adapt to user behavior.

Further, as medical services tend to be expensive, the easier a medical professional can operate the user interface, the more patients the medical professional can serve and the less the medical professional will need to charge for their services.

SUMMARY OF THE INVENTION

The present user interface may include an intelligent and/or dynamic graphical user interface together with a set of tactile controls. The user interface provides several types of graphical elements with intelligent behavior. For example, the graphical element may be a context sensitive and adaptive element such as an active object. Active objects of the present user interface may be tabs, menus, icons, windows for user interaction and data display and/or an alphanumeric keyboard, for example. In addition the user interface may be voice activated. The user interface may include a touch screen for direct selection of displayed active objects. In an embodiment, the functions of the ultrasound system are organized into operational modes that allow for a menu structure that is intuitive to the user so that the user spends less time looking for features and more time using the ultrasound system in comparison to a menu structure that is not intuitive to the user.

In an embodiment, the ultrasound system is a handheld device. A limited set of hard and soft keys with adaptive functionality allow for one hand, and potentially one thumb operation. Elements are considered "active" when they have their own information processing capabilities, for example, each icon, tab or selection may have a response that is a function of input, context, and/or history. Elements are considered "intelligent" when the interactions between elements, the user, and the device are auto-adaptive (i.e., auto-adaptive interactions are automatically optimized depending on a number of parameters, including system state, and/or user habits, for example). In order to accommodate holding and controlling the device at the same time with one hand, the user interface maybe designed for one-hand, one-thumb operation and makes use of several intelligent (adaptive and context sensitive) and/or active elements (e.g., windows, soft buttons, tabs, menus, toolbars, and icons). For example, the buttons may be placed on the handle of the handheld ultrasound system so they can be operated using the thumb of the hand holding the display portion of the handheld ultrasound system. The number and functions of the buttons indicated in this invention are for exemplification purposes and shall not constitute a limitation of the invention. Some buttons have fixed functionality (hard buttons); i.e., they always activate the same system function independent of the operation mode such as a button for freezing and unfreezing an image or a button for automatically optimizing display parameters. In an embodiment, other buttons are used to position a cursor on the graphical user interface up, down, left, and right. A select button may be used to activate an object to which a cursor is pointing to or to perform a certain system function in accordance with the cursor's position. In an embodiment, one or more buttons may switch functionality depending on the system state of ultrasound system and/or may be programmable, such as a print/save and/or a back/escape button. In an embodiment the buttons may be placed on a handle of a display screen so that they can be activated while holding the display screen. The buttons may be designed for use with a specific finger (e.g., the thumb) or with a specific set of fingers. The buttons should not be significantly smaller than the width of the finger (e.g., the thumb) for which they are designed to be used. The buttons should also not be too much wider than the intended finger or fingers for which they are designed so as not to unduly limit number of buttons on the handle. For example, the buttons may be 0.25 to 2.5 cm wide. The buttons may be arranged in a circular or elliptical pattern so that they are easily accessible. In an embodiment buttons may have the functions that are most frequently used.

The imaging device of the invention may provide for a microphone (and/or an input for an external microphone) and a loudspeaker (and/or an output for external loudspeakers). The user can train the device to recognize a set of words or combinations of words. Each recognizable unit (word or word combination) can be assigned to a device command, performing a specific function or a sequence of functions, so that the user has the option of operating part of or all of the ultrasound system by voice, thereby requiring less use of hands to operate.

In an embodiment, an auto-optimize button is provided. Whenever the user presses this button, the system settings are automatically optimized in accordance with several parameters including the system state, the image content, and the type of application.

In an embodiment, the screen of the ultrasound device may be shared by several elements each of which may be active and/or intelligent, which may facilitate one-hand, one-thumb controlled imaging. For example, the tabs on the top left hand side of the screen representation can be selected by using the left/right buttons. The entries on one tab can be selected by using the up/down buttons. The icons on the toolbar on the bottom right-hand side of the screen can be selected by using the left/right buttons. A select/back button may be provided having multiple functions including that of the enter button on a keyboard. The image window is itself an active element. Changing input focus (i.e., the region sensitive to input) from the tab on the left hand side to the image on the right hand side can be achieved by using a combination of left/right or select/back buttons. All the text fields on the right hand side image window, e.g., the "Patient Name" or the "Date and Time" fields, are active elements. These active elements can be selected using the left/right or select/back buttons, for example, and once selected, show active and/or intelligent behavior. For example, selecting the "Date and Time" field may automatically fill the "Date and Time" field with the date and time. Similarly, selecting the "Patient Name" can open the database interface and retrieve the corresponding patient record.

In an embodiment, one-handed, potentially one-thumb alphanumeric data entry (e.g., patient name and/or other patient information) may be achieved by displaying a "virtual" keyboard. The user can select any alphanumeric key on the keyboard by using the left/right and up/down buttons. Using these buttons will have the same effect as depressing a keyboard key.

Other screens may also be configured to optimize one-hand and/or one-thumb operations. The database interface is configured such that database fields are selectable using the left/right and up/down buttons. The file navigation interface has a hierarchical structure that provides for up/down navigation at the same level in the hierarchy and left/right navigation to move between hierarchy levels. The same concept applies to all hierarchically structured active elements.

In order to support the user in learning and operating the system, context sensitive help is provided. This context sensitive help may relate to explaining the functional capabilities of the system or to the interpretation of image data, for example.

In an embodiment, the user interface provides for random access to any of the active elements through a touchscreen. In the one-handed embodiment, the user can utilize the thumb or any other finger to "touch" and activate any of the screen elements. In addition, a stylus, or another pointing device, can be used in a two-handed operation mode.

In an embodiment, in order to minimize the time for setting up and configuring the system the user interface may provide for application and/or user dependent presets, which are optimized based on several factors (e.g., user behavior, image quality, etc.). In an embodiment, several active elements are introduced in accordance with this invention in order to minimize user interaction for achieving predefined goals. For example, the icon "Full Screen Image" allows the user to directly switch to an imaging mode where the image occupies the full screen. The "Full Screen Image" display mode introduced in this invention is preferred because it shows the user a bigger image, where the details are easier to distinguish.

Regarding the ultrasound imaging system of the invention, broad beam technologies refer to systems and methods that include or take advantage of techniques for generating ultrasound and analyzing detected echoes. Broad beam technologies use multidimensional spatial information obtainable from a single ultrasonic pulse.

Area forming is the process of producing, receiving, and analyzing an ultrasonic beam, that optionally includes apodisation, steering, focusing, and aperture control, where a two-dimensional set of echolocation data can be generated using only one ultrasonic beam. Nonetheless, more than one ultrasonic beam may still be used with the area forming even though only one is necessary. Area forming is a process separate and distinct from beam forming. Area forming may yield an area of information one transmit and/or receive cycle, in contrast to beam forming that typically only processes a line of information per transmit and/or receive cycle. Alternatively, beam forming can be used instead of area forming electronics throughout this application.

Volume forming is the process of producing, receiving, and analyzing an ultrasonic beam, that optionally includes apodisation, steering, focusing, and aperture control, where a three dimensional set of echolocation data can be generated using only one ultrasonic beam. Nonetheless, multiple ultrasonic beams may be used although not necessary. Volume forming is a superset of area forming.

Multidimensional forming is the process of producing, receiving, and analyzing an ultrasonic beam that optionally includes apodisation, steering, focusing, and aperture control. Using multidimentional forming a two or more dimensional set of spatial echolocation data can be generated with only one ultrasonic beam. Nonetheless, multiple ultrasonic beams may be used although not necessary. Multidimensional forming optionally includes non-spatial dimensions such as time and velocity.

The Graphical User Interface (GUI) of the present invention can be used with a system that makes use of broad beam technologies.

DETAILED DESCRIPTION OF THE INVENTION

The following description focuses on the presently preferred embodiment of this invention, which is typically operative in end-user ultrasound medical imaging. The present invention, however, is not limited to any particular application or any particular environment. Instead, those skilled in the art will find that the system and methods of the present invention may be advantageously applied to a variety of systems such as portable systems that may include a mobile telephone, a Personal Digital Assistant (PDA), and/or a portable computer. Therefore, the description that follows of the exemplary embodiments is for purposes of illustration and not limitation.

In this specification the word "system" is to be understood as generic to including one element or device and to include multiple elements and/or devices. Also, in this specification the word "mode" is to be understood as generic to functions of, operations performed by, operations performed on, and/or settings of the entire ultrasound system or of any part of the ultrasound system.

Figure 1:
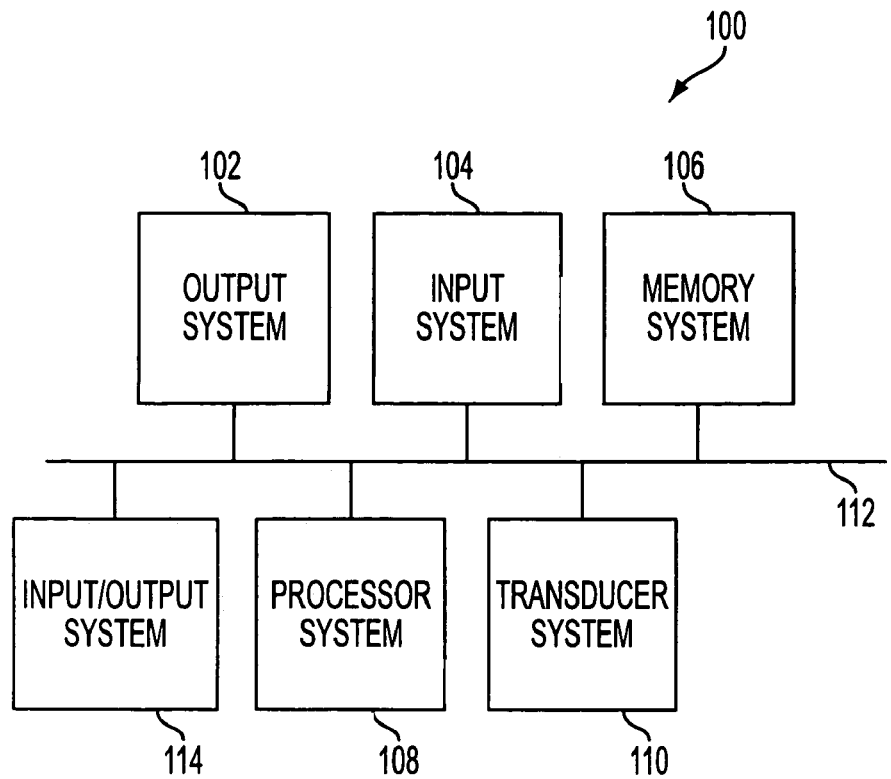
FIG. 1 shows a block diagram of an ultrasound system according to an embodiment of the invention.

FIG. 1 shows a block diagram of an ultrasound system 100 according to an embodiment of the invention including output system 102, input system 104, memory system 106, processor system 108, transducer system 110, communications system 112, and input/output device 114.

Output system 102 may include any one of, some of, any combination of, or all of a monitor system, a handheld display system, a printer system, a speaker system, a connection or interface system to a sound system, an interface system to peripheral devices (e.g., Infrared Data Association (IrDA) or Universal Serial Bus (USB)) and/or a connection and/or interface system to a computer system, intranet, and/or internet, or the like. Input system 104 may include any one of, some of, any combination of, or all of a keyboard system, a mouse system, a track ball system, a track pad system, buttons on a handheld system, a scanner system, a microphone system, a connection to a sound system, and/or a connection and/or interface system to a computer system, intranet, and/or internet (e.g., IrDA, USB) or the like. Memory system 106 may include, for example, any one of, some of, any combination of, or all of a long term storage system, such as a hard drive; a short term storage system, such as random access memory; a removable storage system, such as a floppy drive or a removable drive; and/or flash memory. Processor system 108 may include any one of, some of, any combination of, or all of multiple parallel processors, a single processor, a system of processors having one or more central processors and/or one or more specialized processors dedicated to specific tasks. Also, processor system 108 may include one or more Digital Signal Processors (DSPs) in addition to or in place of one or more Central Processing Units (CPUs) and/or may have one or more digital signal processing programs that run on one or more CPU. Transducer system 110 may include any one of, some of, any combination of, or all of one or more transducers, linear arrays of transducers, and/or two-dimensional arrays of transducers, for example. The elements of the transducer arrays may be referred to as pixels, and in this specification will be referred to as transducer pixels. The term display pixel will be used to refer to pixels on a display screen. A different group of transducer pixels may be chosen from the same array to obtain an image of a different aperture and/or different perspective. Transducer system 110 may also include acoustical systems for guiding and/or focusing the ultrasound beam, for example. Transducer system 110 may include antireflection layers and/or filters for filtering out noise, for example. Processor system 108 may include one or more specialized processors for controlling transducer system 110 and/or processing signals and/or data received by transducer system 110. An example of the construction a transducer system 110 is shown in U.S. patent application Ser. No. 10/039,910, "System and Method for Coupling Ultrasound Generating Elements to Circuitry" filed Oct. 20, 2001 and cited above.

Communications system 112 communicatively links output system 102, input system 104, memory system 106, processor system 108, transducer system 110, and/or input/output system 114 to each other. Communications system 112 may include any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves.

Input/output system 114 may include devices that have the dual function as input and output devices. For example, input/output system 114 may include one or more touch sensitive screens, which display an image and therefore are an output device and accept input when the screens are pressed by a finger or stylus, for example. The touch sensitive screens may be sensitive to heat and/or pressure. One or more of the input/output devices may be sensitive to a voltage or current produced by a stylus, for example. Input/output system 114 is optional, and may be used in addition to or in place of output system 102 and/or input device 104.

Figure 2:
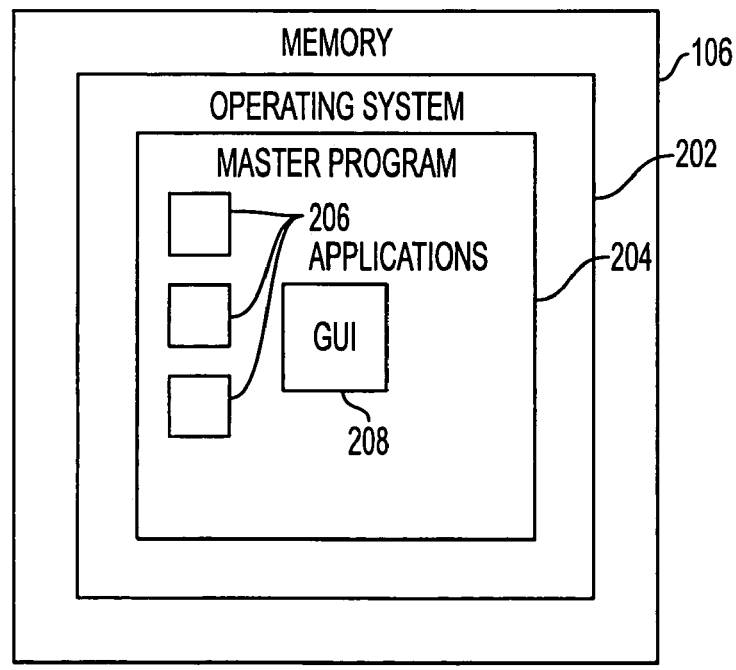
FIG. 2 shows a diagram of the contents of the memory of the ultrasound system of FIG. 1.

FIG. 2 shows a diagram of the contents of the memory system 106 of the ultrasound system 100 of FIG. 1, which includes operating system 202, master program 204, applications 206, and Graphical User Interface (GUI) 208.

Operating system 202 provides the programming framework for master program 204, applications 206, and GUI 208 to run. Master program 204 calls applications 206 and GUI 208 and decides when each application of applications 206 will run. Applications 206 may be programs or objects that are separate from master program 204. Alternatively, any one of, some of, any combination of, or all of applications 206 may be subroutines or lines of code within master program 204 rather than separate programs. One or more of applications 206 may control or perform signal processing for transducer system 110. One or more of applications 206 may process data and/or signals received by transducer system 110. GUI 208 provides guidance to a user as to how and when to enter input that controls master program 204. Alternatively, any part of or all of master program 204, applications 206, and/or GUI 208 may be hardwired into processor system 108 rather than resident in memory system 106.

Figure 3:
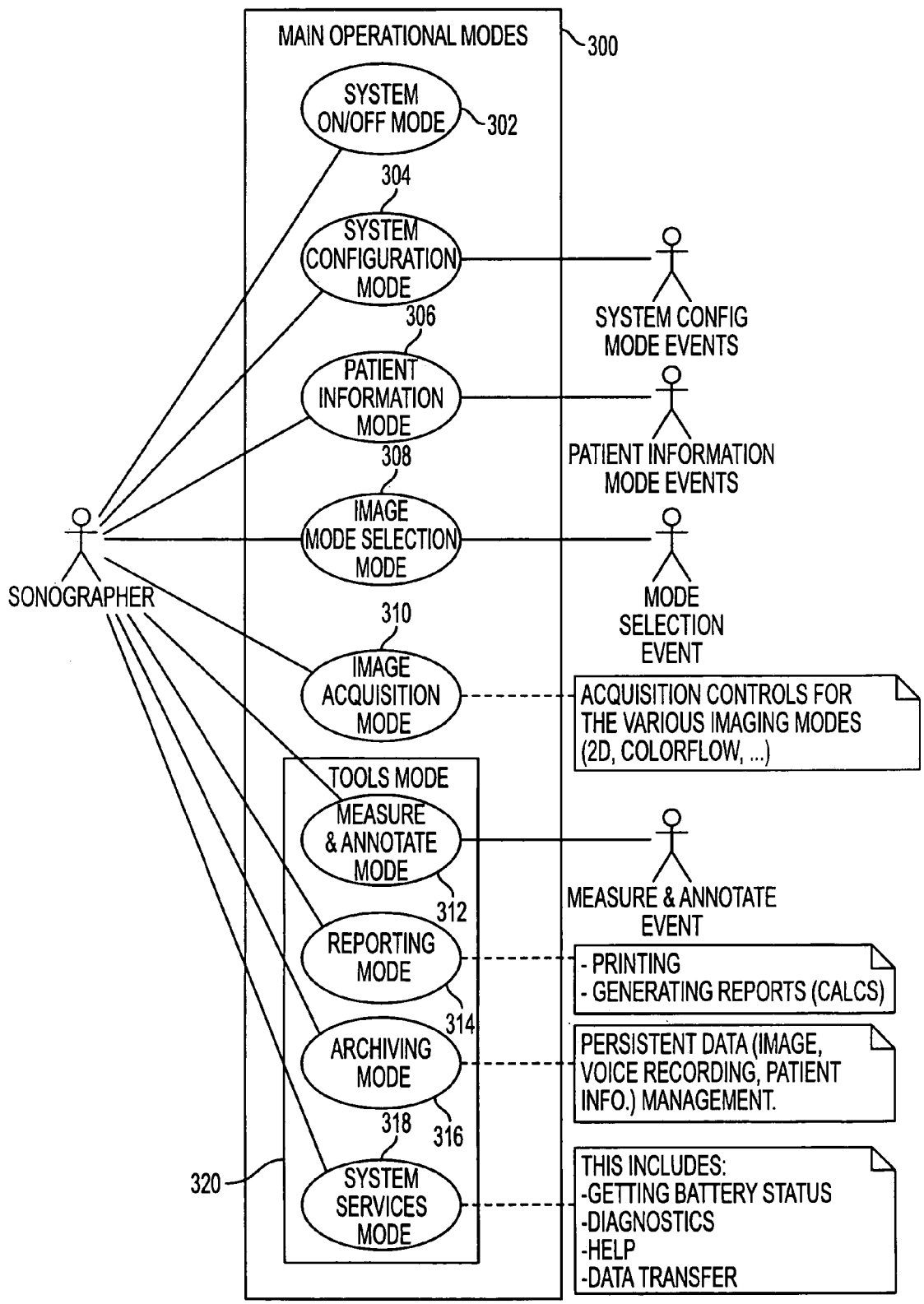
FIG. 3 shows the main operational modes of the ultrasound system.

FIG. 3 shows the main operational modes 300 of the ultrasound system 100, which may include a system on/off mode 302, a system configuration mode 304, a patient information mode 306, an image mode selection mode 308, an image acquisition mode 310, tools mode 320, which may further include a measure and annotate mode 312, a reporting mode 314, an archiving mode 316, and a system services mode 318.

System on/off mode 302 turns on and shuts off the system, and determines the sequence in which various parts of the system are shutdown. In addition to or in place of the on/off buttons, a shutdown icon or tab may be provided on any one of, any combination of, or all of the views of the GUI 208.

System configuration mode 304 allows the user to preset system parameters. The preset system parameters may be set only once by the user upon receiving the ultrasound system 100 or may be set as needed. System configuration mode 304 includes a power on stage during which the system may automatically configure itself. During the power on stage ultrasound system 100 may determine the battery status and/or transducer status when powering up and ultrasound system 100 may configure itself according to the battery and/or transducer status. In an embodiment, different options may be presented to the user depending upon the status of the battery and the status of the transducer. For example, if the battery is very low, the screen may display a message that the battery is low and not allow access to other functions until the battery is recharged. Once the power up is completed the system is ready for data acquisition. System configuration mode 304 may include presets (user preferences for default settings) that determine the configuration of ultrasound system 100 after power up and/or for a given imaging selection. Ultrasound system 100 may have several sets of presets that are used for different users or different types of users. The user may have the option to archive the image's acoustic data, transducer pixel data, and/or display pixel data, and/or to determine the format and file naming convention in which the data is stored, for example. The user may be able to specify the system's language and time formats. The user may be able to specify transducer defaults, such as the type of transducer in use and the central frequency. For example, a transducer default may be that the type of transducer used is a phased array that has a central frequency of 3.0 MHz. The user may be able to set screen defaults such as brightness, contrast, color, arrangement of tiles and the data acquisition mode (e.g., B-mode) the ultrasound system 100 is in at power up. System configuration mode 304 is discussed further in conjunction with FIG. 4, below.

Patient information mode 306 includes entering and modifying data identifying and/or describing a patient, which may include filling in data fields. The data fields may be text boxes. In an embodiment, patient data shall be saved with each study. Patient information mode 306 may include allowing a user to view all or a subset of the data about a patient. After the study is complete, the data fields may be amended. Patient information mode 306 is discussed further in conjunction with FIG. 5, below.

During image mode selection mode 308, ultrasound system 100 may be placed in one of several acquisition modes, such as B-mode, M-mode, color flow mode, Continuous Wave (CW) Doppler mode, and/or Pulsed Wave (PW) Doppler mode. In B-mode the ultrasound data is displayed as a grayscale image map (e.g., 256 gray shades). The transducer pixel intensities and therefore the display pixel intensities correspond to the ultrasound strength. The location of each transducer and display pixel corresponds to the depth of the signal. During color flow Doppler mode color codes may be used to display velocity information from multiple color sample lines, which may then be processed via autocorrelation, for example. Image mode selection mode 308 is discussed further in conjunction with FIG. 6, below.

Image acquisition mode 310 gathers data to form images. The mode of the data acquisition may be set during the operational mode of image mode selection mode 308. Alternatively, the mode for image acquisition mode may be set separately and independently from the image mode selected via image mode selection mode 308. In an embodiment, the data can be viewed while being acquired. In an embodiment, the screen may be frozen using a stop/start toggle, for example, while acquiring data. During image acquisition mode 310 various imaging parameters can be adjusted, such as depth, gain, and zoom. The image may be displayed in various display formats depending on the imaging mode. For example, if the imaging mode is PW Doppler, the user may be allowed to display color flow image only, spectral only, or both. In an embodiment, of image acquisition mode 308, the data can be viewed without a control panel present. The window showing the data can be expanded to cover the entire screen.

Measure and annotate mode 312 includes performing measurements on and adding annotations to an image. Measure and annotate mode 312 is discussed in FIGS. 15 and 16, below.

Reporting mode 314 allows the user to print images, measurements, and calculations to a printer or a file and may allow the user to organize, categorize, and/or tabulate reports and/or data such as that gathered using measure and annotate mode 312. Reports can be generated in tabular or graphical form. Reporting mode 314 is discussed below in conjunction with FIG. 17.

Archiving mode 316 allows for the storage of large amounts of data and/or files such as images and/or sound files. The format of the stored data can be chosen. Archiving mode 316 may include functions for exporting data and/or images. Archiving mode 316 may allow the images and/or data to be searched, viewed, and/or stored on the ultrasound system 100 or another system.

System services mode 318 includes performing system diagnostics, getting the battery status, providing help, and/or controlling data transfer. Among other things, system services may include all monitoring functions available to the system.

Figure 4:
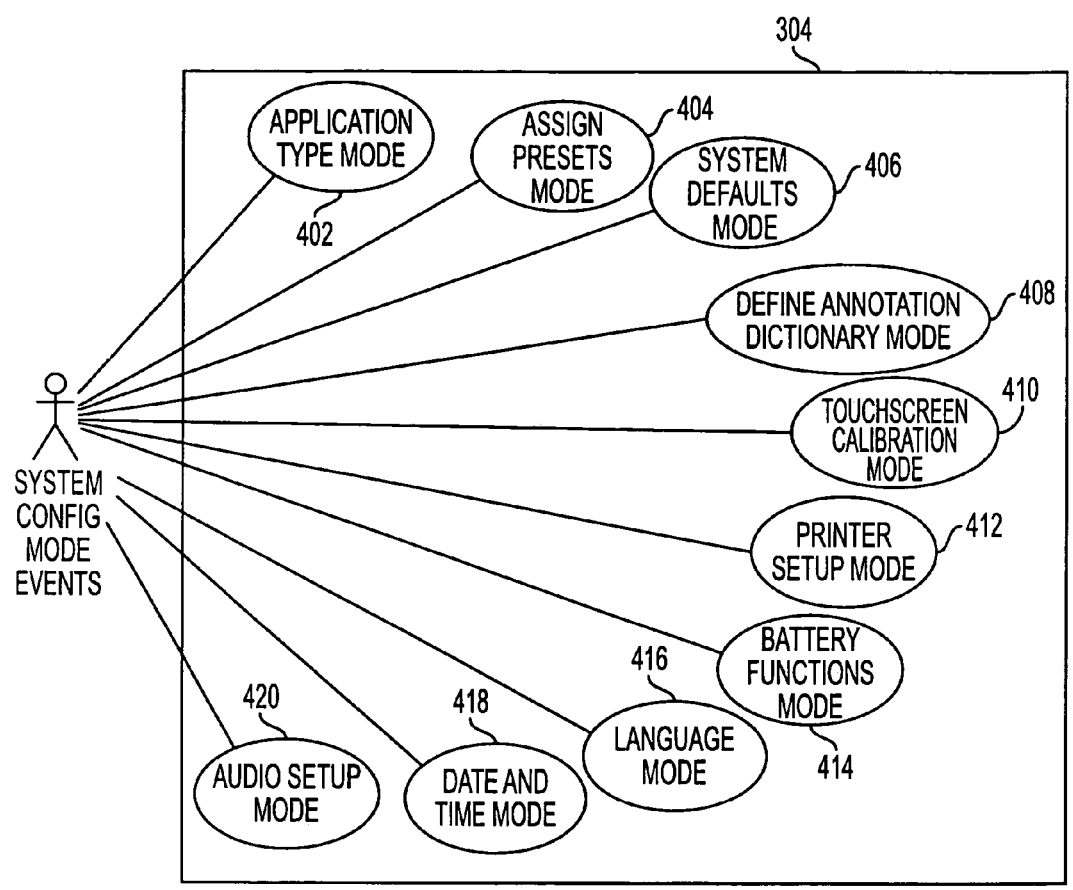
FIG. 4 shows the system configuration mode of the ultrasound system.

FIG. 4 shows the system configuration mode 304 of the ultrasound system 100, which includes application type mode 402, assign presets mode 404, system defaults mode 406, define annotation dictionary mode 408, touchscreen calibration mode 410, printer setup mode 412, battery function mode 414, language mode 416, date and time mode 418, and audio setup mode 420.

Application type mode 402 determines the mode of operation that the ultrasound system 100 is in at any given time and/or upon startup. The mode of operation at startup may be made to depend upon which user logs in, if there are multiple users. For example, the same ultrasound system may be used by a nurse, technician, cardiologist, Obstetrician/Gynecologist (OB/GYN) and/or a radiologist. Depending upon which logs in, a different set of functions and applications appears on the screen at startup. Application type mode 402 may also control changing applications during operations.

Assign presets mode 404 allows the user to specify her or his specific presets. For example, the same ultrasound system 100 may be used by multiple cardiologists, each having her or his own preferences for how to view and/or annotate the data. Assign presets mode 404 may allow each user to assign her or his individual presets.

System defaults mode 406 may include archival options such as the format or formats in which an image is automatically saved. For example, the user may be able to choose the default coordinate systems for graphs such as units of electrical current, units of electrical charge, and/or polar coordinates. Images may be 640×480 display pixels, and may be data formatted as Digital Imaging and Communications in Medicine (DICOM) or Microsoft Bit Map (BMP), for example. The system defaults may also control the form of compression for the stored image. An Infrared (IR) connection or other form of propagating a signal through air or through a cable may be used to transmit a screen-captured image to a printer. System defaults mode 406 may also include the format of the date. The system user may be given the option to select the date formats, such as mm-dd-yyyy or dd-mm-yyyy. The user may be allowed to set the system date and time and the format in which the time is displayed, such as English, European, or military time. The user may be able to specify the default frequency for one or more transducer types. The user may be able to specify a default screen brightness level and the screen layout. The user may be able to select the location and colors of tool bars, the control areas and/or the image areas on the display. Alternatively, a separate default mode for the user to set transducer defaults may be provided.

Define annotation dictionary mode 408 may allow the user to enter a spelling dictionary to be used to check spelling while making annotations. Optionally, define annotation dictionary 408 may also allow the user to access a thesaurus for choosing the wording of annotations. Define annotation dictionary 408 may also allow the user to establish a dictionary (e.g., a list) of common annotations or common types of annotations to choose from that can be added to an image or build a thesaurus of annotations that can be substituted one for another. The annotation dictionary (associated with define annotain dictionary mode 408) and/or thesaurus may include icons and text such as units, Greek letters, mathematical or medical symbols, and/or medical or ultrasound terms.

Touchscreen calibration mode 410 is optional and may be left out in embodiments of ultrasound system 100 not having a touchscreen. Touchscreen calibration may allow the user to establish positioning or reference coordinates, which may be established with the use of a stylus or by entering the coordinates into a dialogue box, for example. Touchscreen calibration mode 410 may additionally or alternatively allow the user to change the sensitivity of the touchscreen and/or which parts of the touchscreen respond to touch. The user may be able to change the sensitivity so that different parts of the screen have different sensitivities. Also, for example, the user may be able to change the size of the interactive touchscreen portion.

Printer setup mode 412 may allow the user to choose the type of printer, the location of the printer, the type of paper, the orientation of the image on the paper, how many and the tiling of the images in the view or frame of a page about to be printed, whether to print to paper or to a file, the margins and/or the fonts, for example.

The battery function mode 414 may include an estimate of how much longer the battery will last using the current system settings. In an embodiment, the user may use battery function mode 414, for example, understand how keeping a particular feature active affects the battery lifetime. In an embodiment, the user could use battery function mode 414 to simply monitor how much battery life remains.

Language mode 416 allows the user to choose the language (e.g., Japanese) in which ultrasound system 100 will display information. In an embodiment, the user can choose a code or an interactive code language, such as graffiti.

Date and time mode 418 allows the user to set the date and time. An example of a user selectable setting is setting the ultrasound system 100's clock to automatically switch to daylight savings. The format of the time discussed in conjunction with system defaults mode 406 may be adjustable through date and time mode 418 in addition to or instead of being adjustable through system defaults mode 406.

Audio setup mode 420 may allow the user to set the volume during recording and broadcasting. The user may also be able to choose which features will be voice enabled. Audio setup mode 420 may also provide training sessions to train the ultrasound system 100 to recognize the user's voice or to recognize specific commands.

Although not shown system configuration mode 304 may include a Region of Interest (ROI) defaults mode that allows the user to select the default size, shape and position of the ROI. In an embodiment, the user may be able to select a type of feature that the ROI will automatically include. A mode may also be included for choosing the startup screen. Alternatively, ROI defaults and setting the startup screen may be part of system defaults mode 406. Any one of, any combination of, or all of the system configuration parameters may be part of one or more presets or defaults and adjustable using assign presents mode 404 and/or system defaults mode 406.

Figure 5:
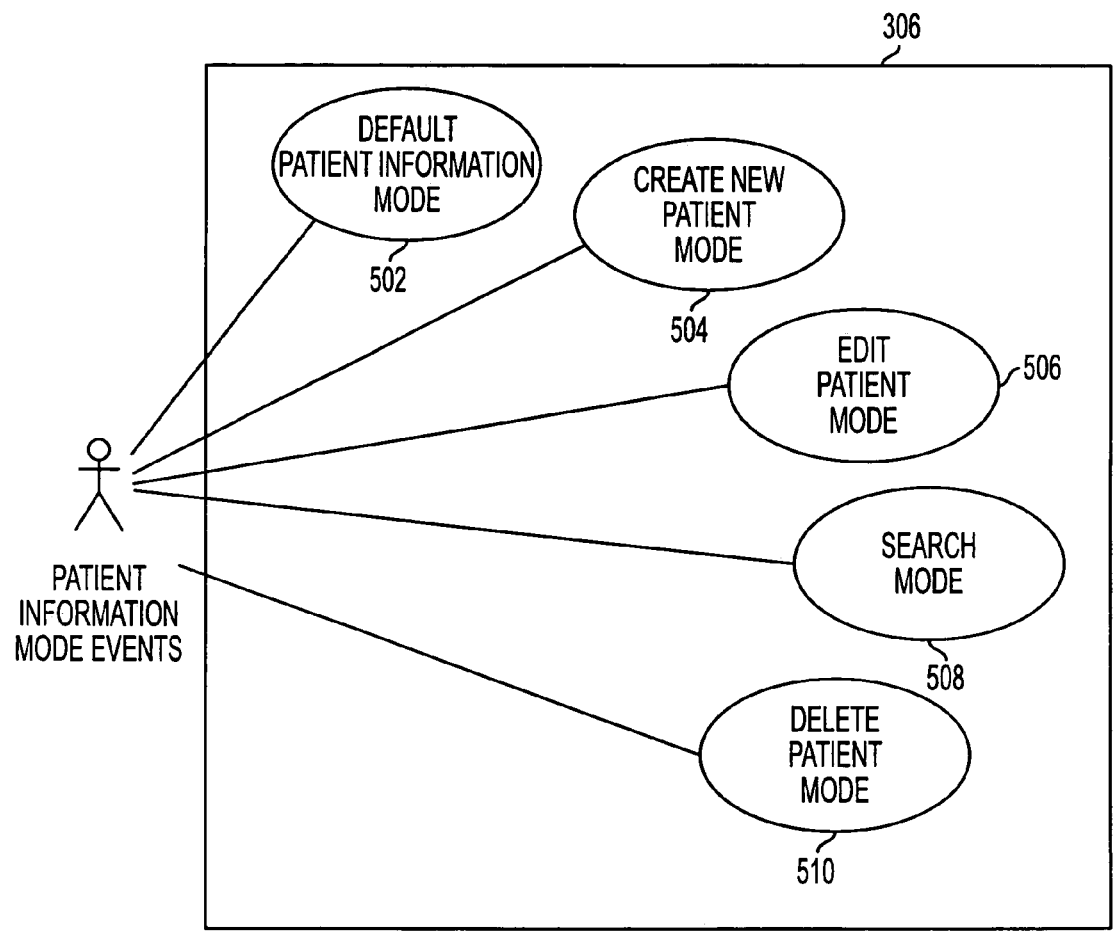
FIG. 5 shows the patient information mode of the ultrasound system.

FIG. 5 shows the patient information mode 306 of the ultrasound system 100, which includes default patient information mode 502, create new patient mode 504, edit patient mode 506, search mode 508, and delete patient mode 510.

Default patient information mode 502 displays the information associated with a default patient. The default patient may be the patient that was being tested last or whose medical information was being reviewed last, for example. When entering the patients name the ultrasound system 100 may guess at who the patient is based on parameters such as the frequency the patient's information was viewed in the past and/or the letters of the patient's name that were entered. As more letters are entered, ultrasound system 100 may update its guess as to which patient should be displayed. The user may have a choice as to the basis of choosing the default patient.

Create new patient mode 504 sets up space in memory identified with a new patient. An example of such a space is a new folder for the new patient. The new folder may be created or downloaded automatically by another system associated with a hospital or doctor's office, for example. Continuing with the example, the automatic file download or creation may occur upon an entry to the other system, a determination that an ultrasound scan should be performed, and/or the next time after the entry that the ultrasound system 100 is connected to the other system. The user could determine when and how frequently the other system is checked for new patients. The number of patient files stored in ultrasound system 100 may be significantly smaller than the total number of patients in the other system so as not to burden ultrasound system 100 with storing the other system's entire database of patients. After examining one group of patients create new patient mode 504 may create a new group of patients that have not been examined yet or that needs further testing.

Edit patient mode 506 may allow the user to edit patient information. It may be possible to edit any patient information entered during create new patient mode 504. In an embodiment, immediately after a new patient folder is opened in the create new patient mode 504, ultrasound system 100 switches to edit patient mode 506 where the information about the new patient is entered.

Search mode 508 allows the current database of patients to be searched. The search may be performed by searching for a string of search terms connected together by logical operators. The terms may include keywords and the user may be capable of limiting the search for one or more of the keywords to specific fields, such as patient name or attending physician. The string of search terms may include smaller strings of search terms that are searched in a specific field.

Delete patient mode 510 may allow for the deletion of a patient from the ultrasound system 100. Delete patient mode 510 may allow for the deletion of the information associated with one or multiple patients simultaneously. So as not burden ultrasound system 100 with storing another system's entire database of patients, after downloading the patient information of a first group of examined patients, delete patient mode 510 may delete the patient information of that group so that another group of patient information files can be downloaded to ultrasound system 100.

Figure 6:
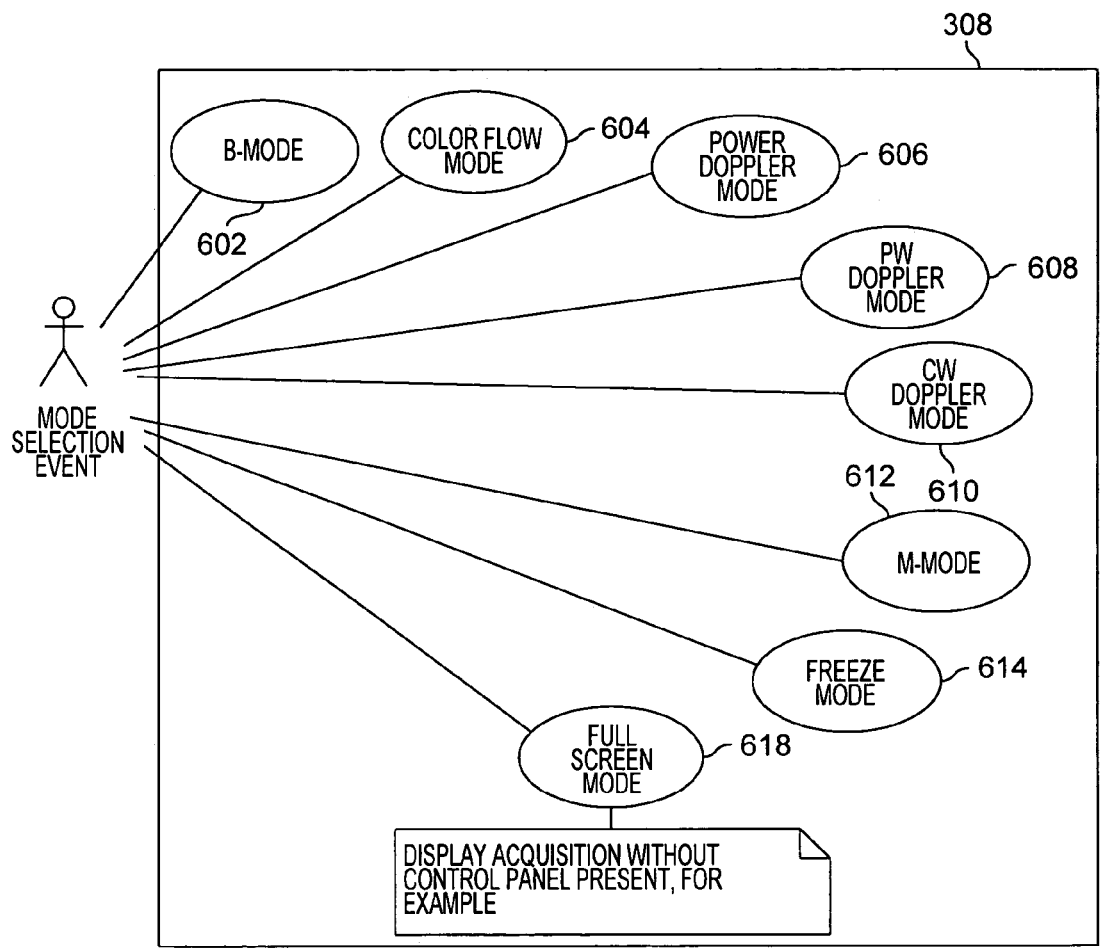
FIG. 6 shows the mode selection mode of the ultrasound system.

FIG. 6 shows the image mode selection mode 308 of the ultrasound system 100, which may include any one of, some of, any combination of, or all of B-mode 602, color flow mode 604, power Doppler mode 606, PW Doppler mode 608, Continuous Wave (CW) Doppler mode 610, M-mode 612, freeze mode 614, and full screen mode 618.

Although not shown other modes that may be included in image mode selection mode 308 are B-flow mode, color Doppler mode, color M-mode, A-mode, and tissue harmonics mode, for example. PW Doppler can be mixed with nearly any mode while CW Doppler is usually used alone but can also be combined with other modes within image mode selection mode 308. Combinations of modes are possible, for example, some possible mode combinations that may be included in ultrasound system 100 are B-mode and color-PW Doppler, B-mode and color M-mode, and/or and B-flow mode.

B-mode 602 produces a two-dimensional array of points, each point varies in brightness according to an echo's strength. Generally the strength of the echo corresponds to the location of the source of the echo. Consequently, the image produced is similar to a photographic or x-ray image. B-mode 602 is discussed further in FIG. 7, below.

Color flow mode 604 uses color to display velocity and/or flow. The flow may be determined using the Doppler effect in combination with a Doppler mode of operation or by plotting the changes in position of objects that are being carried by the flowing material. Color flow mode 604 is further discussed in FIG. 8, below.

The Doppler effect is used to determine flow information in the power Doppler mode 606, PW Doppler mode 608, and CW Doppler mode 610. Different velocities correspond to different changes in the frequency of the sound. The shift between the transmitted and received signal is measured. The lack of any shift indicates that the object is stationary. A positive shift indicates flow in one direction and negative flow indicates flow in the other direction.

Power Doppler mode 606 displays the strength of the Doppler shifted echoes as pulses on a graph having the strength of the shift on one axis and time on another. The strength of the Doppler shifted echoes could be measured in several ways, such as the amplitude, power, intensity, or energy of the signal. Power Doppler mode 606 may show how strong of a reflection occurs at each point measured. Power Doppler mode 606 is discussed in FIG. 9, below.

PW Doppler mode 608 uses ultrasound pulses rather than a continuous wave. PW Doppler mode 608 is also called the spectral Doppler mode. PW Doppler mode 608 studies a sampled set of the flow velocity at a point or finite region giving the spectrum of velocities at that region. A set of transducer elements sends pulses and the same or a different set of ultrasound transducer elements listens for the pulses after they are modified (e.g., reflected) by a medium under investigation. The motion monitored by PW Doppler is sampled rather than continuously monitored because of the use of the pulses. PW Doppler mode 608 is further discussed in FIG. 10, below.

CW Doppler mode 610 uses a continuous ultrasound wave to produce the Doppler shift in frequency to study the average velocity along a line. Some transducers in the array are dedicated to transmitting the ultrasound signal continuously, while others are dedicated to receiving the ultrasound signal continuously. CW Doppler mode 610 is further discussed in FIG. 11, below.

The color flow mode 604 can be combined with any of the power Doppler mode 606, PW Doppler mode 608 and/or CW Doppler mode 610, color coding the velocities, for example.

M-mode 612 studies a strip or a line along a medium under investigation rather than giving a two-dimensional image plotted as echo penetration depth versus time. This mode is used for studying motion. Stationary structures appear as straight lines. M-mode 612 is further discussed in FIG. 12, below.

Color M-mode has the color flow mode overlaid on the M-mode.

Color Doppler mode shows the B-mode either moving or frozen at the same time as the Doppler mode. A ROI showing the flow information is placed above the Doppler image.

B-flow mode represents the flow as motion just as flow would appear in an anatomically correct image. The flow appears as changes in the speckled pattern. The B-flow mode may be facilitated by using broad beam technology, because by gathering the data with a broad beam rather than a pencil beam and/or by processing the flow data and the B-mode data simultaneously fewer transmit receive cycles are necessary to obtain an image than would be used by beam forming technology. Consequently, the motion of the vessel containing the flow is removed or reduced when compared to a prior art beam forming method.

The modes that could be included in image mode selection mode 308 are not limited to those shown, discussed, or depicted. For example, although not shown a tissue harmonics mode could also be included in image mode selection mode 308. A tissue harmonics mode is a two-dimensional gray scale image that measures nonlinearities in tissue. One way of accomplishing this gray scale imaging is by looking at the first order harmonics rather than the fundamental harmonic. Tissue harmonics mode can be useful in determining the nature of an interface, such as a tissue interface, for example. Other modes could include looking at second and higher order harmonics in a two-dimensional gray scale plot.

Another imaging mode that may be incorporated in some embodiments of ultrasound system 100 is A-mode, which is a plot of echo amplitude versus depth into the medium under investigation. This mode is sometimes used in ophthalmology.

Freeze mode 614 allows the image to be held frozen (e.g., by pressing a stop/start toggle) during data acquisition so that the image can be annotated and measurements can be taken on the image. Freeze mode 614 may be capable of displaying a split screen in which half of the screen is frozen and the other half shows the data being acquired or a cinema (cine) loop. Freeze mode 614 will be discussed further in conjunction with FIG. 13, below.

Full screen mode 618 allows the user to view the image without viewing a control panel or tool bar. The image may appear with some annotations to allow the user to know the settings being used and/or some patient information and/or history. Alternatively, the image may be viewable without any annotations or the annotations may appear as a default but can be removed after the data is acquired and/or the image is expanded to the full screen.

Figure 11:
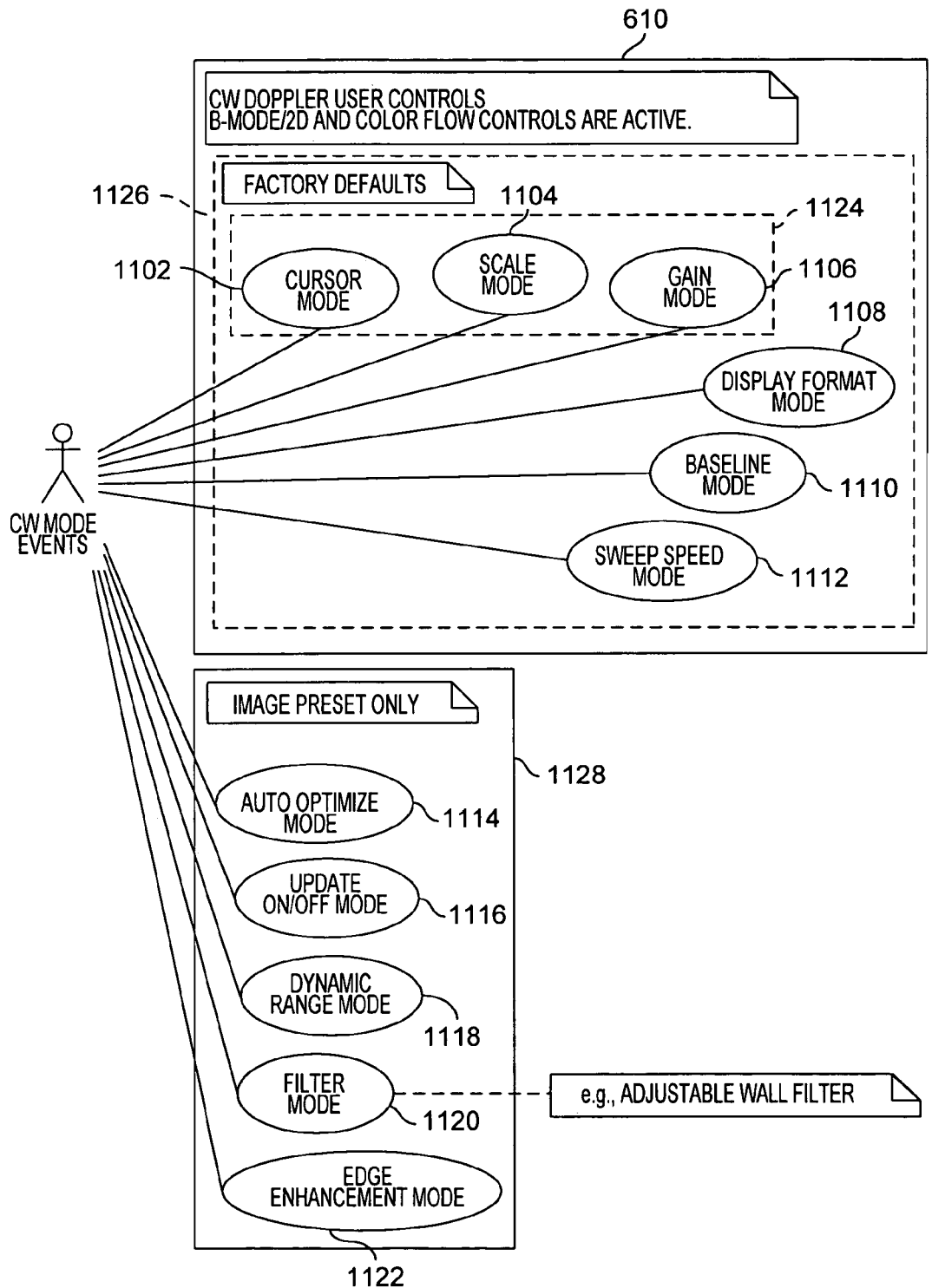
FIG. 11 shows the Continuous Wave (CW) Doppler mode of the ultrasound system.
Figure 12:
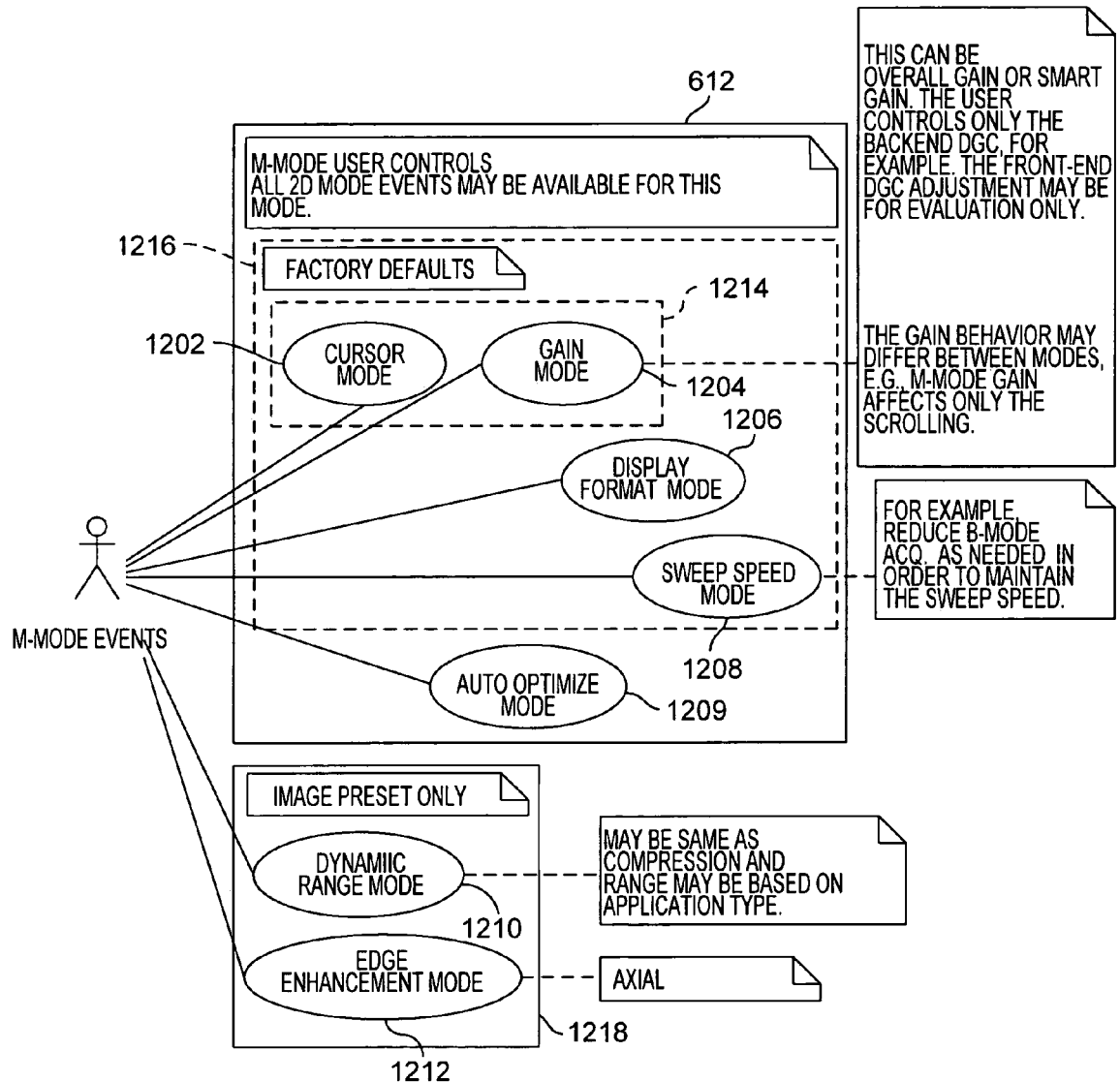
FIG. 12 shows the M-mode of the ultrasound system.
Figure 13:
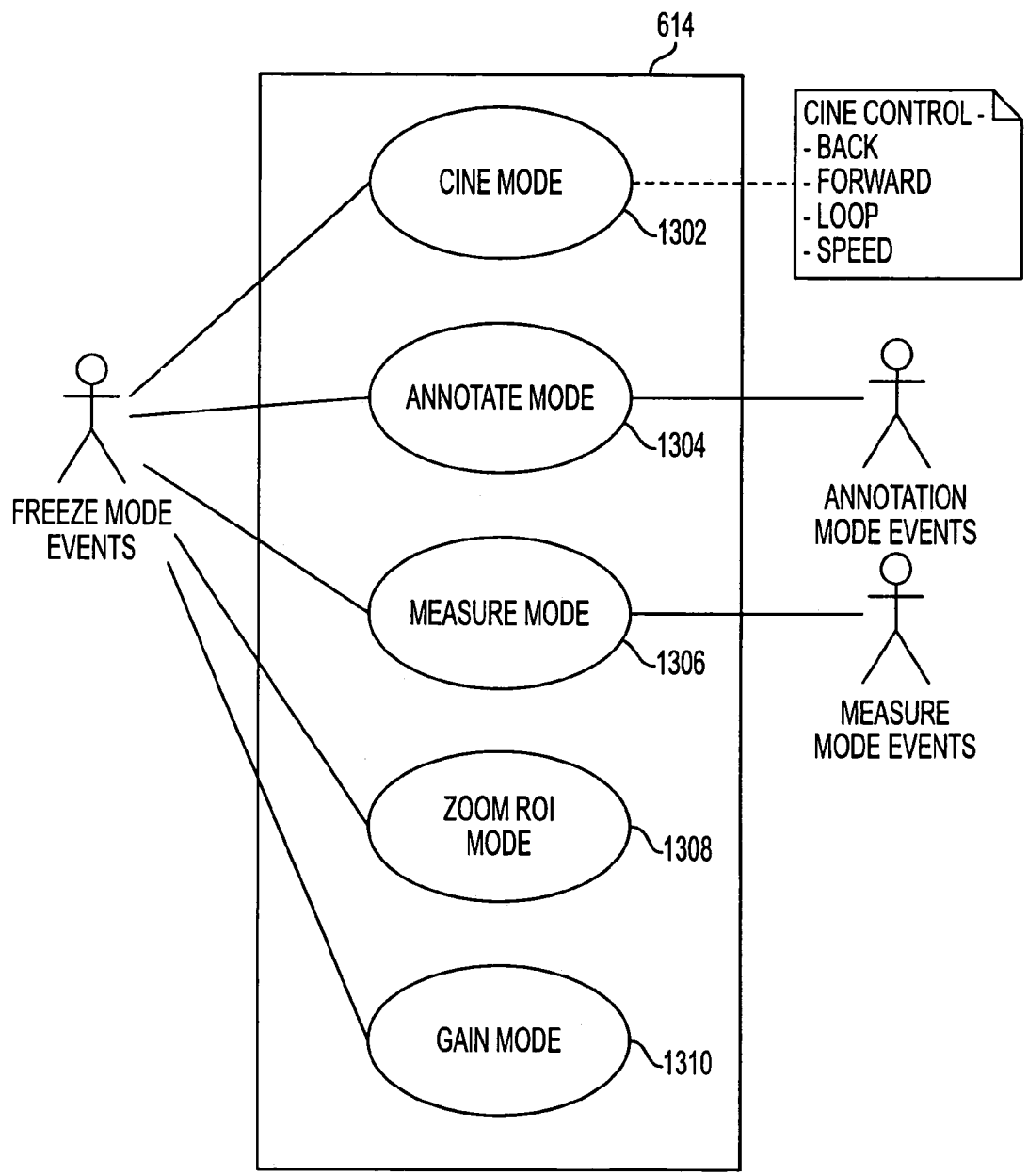
FIG. 13 shows the freeze mode of the ultrasound system.

FIGS. 7–13 have several modes in common, which will be described together immediately after FIG. 13.

Figure 7:
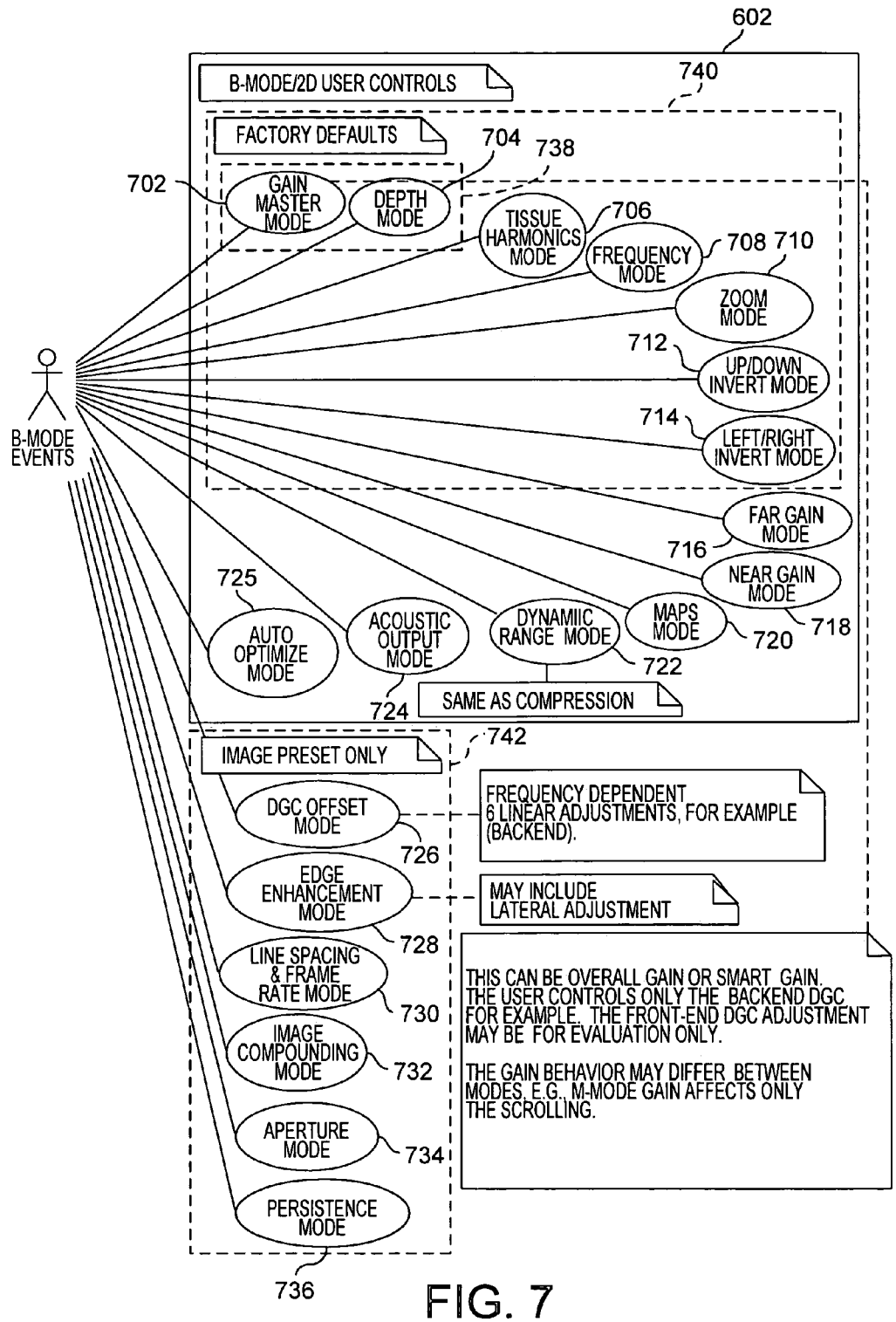
FIG. 7 shows the B-mode of the ultrasound system.

FIG. 7 shows the B-mode 602 of the ultrasound system 100, which includes minimal modes 738 having gain mode 702 and depth mode 704 and factory defaults 740 including minimal modes 738, tissue harmonics mode 706, frequency mode 708, zoom mode 710, up/down invert mode 712, and left/right invert mode 714. B-mode 602 of FIG. 7 also includes far gain mode 716, near gain mode 718, maps mode 720, dynamic range mode 722, acoustic output mode 724, auto optimize mode 725, and image presets 742 having Depth Gain Compensation (DGC) offset mode 726, edge enhancement mode 728, line spacing and frame rate mode 730, image compounding mode 732, aperture mode 734, and persistence mode 736.

Depth mode 704 is used to determine the depth of the field of view of the ultrasound image and/or to determine the depth at which the data is to be gathered. Lower frequencies are used for deeper imaging, while higher frequencies are used for more shallow imaging.

Tissue harmonics mode 706 was explained in conjunction with FIG. 6. In an embodiment, when ultrasound system 100 is in tissue harmonics mode 706 all of the modes available under B-mode 602 are available. Although tissue harmonics mode 706 is illustrated as a mode of the B-mode 602, tissue harmonics mode 706 or any one B-mode 602's modes could be its own mode of operation.

Frequency mode 708 allows the user to set the frequency of the ultrasound pulse being transmitted from the transducer array. Zoom mode 710 allows the user to get an exploded view of a region of interest. Maps mode 720 allows the user to set the gray scale, which may be a linear, logarithmic, or another nonlinear function.

Up/down invert mode 712 and left/right invert mode 714 can be used to accommodate viewing a display screen from a different orientation. Up/down invert mode 712 allows the user to flip the image region and/or the entire GUI 208 about a horizontal line at the center of the screen thereby switching top and bottom, while left/right invert mode 714 allows the user to flip the image and/or the entire GUI about a vertical line at the center of the image thereby switching right and left and creating a mirror image. Alternatively, up/down invert mode 712 may rotate the image until it is upside down while left/right invert may rotate the image until the top of the image is to the right of the screen or the left of the screen.

Far gain mode 716 allows the user to alter the gain in a region of the image far from the location of the transducer in the image, while near gain mode 718 allows the user to alter the gain in a region of the image near to the location of the transducer in the image. The gain within the regions in between automatically adjusts so that the gain varies smoothly across the image.

Dynamic range mode 722, acoustic output mode 724, and auto optimize mode 725 are discussed below.

DGC (also referred to as Time Gain Correction (TGC)) mode 726 is used to compensate for attenuation of the signal due to the depth the signal traveled into the medium under investigation so that the image has a uniform brightness. DGC mode 726 is similar to the combination of far gain mode 716 and near gain mode 718, except that DGC mode 726 divides the whole field of view in multiple zones (e.g., six) or continuously varies the gain according to a function of depth rather than dividing the field of view in two zones (far and near). The user may be allowed to adjust the amount of gain and/or how the gain varies using DGC mode 726. Alternatively, DGC mode 726 may be a digital gain correction mode, which controls the offset for the gain rather than a multiplicative increase of the gain. In an embodiment, B-mode may include both a digital gain correction mode and a dynamic gain correction mode.

Edge enhancement mode 728 is described below.

Line spacing and frame rate mode 730 controls the spacing between lines on the display screen, which controls the resolution and also controls the time between frames.

Image compounding mode 732 combines multiple images into one image. For example, the images may be taken at different frequencies to get different depths. Image compounding mode 732 is dependent on the type of imaging mode. Inage compounding mode 732 may be dependent also on the transducer type because different transducer types tend to be used for different types of imaging. For example, in B-mode 602 the user is likely to want to change the frequency to image different depths, while with a linear array transducer the user may want to form a compound image made up of images formed from different groups of transducer pixels. Image compounding from different positions using B-mode imaging may involve determining how the images from different positions overlap one another, such as by finding common elements on both images and matching them.

Aperture mode 734 determines the magnitude or intensity of the transmit profile. A flat aperture has an equal intensity for all transducer pixels. Aperture mode 734 is useful in apodisation or in shaping the ultrasound beam to be more Gaussian. Aperture mode 734 may also include a determination of which transducer pixels on a two-dimensional array are to be used for imaging and/or a determination of the shape of the transmit profile.

Persistence mode 736, minimal modes 738, factory defaults 740, and image presets 742 are discussed below.

Figure 8:
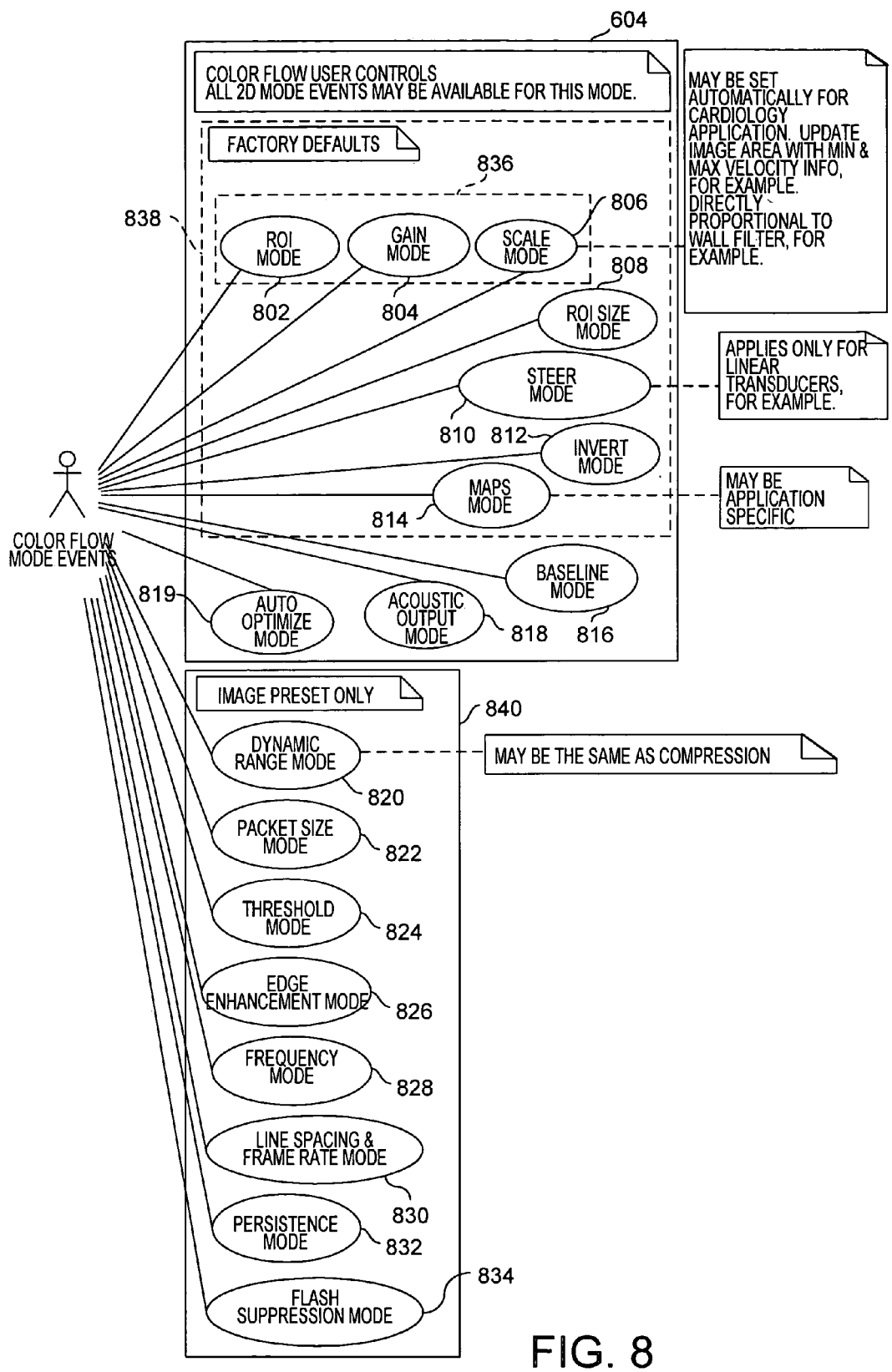
FIG. 8 shows the color flow mode of the ultrasound system.

FIG. 8 shows the color flow mode 604 of the ultrasound system 100, having minimal modes 836 including ROI mode 802, gain mode 804, and scale mode 806, and factory defaults 838 including minimal modes 836, ROI size mode 808, steer mode 810, invert mode 812, and maps mode 814. Color flow mode 604 also includes baseline mode 816, acoustic output mode 818, auto optimize mode 819, and image presets 842 including dynamic range mode 820, packet size mode 822, threshold mode 824, edge enhancement mode 826, frequency mode 828, line spacing and frame rate mode 830, persistence mode 832, and flash suppression mode 834.

ROI mode 802, gain mode 804, and scale mode 806 are discussed below.

During ROI size mode 808 the user can choose the size of the ROI. During steer mode 810 the user can change the direction of the ultrasound beam. Invert mode 812 inverts the color coding changing the low frequency (or long wavelength) colors to high frequency (or short wavelength) colors and high frequency (or short wavelength) colors to low frequency (or long wavelength) colors so as to change the direction of flow.

Maps mode 814, baseline mode 816, acoustic output mode 818, auto optimize mode 819, dynamic range mode 820, packet size mode 822, threshold mode 824, edge enhancement mode 826, frequency mode 828, line spacing and frame rate mode 830, persistence mode 832, and flash suppression mode 826, minimal modes 836, factory defaults 838, and image presets 840 are discussed below.

Figure 9:
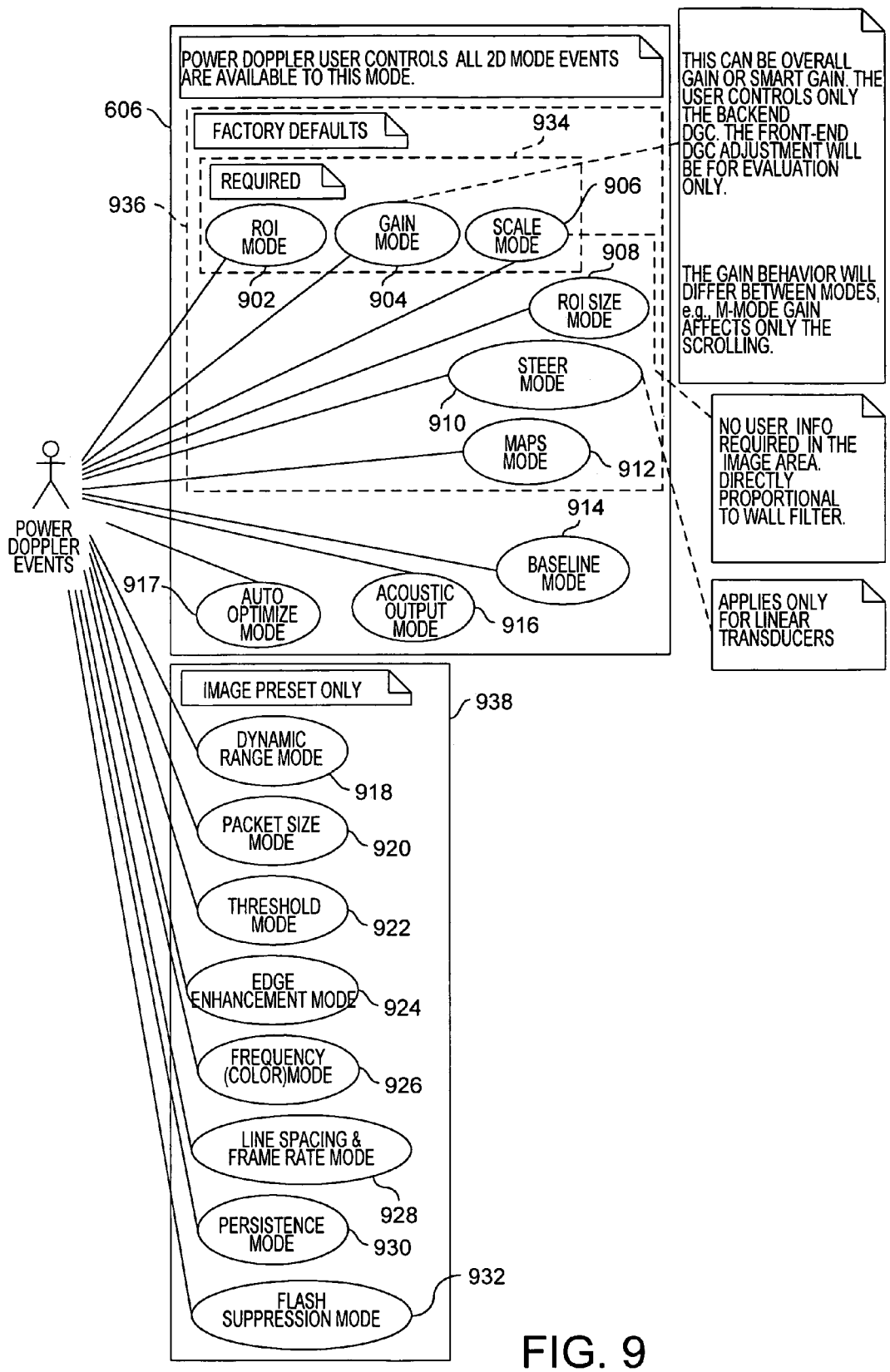
FIG. 9 shows the power Doppler mode of the ultrasound system.

FIG. 9 shows the power Doppler mode 606 of the ultrasound system 100, having minimal modes 934 including ROI mode 902, gain mode 904, and scale mode 906 and factory defaults 936 including minimal modes 934, ROI size mode 908, steer mode 910, and maps mode 912, which are discussed below. Power Doppler mode 606 also has baseline mode 914, acoustic output mode 916, auto optimize mode 917, and image presets 938 including dynamic range mode 918, packet size mode 920, threshold mode 922, edge enhancement mode 924, frequency mode 926, line spacing and frame rate mode 928, persistence mode 930, and flash suppression mode 932, which are also discussed below.

Figure 10:
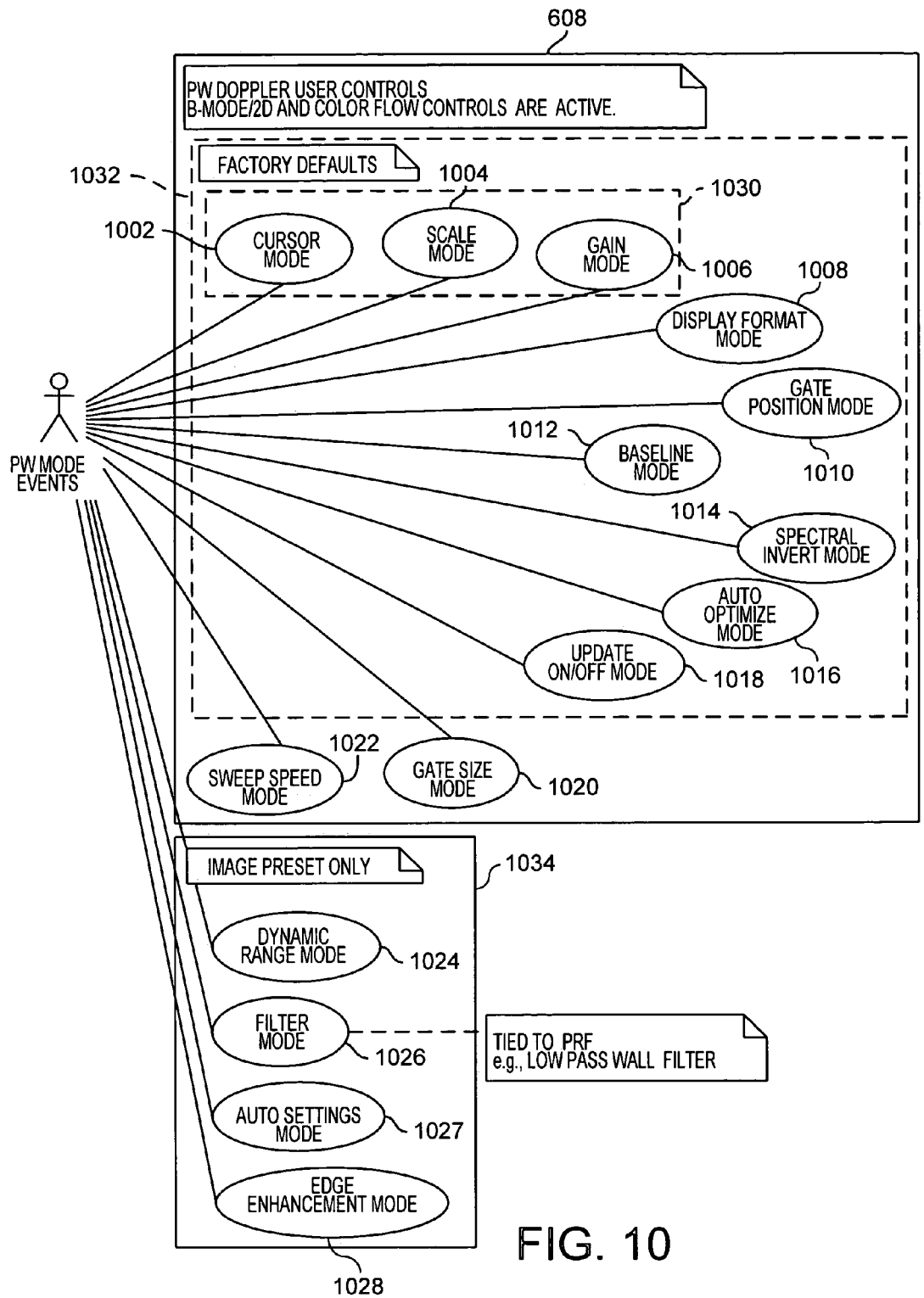
FIG. 10 shows the Pulsed Wave (PW) Doppler mode of the ultrasound system.

FIG. 10 shows the PW Doppler mode 608 of the ultrasound system 100, having minimal modes 1030 including cursor mode 1002, scale mode 1004, and gain mode 1006 and factory defaults 1032 including minimal modes 1030, display format mode 1008, gate position mode 1010, baseline mode 1012, spectral invert mode 1014, auto optimize mode 1016, and update on/off mode 1018. PW Doppler mode 608 of FIG. 10 also includes gate size mode 1020, sweep speed mode 1022, and image presets 1034 having dynamic range mode 1024, filter mode 1026, audio settings mode 1027, and edge enhancement mode 1028.

Cursor mode 1002, scale mode 1004, gain mode 1006, display format mode 1008 are discussed below.

Gate position mode 1010 determines the position and gate size mode 1020 determines the size of the gate (i.e., window) of the PW Doppler mode 608. To elaborate, the PW Doppler mode 608 has a line along which the PW Doppler data is measured. Along that line the position that the PW Doppler mode 608 measurement is taken can be varied and the size of the region from which the data is gathered can also be varied. The gate size is the size of the region from which the data is gathered, and the gate position is the position from which the data is gathered.

Baseline mode 1012 will be described below.

Spectral invert mode 1014 inverts the spectrum so as to invert the direction of flow.

Auto optimize mode 1016 and update on/off mode 1018 are discussed below.

Seep Speed mode 1022, dynamic range mode 1024, and filter mode 1026 are discussed below.

Audio settings mode 1027 allows the user to hear the Doppler spectrum rather than just see it. When using headphones, the flow direction can be indicated by the ear to which the sound is sent. The user may be able adjust the function that maps the velocity to the sound by changing the volume or the gain associated with the sound, for example.

Edge enhancement mode 1028, minimal modes 1030, factory defaults 1032, and image presets 1034 are discussed below.

FIG. 11 shows the CW Doppler mode 610 of the ultrasound system 100, having minimal modes 1124 including cursor mode 1102, scale mode 1104, and gain mode 1106 and factory defaults 1126 including minimal modes 1124, display format mode 1108, baseline mode 1110, sweep speed mode 1112, and image presets including auto optimize mode 1114, update on/off mode 1116, dynamic range mode 1118, filter mode 1120, and edge enhancement mode 1122.

Cursor mode 1102, scale mode 1104, gain mode 1106, display format mode 1108, baseline mode 1110, sweep speed mode 1112, auto optimize mode 1114, update on/off mode 1116, dynamic range mode 1118, filter mode 1120, and edge enhancement mode 1122, minimal modes 1124, factory defaults 1126, and image presets 1128 are discussed below.

FIG. 12 shows the M-mode 612 of the ultrasound system 100, having minimal modes 1214 including cursor mode 1202 and gain mode 1204. M-mode 6112 also includes factory defaults 1216 having minimal modes 1214, display format mode 1206, and sweep speed mode 1208. M-Mode 612 of FIG. 12 also includes auto optimize mode 1209 and image presets having dynamic range mode 1210, and edge enhancement mode 1212. All of the modes of FIG. 12 are discussed below.

FIG. 13 shows the freeze mode 614 of the ultrasound system 100, having cine mode 1302, annotate mode 1304, measure mode 1306, zoom ROI mode 1308, and gain mode 1310.

Cine mode 1302 allows the user to view a group of images as a motion picture. The motion picture can be stopped and started using a start/stop toggle or a freeze/unfreeze icon, for example. The user can also control whether the group of images under the cine control of cine mode 1302 is being viewed backwards or forwards, whether the set of images should automatically be viewed over again after reaching the last image, how many times the set of images should be viewed and the speeds with which the images are displayed (i.e., the time between the displaying two images), for example. Cine mode 1302 may also or alternatively allow individual frames to be viewed a single frame at a time, and may have controls available to the user for stepping forward or backward one frame at a time. In an embodiment, cine mode 1302 may have options for skipping one or more frames each time it steps forward or backward. In an embodiment, the frames may be viewed while skipping one or more individually selected frames or groups of frames. In an embodiment, the frames may be viewed while skipping one or more frames at fixed intervals.

In an embodiment, the display screen may present video recorder or Video Conference Recorder (VCR)-like controls, which are described further in connection with FIG. 31C, below. In an embodiment, the icons used for the cine controls suggest their respective functions to the user. For example, arrows pointing left may suggest playing the images in reverse chronological order or backwards, while arrows pointing right may be used for playing the images in chronological order or forwards.

During annotate mode 1304 the user may perform annotations on a frozen image. The user may be given the option to place any number of annotations anywhere on the image and may be free to choose the type of annotation and its text. In an embodiment the annotations may be of a text type and/or image type, for example. Some annotations may automatically appear on an image, where the annotations are specific to the type of image or type of data collected. There may be annotation text boxes that automatically appear on the image for the user to fill in, such as one for the patients name or weight. Annotate mode 1304 may include a feature that allows the user to attach a voice message to an image, for example.

Measure mode 1306 allows measurements to be taken on the frozen image. Measure mode 1306 is further discussed below in conjunction with FIG. 14.

Zoom ROI mode 1308 may allow a user to select a Region Of Interest (ROI) and zoom in and out, magnifying the ROI. In some cases the ROI may be automatically selected or a product of the data acquisition process. The user may be able to perform measurements (using measure mode 1306, for example) and add annotations (using annotate mode 1304, for example) within the ROI whether or not it is enlarged while in the zoom ROI mode 1308.

Gain mode 1310 is discussed below.

As noted above, FIGS. 7–13 have modes and other features that are common to multiple display modes including gain modes, maps modes, acoustic output modes, scale modes, dynamic range modes, edge enhancement modes, line spacing and frame rate modes, frequency modes, filter modes, packet size modes, threshold modes, persistence modes, flash suppression modes, cursor modes, auto optimize modes, minimal modes, defaults, and presets.

Gain modes 702, 804, 904, 1006, 1106, and 1310 of FIGS. 7–11 and 13, respectively, are essentially the same, and allow the gain to be adjusted, thereby changing the intensity of all or part of the image and/or data. In addition to being able to adjust the overall gain, the gain of different regions of the image may be different and individually adjusted. The user may be able to choose from one or more predetermined functions and/or input one or more user defined functions that describe how the gain should vary throughout the image. The specific predefined functions describing the gain and/or the modes available for adjusting the gain that are most convenient to use may differ for different modes of operation. Consequently, which predefined functions or modes of adjusting the gain that are made most readily available or that are made available to the user may differ for different operational modes. Adjusting the gain can aid in removing edge distortions, for example. The gain settings of the different modes are set independently from one another. The gain can be automatically optimized by pressing a button or icon, for example. Alternatively, ultrasound system 100 can monitor the image being displayed and automatically update the gain optimization.

Maps modes 720, 814, and 912 of FIGS. 7–9 allow the user to set the mapping of the display pixel values to the acquired measured signal values. In the case of maps mode 720 the mapping is a gray scale, while in the case of maps modes 814 and 912 the mapping is a color assignment. The maps modes 720, 814, and 912 may allow a gray scale or color scale to be adjusted according to a function, such as a sigmoidal function. The maps modes 720, 814, and 912 are described further in conjunction with FIG. 26C.

Acoustic output modes 724, 818, and 916 of FIGS. 7–9 determine the amount of energy in and/or the frequency of the acoustic beam or pulse, which the user may control.

Dynamic range modes 722, 820, 918, 1024, 1118, and 1210 of FIGS. 7–12 are similar to compression and allow the user to choose the range of the brightnesses included in the gray scale or the range of colors used in the color assignments. In an embodiment there may be a minimum and/or maximum brightness threshold in which data and/or display pixels that would otherwise be dimmer than the threshold may be displayed unlit. In an embodiment, there may be a minimum and maximum threshold for frequency and/or wavelength in which colors of frequencies and/or wavelengths outside of the these thresholds may be displayed unlit. The compression may be nonlinear such as a logarithmic or another function. A logarithmic scale can bring out the details of the dim display pixels while also allowing the user to see the brighter display pixels. Thus using a logarithmic scale allows a larger range of transducer pixel values to be displayed on with the same range of display pixel values than were a linear scale used. In an embodiment, dynamic range modes 820, 918, 1024, 1118, and 1210 of FIGS. 8–12 can only be adjusted through the system defaults mode 406 (FIG. 4), while dynamic range mode 722 can be adjusted during B-mode 602. In an embodiment, dynamic range mode 722 can also only be adjusted during the system defaults mode 406. Alternatively, any one of, any combination of, or all of dynamic range modes 720, 820, 918, 1024, 1118, and 1210 of FIGS. 8–12 can be adjusted during their respective mode of operation and/or during system defaults mode 406.

Auto optimize modes 725, 819, 917, 1016, 1114, and 1209 of FIGS. 7–12 automatically optimize the display to make it easier to read. Auto optimize may include optimizing any one of, all of, or any combination of the gain, contrast, compression maps, adjusting the position of the image on the screen, edge enhancement, persistence, flash suppression, and/or baseline shift, for example. The optimization is activated by the user pushing a button and/or selecting a menu item and/or icon. The user may choose settings to determine how the optimization is performed. The display image may be monitored and either automatically update the settings to optimize the image or alert the user that an optimization may improve the viewing. An example of an auto optimization for a map may be that a gray scale is automatically selected for the display pixels such that the highest signal values of the transducer pixels are displayed using highest display pixel values. Another example of an auto optimization is automatically setting the dynamic range the display pixel values to span the range of transducer pixel signal values between an average maximum value and a minimum value, thereby filtering out noise and high intensity artifacts.

Edge enhancement modes 728, 826, 924, 1028, 1122, and 1212 of FIGS. 7–12 filter out noise at the edge of the image. Edge enhancement modes 728, 826, 924, 1028, 1122, and 1212 may include different temporal and/or other filters. Edge enhancement modes 728, 826, 924, 1028, 1122, and 1212 may show the first derivative of the image to aid in finding the edges of the image, and then perform filtering along the edge to bring out various details. Edge enhancement modes 728, 826, 924, 1028, 1122, and 1212 may include a filter that smoothes spikes in the data at the edges by, for example, averaging each point along or near the edge with neighboring points or removing points with values over a given threshold. In an embodiment, when the image exceeds the available display area or as a by product of performing Fourier transforms on the image data (which is typically not periodic) and of the periodicity of Fourier transforms, the image "spills" over and overlays its own opposite edge. This "spilling" creates noise or a misaligned image. Edge enhancement mode may be used to eliminate or reduce noise or misalignment.

Line spacing and frame rate modes 730, 830 and 928 of FIGS. 7–9 control the resolution by controlling the number of lines displayed on the ultrasound system 100's screen. Line spacing and frame rate modes 730, 830 and 928 may allow adjustments to the frame rate or adjusting the frame rate may be its own mode.

Persistence modes 736, 832 and 930 of FIGS. 7–9 determine a weighting factor of the previous image to the new image information while viewing data. An image having a ¹⁄₁₀th persistence could be composed of a weighted average consisting of 9/10th the image just displayed and 1/10th the new image. Alternatively, persistence could be defined to be an equally weighted average of the last several images. For a 1/10th persistence each image is an average of the previous 10 sets of image information. A 1/10th persistence means that it takes roughly 10 new images to remove the first image. Persistence modes 736, 832, and 930 have the effect of filtering out high frequency changes. In an embodiment, the weighting factors associated with the persistence is adjusted automatically and/or dynamically. The user may be able set the weighting factors and/or parameters related to criteria for automatically choosing the weighting factors.

In FIGS. 7–12 the various modes may be grouped into boxes labeled minimal modes 738, 836, 934, 1030, 1124, and 1214, factory defaults 740, 838, 936, 1032, 1126, and 1216, and image presets 742, 840, 938, 1034, 1128, and 1218. However, none of, any one of, some of, or all of the modes of ultrasound system 100 could be grouped in any of these boxes. In an embodiment, modes in the boxes minimal modes 738, 836, 934, 1030, 1124, and/or 1214 are the minimal modes that are presented to the user at anytime during the imaging mode of FIGS. 7–12, respectively. For example, in an embodiment, when in B-mode 602 (FIG. 7) gain mode 702 and depth mode 704 in the box minimal modes 738 are always made available for the user to select. In an embodiment, modes in the boxes factory defaults 740, 838, 936, 1032, 1126, and/or 1216 may be set with initial default values by the manufacturer. Similarly, in an embodiment, modes in the boxes image presets 742, 840, 938, 1034, 1128, and 1218 may be preset and/or adjustable only during assign presets mode 404 (FIG. 4).

ROI modes 802 and 902 allow the user to choose a region of interest in which to perform a color flow study or a power Doppler study.

Scale modes 806, 906, 1004, and 1104 of FIGS. 8–11 allow the user to select the scale for representing Doppler information, such as velocity, power, and/or variance. Setting the lower limit of the scale is directly related to the selection of a "wall filter." The "wall filter" is a high pass filter, which filters out the slow motion of the blood vessel wall. The high pass filtering can be implemented by Fourier transforming or otherwise spectrum analyzing the data and locating the low frequency spike that corresponds to the slow motion of the blood vessel walls. The low frequency spike can then be removed. For example, all data below a cutoff frequency could be removed from the image, and the low frequency spike could be used to determine the cutoff frequency. In an alternative embodiment, the contribution to the data from the slow motion of the blood vessel could be removed by subtracting the expected contribution of the slow motion blood vessel from the data. In an embodiment, the slow motion may be extracted and viewed separately from the faster moving phenomenon. Optionally, each point on the image may be displayed in a different color according the velocity of the part of the medium under investigation represented. Any given user may be accustomed to, or have preference for, a different color map velocity scale (i.e., a different mapping associating each velocity with a particular color). Scale modes 806, 906, 1004, and 1104 may allow the user to determine the color map velocity scale, which the user can adjust during this mode.

Baseline modes 816, 914, and 1012 allow the user to adjust where the baseline of a plot is located. If the baseline is too high up on the screen, the top of the plot will ("wrap around" or "fold" to the bottom of the plot or will) be cut off and may appear at the bottom of the plot. In another embodiment, when the baseline is too high the top of the signal may be cut without appearing at the bottom of the plot. Baseline mode 816, 914, and 1012 may allow the user to adjust the position of the baseline on the plot by, for example, dragging and dropping the baseline using the cursor.

Packet size modes 822 and 920 of FIGS. 8 and 9 determine the number of pulses per cycle (i.e., flow count samples) emitted by the transducer, which are used to measure the velocity of the flow. Each point of the medium under investigation may have a different velocity. The collection of velocity vectors describing the flow within the medium under investigation form a vector field (i.e., a velocity field). Packet size is the count of flow samples used to determine the velocity field of the flow. The higher the count, the better the estimation of the flow's velocity field, but the slower the frame rate. The user may be allowed to adjust the flow count samples to control the accuracy and/or resolution of the velocity flow measurement.

Threshold modes 824 and 922 of FIGS. 8 and 9 are used to determine the various thresholds and/or flow threshold, which is a multi-parameter criterion used to indicate the presence or the absence of color flow. Typical parameters of the flow threshold are velocity, uncertainty or variance of the velocity, intensity, and evolution in time (i.e., the difference between display or transducer pixel values of two successive frames for the same display or transducer pixel). Threshold modes 824 and 922 of FIGS. 8 and 9 may set the thresholds for not displaying a display pixel because the display pixel or its corresponding transducer pixels are too dim or too uncertain. For example, when a signal is received, if its voltage or velocity is below a threshold, its uncertainty or variance is greater than a threshold, the amount of change in its transducer or display pixels is greater than a certain threshold, or its width (i.e., its energy) is below a threshold, then the signal is not displayed. Alternatively rather than having separate thresholds for each parameter such as voltage, velocity, energy, variance, and/or evolution in time a single threshold could be used for a function of any combination of or all of the parameters of the threshold criteria. These thresholds or others may be used in masks associated with filters of filter modes 1026 and 1120, described below or other filters.

Frequency modes 708, 828 and 926 of FIGS. 8 and 9 are used for selecting the frequency of the transducer. Frequency modes 828 and 926 are used for color data acquisition. The transducer frequency may depend upon the characteristics of the transducer selected (the system may allow the user to change transducers) and the depth into the medium under investigation desired for imaging. Lower frequencies are used for imaging deeper into the medium under investigation. Conversely, higher frequencies are used for imaging to a shallow depth in the medium under investigation. Frequency modes 828 and 926 may be independent from frequency mode 708. Frequency mode 708 may allow for selecting the frequency used for acquiring B-mode images independently of the frequency used in frequency modes 828. Alternatively, the frequency chosen by frequency mode 708 may be linked to the frequency used in frequency modes 828 and 926. The frequency of one of these modes may be automatically altered to be the same as or a function of the frequency of one or both of the other two frequency modes. Similarly, frequency modes 828 and 926 may be independent or linked to one another.

Flash suppression modes 834 and 932 filter out high frequency noise, which has a tendency of causing a flash to be displayed. The flash suppression could be accomplished with a low pass filter having a high cutoff frequency so as to pass most of the frequency spectrum. In an embodiment, flash suppression modes 834 and 932 can only be adjusted through the system defaults mode 406 (FIG. 4). Alternatively, flash suppression modes 834 and 932 can also be adjusted during their respective imaging modes.

Figure 26A:
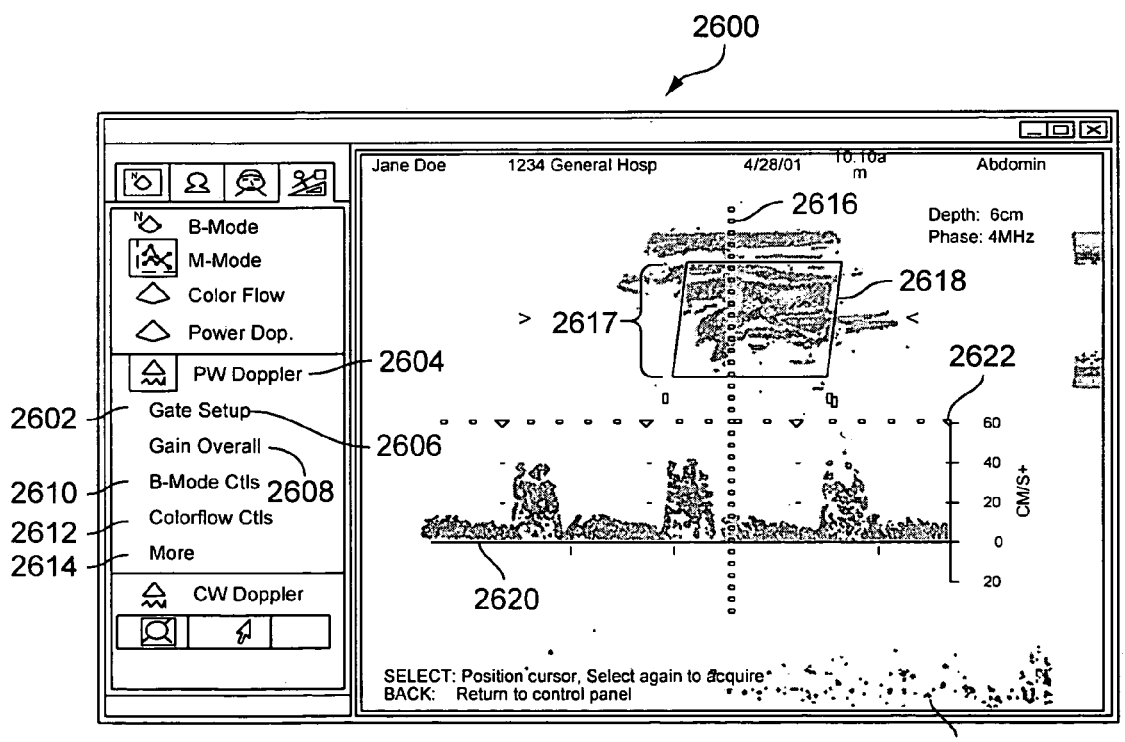
FIG. 26A shows a view having a PW Doppler control panel.

Cursor modes 1002, 1102, and 1202 determine the cursor used to indicate the region on a B-mode image that a set of data from a point (e.g., PW Doppler and CW Doppler data) or strip is being taken. For example, the cursor may be used to outline and thereby create an ROI or to size an ROI. The cursor may be used to draw an additional line along which Doppler data is taken. The portion of the line that is within the ROI may be the portion of the line used for collecting the Doppler data. Alternatively, positioning the cursor over a point of the ultrasound image, and then clicking on that point may cause the ultrasound system 100 to gather and/or display Doppler data at the corresponding point of the medium under investigation. The cursor may be used to position and/or select annotations, graphs, the axis of a graph, and/or to change the range of the scale of an axis. Cursor modes 1002, 1102, and 1202 may be used in combination with measure and annotate mode 312, discussed further below (FIG. 15) and/or with freeze mode 614 (FIGS. 6, 13 and 14), to define the ROI or trace or in combination with annotate mode 1304 (FIG. 13), for example. An example of a trace and ROI are illustrated in FIG. 26A and is discussed below. The cursor may differ according to the mode.

In addition to cursor's positioning and selecting functions, the cursor is an active GUI object used to communicate a message to the user through the cursor shape and color, for example. An example of a cursor shape is that of an arrow. If the cursor shape is an arrow, then when the location of the cursor is a valid location, e.g., within an ROI, its color may be green. Outside the ROI the cursor color may be red. Other cursor shapes may be used for other types of messages. For example, a) an hour glass may be used to tell the user that the system is busy, b) a question mark may be used to indicate that a help function is available for a particular area of the screen or screen object, c) a stop sign may be used to indicate that by selecting that position the user can cancel an ongoing operation.

This list is not a limitation of the invention. Other cursor shapes and colors may be used to communicate context dependent availability of functions and messages.

Display format modes 1008, 1108, and 1206 allow the user to arrange the determine which plots are displayed during PW Doppler mode 608, CW Doppler mode 610, and M-mode 612, respectively, and where on the screen each plot should appear. Display format modes 1008, 1108, and 1206 may also allow the user to format the individual plots and to choose the type of plot used to show the data.

Update on/off modes 1018 and 1116 automatically refresh and/or update their respective images when update on/off modes 1018 and 1116 are on, but do not when update on/off modes 1018 and 1116 are off. In an embodiment update on/off modes 1018 and 1116 only affect their respective imaging modes (i.e., update on/off mode 1010 affects only PW Doppler mode imaging update on/off mode 1116 affects only B-mode or CW Doppler imaging). In another embodiment update on/off modes 1018 and 1116 affect any one of, any combination of or all of the imaging modes individually or as one or more groups of modes. In an embodiment, update on/off modes 1018 and 1116 may turn on and/or off a simultaneous updating of the B-Mode image while Doppler information is being processed. Although updating the B-mode imaging may aid in visualizing and/or understanding the region of interest where the PW Doppler or CW Doppler information is collected, it also decreases the speed of PW or CW processing. Consequently, update on/off mode 1018 and 1116 may allow the user to choose between the added Doppler information or faster processing of CW or PW information.

Sweep speed modes 1022, 1112, and 1208 controls the speed at which the signal sweeps across the screen and/or the speed of scanning the medium under investigation.

Filter modes 1026 and 1120 allow the user to apply various filters either during data acquisition and/or while viewing the data. For example, filters that smooth the data, high pass, low pass, and notch filters may be used to filter out noise or data that is not of interest. Filter modes 1026 and 1120 may also allow the application of and/or the setting of filters of an edge enhancement mode such as edge enhancement modes 728, 826, 924, 1028, 1122, and 1212.

One form of filter that may be provided in filter modes 1026 and 1120 is a series of three masks. The first mask filters out any display pixel elements associated with one or more parameters (e.g., energy, velocity, voltage, and/or one over the variance) below a certain threshold. For example, a 1 is assigned to the display pixels that are above the threshold, and a 0 to display pixels below the threshold. The second mask is the first mask after smoothing (e.g., averaging the product of each display pixel value and its 1 or 0 with that of its nearest neighbor display pixels). The third mask is the second mask with all elements having values below a certain threshold removed. The difference between the first mask and the third mask gives the high frequency elements that changed values as a result of the extra smoothing and masking in producing the third mask. For example, a 1 is assigned to the display pixels that are above the threshold and not removed, and a 0 to display pixels below the threshold that were removed. Then the raw velocity values are assigned to those display pixels that are in both the first and third mask, while a smoothed velocity value is assigned to those display pixels that were in the first mask, but not the third mask. The smoothed velocity value associated with a display pixel may be the average of the raw velocity value of that pixel and the velocity values of the nearest neighbor display pixels, for example.

Using these three filters it is possible to produce a more accurate image of a region having both high frequency spectral components (e.g., blood flow) and low frequency spectral components (e.g. organ or blood vessel movement). The user may be presented with options to choose the thresholds associated with these masks in the filter modes 1026 and 1120 and/or in the threshold modes 824 and 922 and/or whether or not to use such a filtering technique. In an embodiment, filter modes 1026 and 1120 can only be adjusted through the system defaults mode 406 (FIG. 4). Alternatively, filter modes 1026 and 1120 can also be adjusted during their respective imaging modes.

Figure 14:
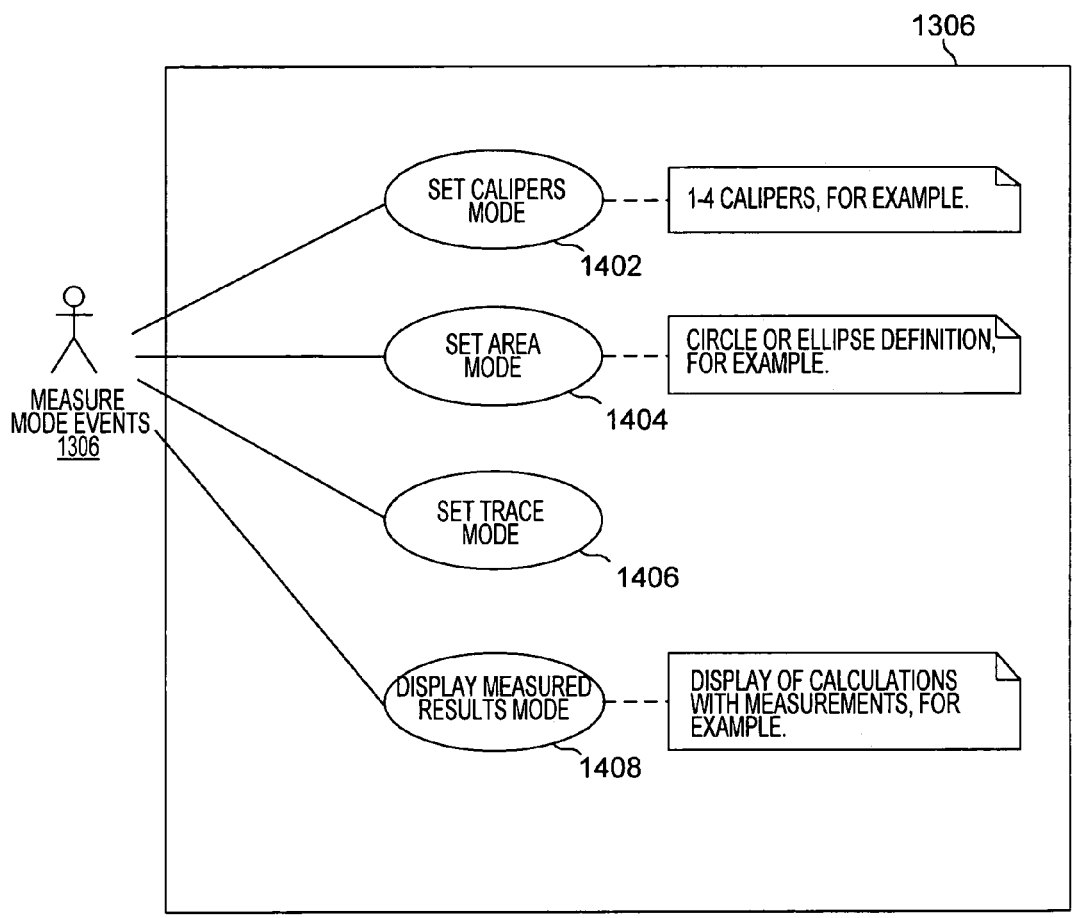
FIG. 14 shows the measure mode of the ultrasound system.

FIG. 14 shows the measure mode 1306 of the ultrasound system 100, having a set calipers mode 1402, a set area mode 1404, a set trace mode 1406, and a display measured results mode 1408.

The set calipers mode 1402 may include several different types of calipers for performing measurements of distance, velocity, frequency, and time, for example. Also, set area mode 1404 may include defining areas of different set shapes such as circles, ellipses, squares, rectangles, triangles, and/or polygons that the user may choose from. Set area mode 1404 may include tools for defining arbitrary areas such as with a real or virtual stylus or by using combinations of arcs, curvilinear lines, and straight lines. Set trace mode 1406 allows the user to determine an arbitrary trace along which a measurement might be made. Display measured results mode 1408 allows the user to display the results of one or more calculations in tabular and/or graphical format and/or as annotations on an image, for example. The user may be able to customize the tabular format or graphical format as desired.

Figure 15:
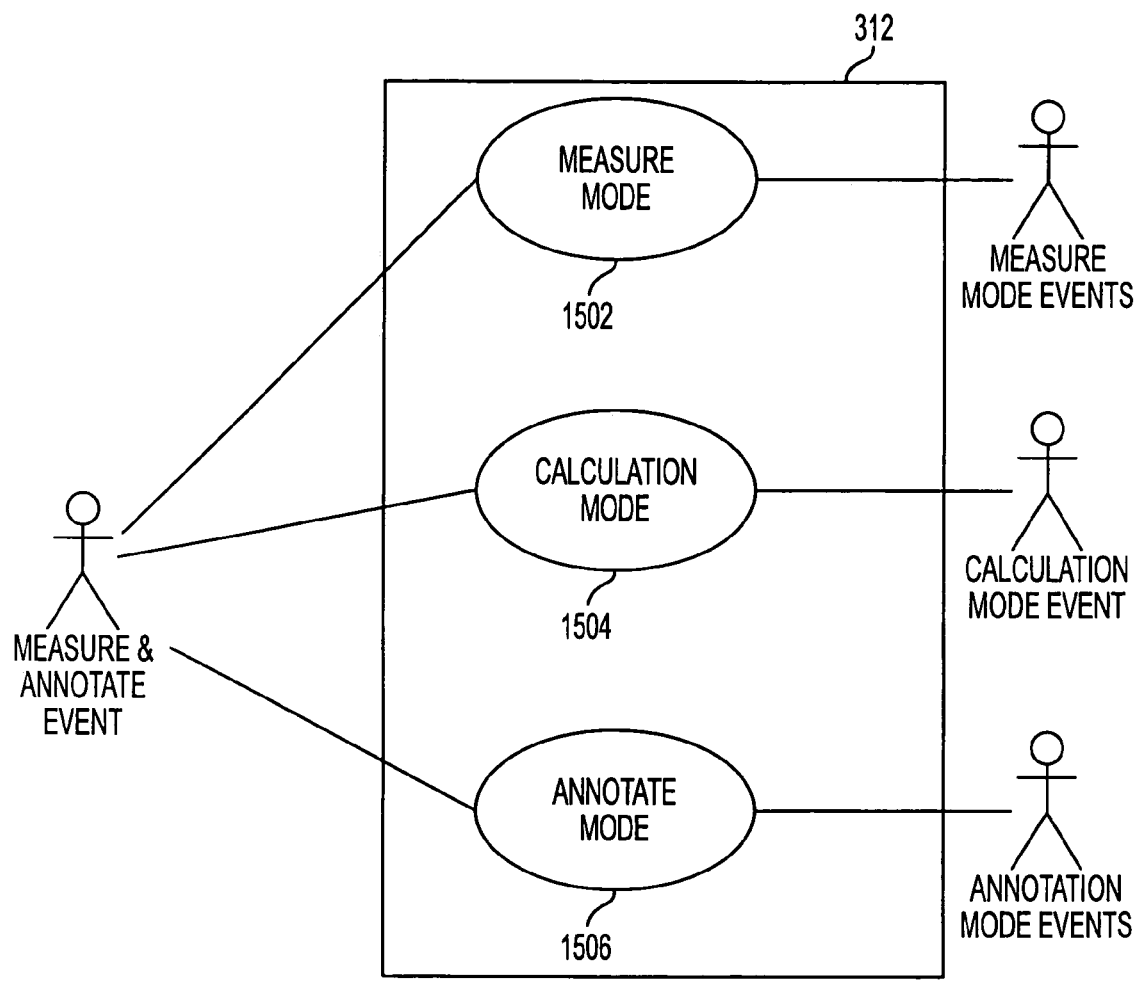
FIG. 15 shows the measure and annotate mode of the ultrasound system.

FIG. 15 shows the measure and annotate mode 312 of the ultrasound system 100, having a measure mode 1502 for taking measurements on an image, a calculation mode 1504 for calculating various parameters that can be derived from the data such as those used for diagnosing a patient, and an annotate mode 1506 for recording user input information.

Measure mode 1502 performs the measurements described above in connection with FIGS. 13 and 14 regarding measurement done on a frozen image. The difference between the measurements and annotations of FIGS. 13 and 14 and that of FIG. 15 is the path taken to get there, and that the measurements of FIGS. 13 and 14 may be taken during data acquisition. In FIGS. 13 and 14, the user first decided to freeze the image by entering freeze mode 614 (possibly while taking data) and then afterwards decided to take measurements on it. In contrast, in FIG. 15 the user first decided to take measurements in measure and annotate mode 312 on images already acquired. For example, after the images were acquired, possibly by a technician, the images may have been stored away without being further analyzed by a physician. Then, at a later time, the stored images may be displayed on the screen for analysis by the physician. The physician may use the measure mode 1502 to measure distances between or sizes of objects, for example.

Calculation mode 1504 will be further described in connection with FIG. 16. Annotation mode 1506 is the same as annotate mode 1304 describe in conjunction with FIG. 13.

Figure 16:
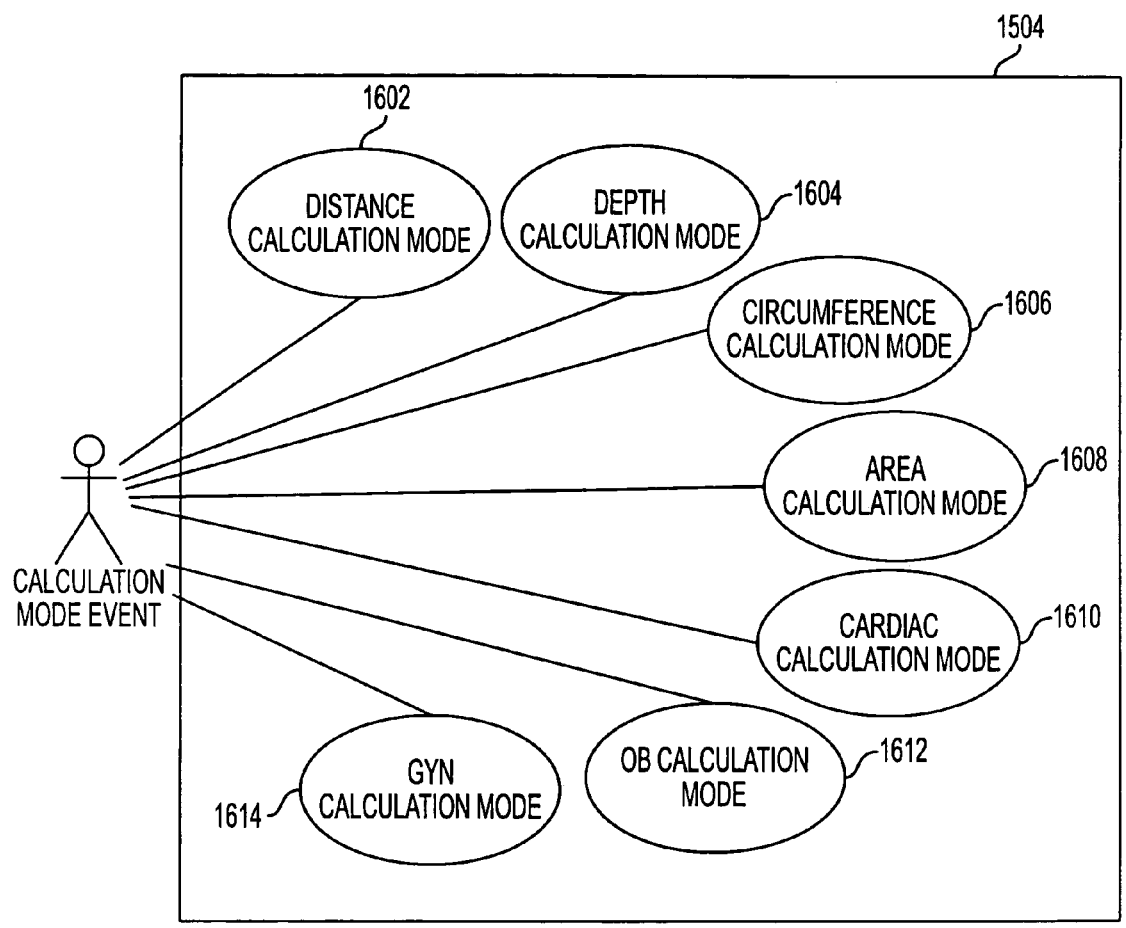
FIG. 16 shows the calculation mode of the ultrasound system.

FIG. 16 shows the calculation mode 1504 of the ultrasound system 100, having distance calculations mode 1602, depth calculation mode 1604, circumference calculation mode 1606, area calculation mode 1608, cardiac calculation mode 1610, OB calculations 1612, and GYN calculations 1614.

Distance calculations mode 1602, depth calculation mode 1604, circumference calculation mode 1606, and area calculation mode 1608 are used for calculating the distance, depth, circumference, and area, respectively, of a medium under investigation. Cardiac calculation mode 1610, OB calculation mode 1612, and GYN calculation mode 1614 are used for making calculations commonly made for cardiac, obstetric, and gynecologic examinations, respectively. The user may choose from a predetermined list of calculations to perform. Some calculations may be preformed automatically upon entering the specific type of calculation mode. Calculation mode 1504 is not limited to the specific set of calculation modes listed. Any combination of, any one of, all of and/or other specialized calculation modes may be included in the calculation mode 1504.

Figure 17:
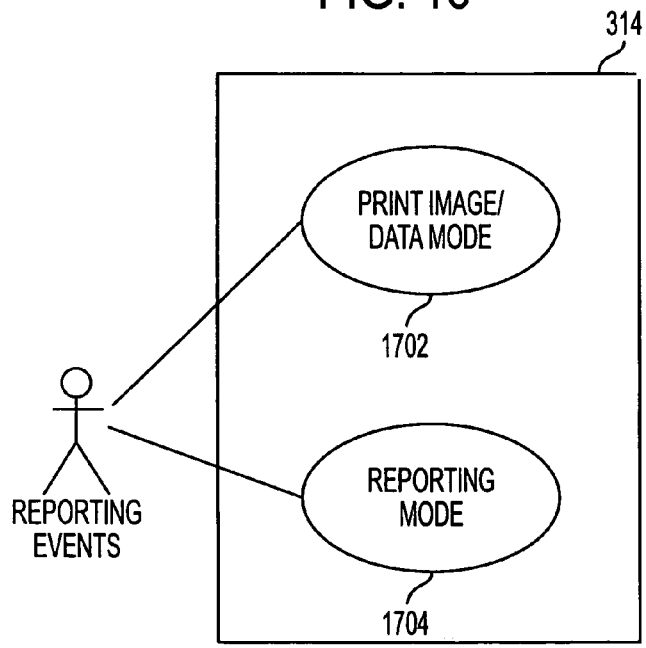
FIG. 17 shows the reporting mode of the ultrasound system.

FIG. 17 shows the reporting mode 314 of the ultrasound system 100, having print image/data mode 1702 and reporting mode 1704.

Print image/data mode 1702 may cause an image and/or a set of data to be printed to a file and/or printer. The image and/or data may be downloaded to the printer and/or a server via a cable, and/or acoustical and/or electromagnetic waves traveling through air, for example. Reporting mode 1704 may automatically generate a completed insurance form or other type of report. Reporting mode 1704 may allow the user to choose the form of the report and may have word processing capabilities, which may be specialized for producing forms.

Figure 18:
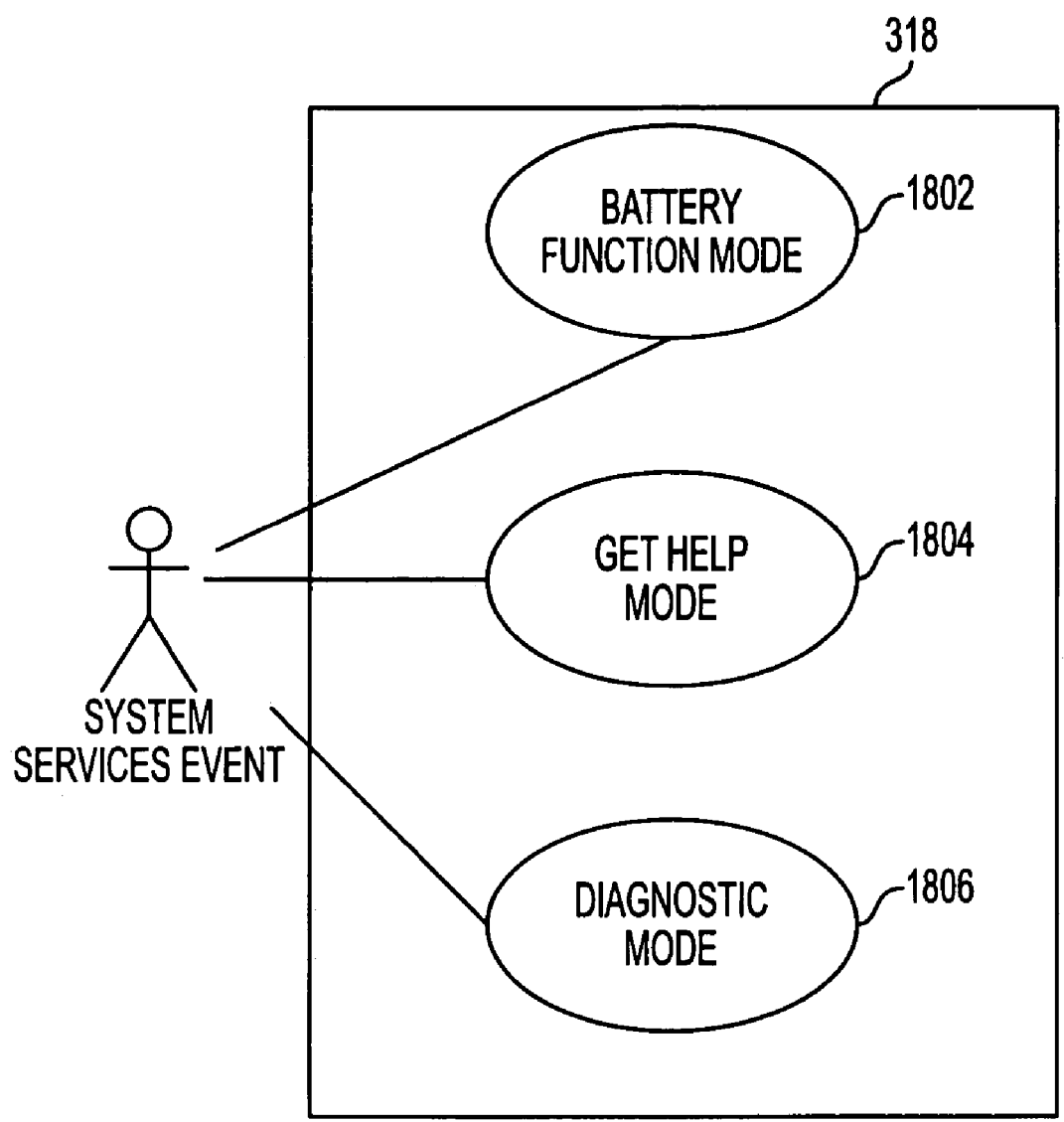
FIG. 18 shows the system services mode of the ultrasound system.

FIG. 18 shows a system services mode 318 of the ultrasound system 100, having battery function mode 1802, get help mode 1804, and diagnostic mode 1806.

Battery function mode 1802 may be the same as battery function mode 414, which may be accessible by either first entering system configuration mode 304 or by entering system services mode 318.

The get help mode 1804 generally provides the user with information about ultrasound system 100. The get help mode 1804 may be context sensitive. Get help mode 1804 may include producing call out balloons that indicate the function of a given icon, tab, and/or menu item. The user may also be able to access general help about using ultrasound system 100 that is not dependent upon the context. Get help mode 1804 may allow the user to keyword search and/or display pages and/or sections from a user's manual, for example. In an embodiment, get help mode 1804 provides an index to the user's manual. Get help mode 1804 may be capable of interactively stepping the user through a procedure as the procedure is being performed. After each step the user performs, get help mode 1804 may provide the next step in the procedure automatically.

Diagnostic mode 1806 performs diagnostics on the system and/or any one of, any combination of, or all of the components of ultrasound system 100 individually or collectively. For example, diagnostic mode 1806 may indicate if a component such as the transducer system 110 is disconnected or malfunctioning. In an embodiment, diagnostic mode 1806 may provide information about the capacity of the various components associated with configuration of ultrasound system 100 in use, such as how much memory is available or how many images can be stored. Diagnostic mode 1806 may perform signal analysis to determine whether the transducer system 110 is or other components are properly functioning. Diagnostic mode 1806 may have the capability to determine whether the transducer system 110 is operating at an appropriate frequency.

Figure 19:
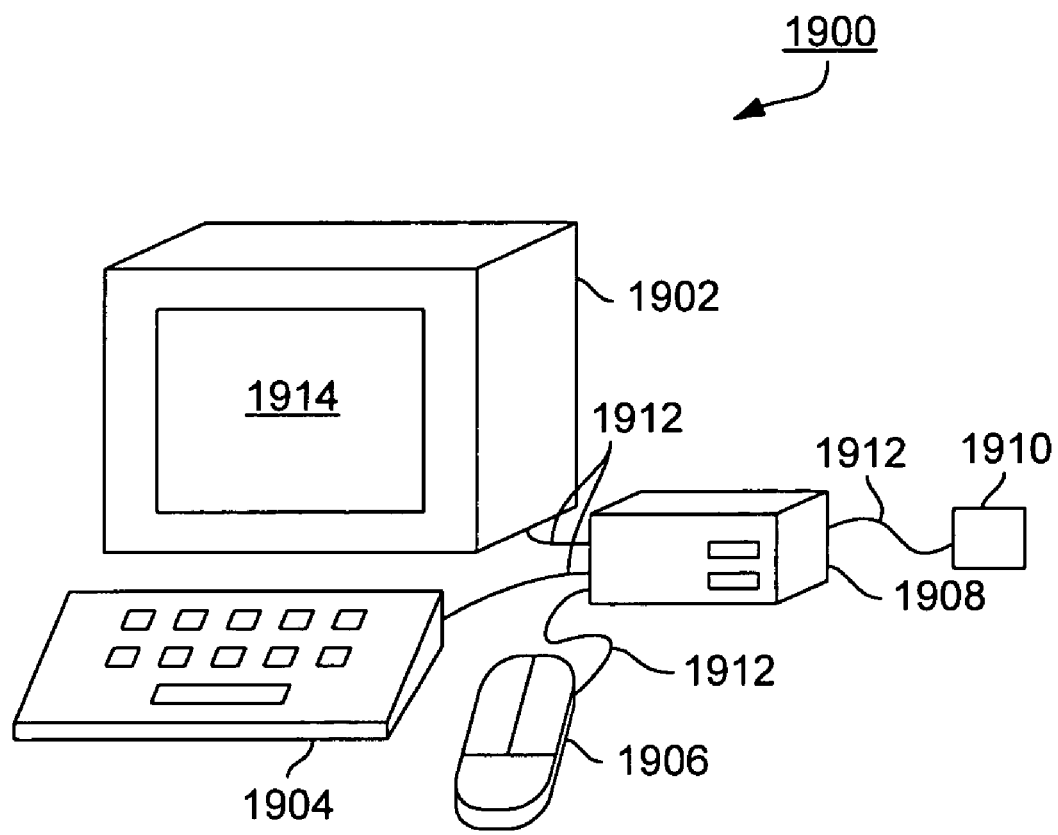
FIG. 19 shows an overview of an embodiment of the ultrasound system.

FIG. 19 shows an embodiment 1900 of the ultrasound system 100 having monitor 1902, keyboard 1904, mouse 1906, computing system 1908, transducer system 1910 and cables 1912. Monitor 1902 has screen 1914, which may be touch sensitive or may be just for viewing.

Transducer system 1910 includes an imaging ultrasound scan head having an array of transducer pixel elements used to transmit ultrasound signals for data acquisition. Transducer system 1910 converts electrical signals into acoustic signals and acoustic singals into electric signals, for the purpose of transmitting and receiving the ultrasound information.

Computing system 1908 may be responsible for setting up, processing, storing, and annotating information gathered from the transducer system 1910. The function of computing system 1908 may include image reconstruction, color flow estimation, and Doppler computations, for example. Computing system 1908 may include laptop computer, a Personal Computer (PC) or be capable of performing many of or all of the functions associated with a PC or laptop computer. Computing system 1908 may have an interface for transferring data to and/or from another system.

Computing system 1908 and/or transducer system 1910 processes the data collected and converts it into a format to be displayed on screen 1914 of monitor 1902. Computing system 1908 and/or transducer system 1910 is responsible for collecting and digitizing ultrasound data. Computing system 1908 and/or transducer system 1910 also produces the signals to control and/or drive the transducers of the transducer array of transducer system 1910.

The user interactions with computing system 1908 and/or transducer system 1910 may be through buttons and/or keys of keyboard 1904, mouse 1906, and/or touch sensitive control areas on screen 1914.

In an embodiment, screen 1914 may contain a representation of mouse 1906, buttons and/or keys of keyboards 1904, and/or of other buttons and/or control elements that can be activated by touching screen 1914. The buttons and/or keys represented on screen 1914 may additionally or alternatively be activated by using mouse 1906 or direction keys and an enter key of key board 1904 to navigate a cursor and/or an indication of a selection. Having a representation of mouse 1906, buttons, and/or keys on screen 1914 may be useful for navigating GUI 208 and/or the ultrasound image when the image is presented on an external video monitor. Screen 1914 displays GUI 208, which may have views of fixed formats and/or may give the user the option to retile or rearrange the windows of the GUI 208 on screen 1914 in any fashion desired.

The keys and/or buttons of keyboard 1904, GUI 208 and/or the cursor of mouse 1906 may be intelligent and interactive and may change their function according to the context, history, and/or state of embodiment 1900.

Transducer system 1910, computer system 1908, and/or monitor 1902 may be battery-operated.

Embodiment 1900 may have one or more on/off switches and/or one or more microphones as one or more separate stand alone units and/or incorporated in any one, any combination of, or all of, computing system 1908, transducer system 1910, monitor 1902, keyboard 1904, and/or mouse 1906. The microphone may be used for voice activation of all of or any part of GUI 208 to control embodiment 1900.

If monitor 1902 is not touch sensitive, then monitor 1902 part of output system 102 (FIG. 1). If monitor 1902 is touch sensitive, then monitor 1902 is part of input/output system 114 (FIG. 1). Keyboard 1904 and mouse 1906 are part of input system 104 (FIG. 1), and are used to input text and/or select menu items, icons, virtual tabs and/or virtual buttons, for example. Computing system 1908 includes processing system 108 and memory system 106 (FIG. 1). Transducer system 1910 is part of transducer system 110, and is used for transmitting ultrasound signals to a medium under investigation such as a human body.

Cables 1912 are an embodiment of communications system 112. Cables 1912 communicatively link transducer system 1910, keyboard 1904, monitor 1902, computing system 1908, and mouse 1906. Cables 1912 may be wires and/or fiber optic cables, for example. Alternatively, transducer system 1910, keyboard 1904, monitor 1902, computing system 1908, and/or mouse 1906 may be communicatively linked without cables by using radio waves, for example.

Keyboard 1904 will be discussed further after the discussion of FIG. 21.

Figure 20:
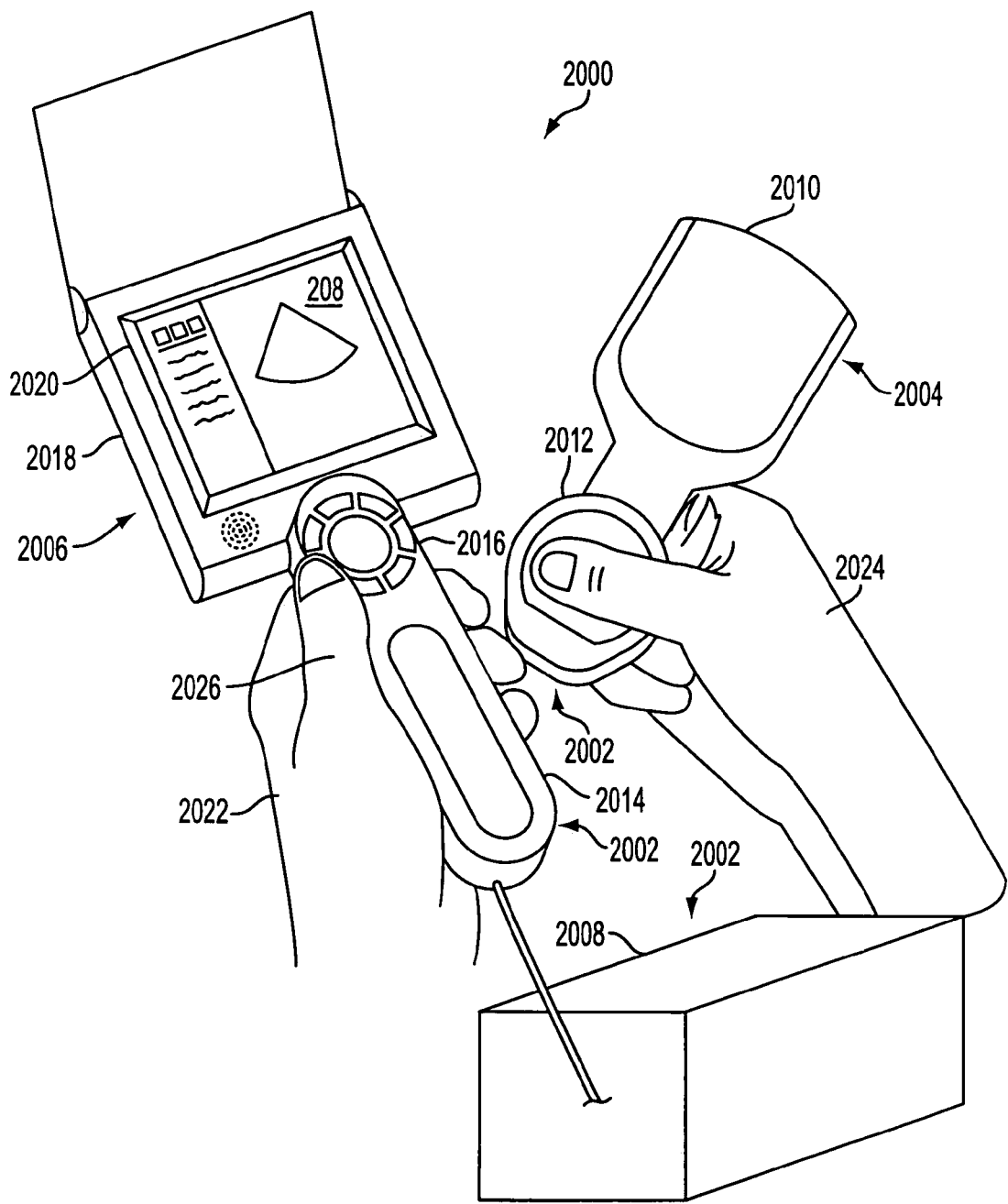
FIG. 20 shows an operation mode of an embodiment of the ultrasound system.

FIG. 20 shows an operation mode 2000 for system 2002, which is of an embodiment of the ultrasound system 100. Ultrasound system 100 has imaging unit 2004, display and control unit 2006, and docking unit 2008. Imaging unit 2004 includes imaging module 2010 and transducer module 2012. Display and control unit 2006 includes two parts which are (1) handle 2014 having buttons 2016 and (2) monitor module 2018 having screen 2020 displaying GUI 208. Operation mode 2000 uses hands 2022 and 2024. Hand 2022 has thumb 2026.

Ultrasound system 100 has an operation mode 2000 of a handheld device that can be operated with either hand. Ultrasound system 100 may be any type of handheld ultrasound imaging unit, such as that of U.S. Pat. No. 6,251,073 B1. One hand 2024 holds imaging module 2010 which may include an transducer module 2012, while the other hand 2022 holds the display and control unit 2006 by handle 2014. In such a situation, where one hand 2024 is used for imaging, it is desirable for the user to be able to use the other hand 2022 to hold and/or operate the display and control unit 2006. In an embodiment, buttons 2016 are arranged on handle 2014 of display and control unit 2006 in such a fashion that thumb 2026 can conveniently operate buttons 2016. As an example of this embodiment, buttons 2016 may be arranged in a circular or symmetrical pattern. In another embodiment, buttons 2016 may be arranged in any pattern.

The display and control unit 2006 may be responsible for setting up, displaying, processing, storing, and annotating information gathered from the imaging unit 2004. The function of diplay and control unit 2006 may include image reconstruction, color flow estimation, and Doppler computations, for example. Display and control unit 2006 may include a Personal Digital Assistant (PDA) or be capable of performing many of or all of the functions associated with a PDA. Imaging unit 2004 and display and control unit 2006 may be battery-operated, and screen 2020 on display and control unit 2006 may be touch sensitive. Handle 2014 is for holding display and control unit 2006. The user interactions with display and control unit 2006 may be through buttons 2016 on handle 2014 and/or touch sensitive control areas on screen 2020. In an embodiment, handle 2014 could be replaced with a small keyboard or panel having buttons 2016. Screen 2020 displays GUI 208, which may have views of fixed formats and/or may give the user the option to retile or rearrange the windows of the GUI 208 on the screen in any fashion desired.

In an embodiment, screen 2020 may contain a representation of the buttons 2016 or of other buttons and control elements, which can be activated by touching screen 2020. Having a representation of buttons 2016 on screen 2020 may be useful for navigating GUI 208 and/or the ultrasound image when the image is presented on an external video monitor.

In addition to a location for storing imaging unit 2004, docking unit 2008 may be used for recharging imaging unit 2004 and display and control unit 2006. Alternatively, docking unit 2008 may also be used for downloading and/or uploading files to the display and control unit 2006 and/or for connecting display and control unit 2006 to a network. Alternatively, docking unit 2008 may be used for both recharging and uploading and/or downloading files. Docking unit 2008 may alternatively be used to provide video interfaces like composite/SVHS video out (NTSC/PAL) and SVGA video out for connecting to a PC monitor.

Figure 26B:
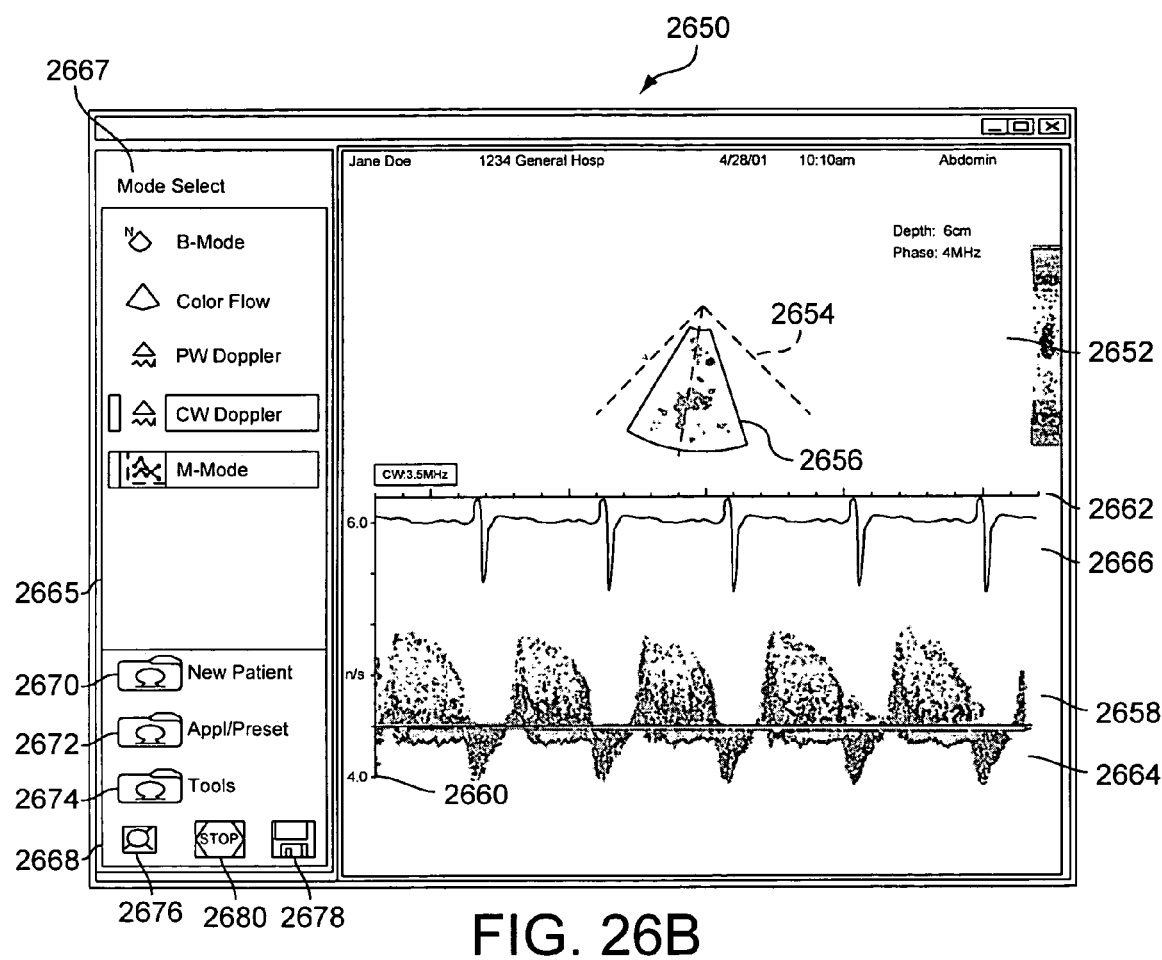
FIG. 26B shows a view having a CW Doppler control panel.

In an embodiment, docking unit 2008 may be used to input an ECG Signal displayed in FIG. 26B, Plot 2666.

Imaging module 2010 processes the data collected and converts it into a format to be displayed on screen 2020 of display and control unit 2006. Imaging module 2010 is responsible for collecting and digitizing ultrasound data. Imaging module 2010 also produces the signals to control and/or drive the transducers of the transducer array of transducer module 2012.

Transducer module 2012 includes an imaging ultrasound scan head having an array of transducer pixel elements used to transmit ultrasound signals for data acquisition. Transducer module 2012 converts electrical signals into acoustic signals and acoustic signals into electric signals, for the purpose of transmitting and receiving the ultrasound information.

Monitor module 2018 and any means, such as docking unit 2008, of outputting information to a printer on other computer is part of output system 102 (FIG. 1). Buttons 2016, screen 2020 (if touch sensitive), and any means of inputting data (e.g., patient information or images) from a computer system or database is part of input system 104 (FIG. 1). Imaging module 2610 and any processing and/or memory units with display and control unit 2006 are part of memory system 106 (FIG. 1) and processing system 108 (FIG. 1). Transducer module 2012 is part of transducer system 110 (FIG. 1). The cables and/or means for communicating through the air (using electromagnetic or sound signals) are part of communications system 112 (FIG. 1).

By placing the screen 2020 and the transducer module 2012 on separate units held in separate hands, screen 2020 can be used to view the image being scanned in real time. Placing the buttons 2016 on the same unit as the screen 2020 facilitates seeing the buttons 2016 and the screen 2020 simultaneously so that the user knows the function of button 2016 being pressed while viewing the effects of the button. Placing imaging module 2010 in the same unit as transducer module 2012 allows the signal path from imaging module 2010 to transducer module 2012 to be shorter and therefore less noisy than were imaging module 2010 and transducer module 2012 on separate units.

In one embodiment (not shown), however, the screen 2020 and buttons 2016 are located in different units. Buttons 2016 could be placed on imaging unit 2004. Imaging module 2010 and transducer module 2012 do not have to be placed in the same unit. Imaging module 2010 could be placed in the same unit with screen 2020 and buttons 2016, or could be placed with only screen 2020, while buttons 2016 are on the same unit as only transducer module 2012. Alternatively, imaging unit 2004 and display and control unit 2006 could be placed together in one unit. The invention is not limited to a handheld system. Display and control unit 2006 could be replaced with an appliance that is not handheld such as a laptop computer, personal computer, workstation, or mainframe computer, which may or may not include imaging module 2010. The appliance that is not handheld (e.g., a computer) may be programmed to perform the functions of imaging module 2010.

GUI 208 has many different views. In this specification, each view is a different combination of features, menu items, icons, and/or tabs. The word "view" is to be understood as generic to a frame or page of GUI 208.

System 2002 provides a user interface for a handheld imaging device. In order to accommodate holding and controlling the device at the same time with one hand (e.g., hand 2022), GUI 208 is designed to be used by one-hand and one-thumb operation, and makes use of several intelligent (adaptive and context sensitive) active elements, e.g., windows, soft buttons, tabs, menus, toolbars, and/or icons.

In one embodiment, GUI 208 interface is voice controlled. To facilitate use with one hand, the user can train the device to recognize a set of words or combinations of words. Each recognizable unit (word or word combination) can be assigned to a device command, performing a specific function or a sequence of functions. Thus, some or all functions can be voice activated obviating or partially obviating the use of hand controls.

Figure 21:
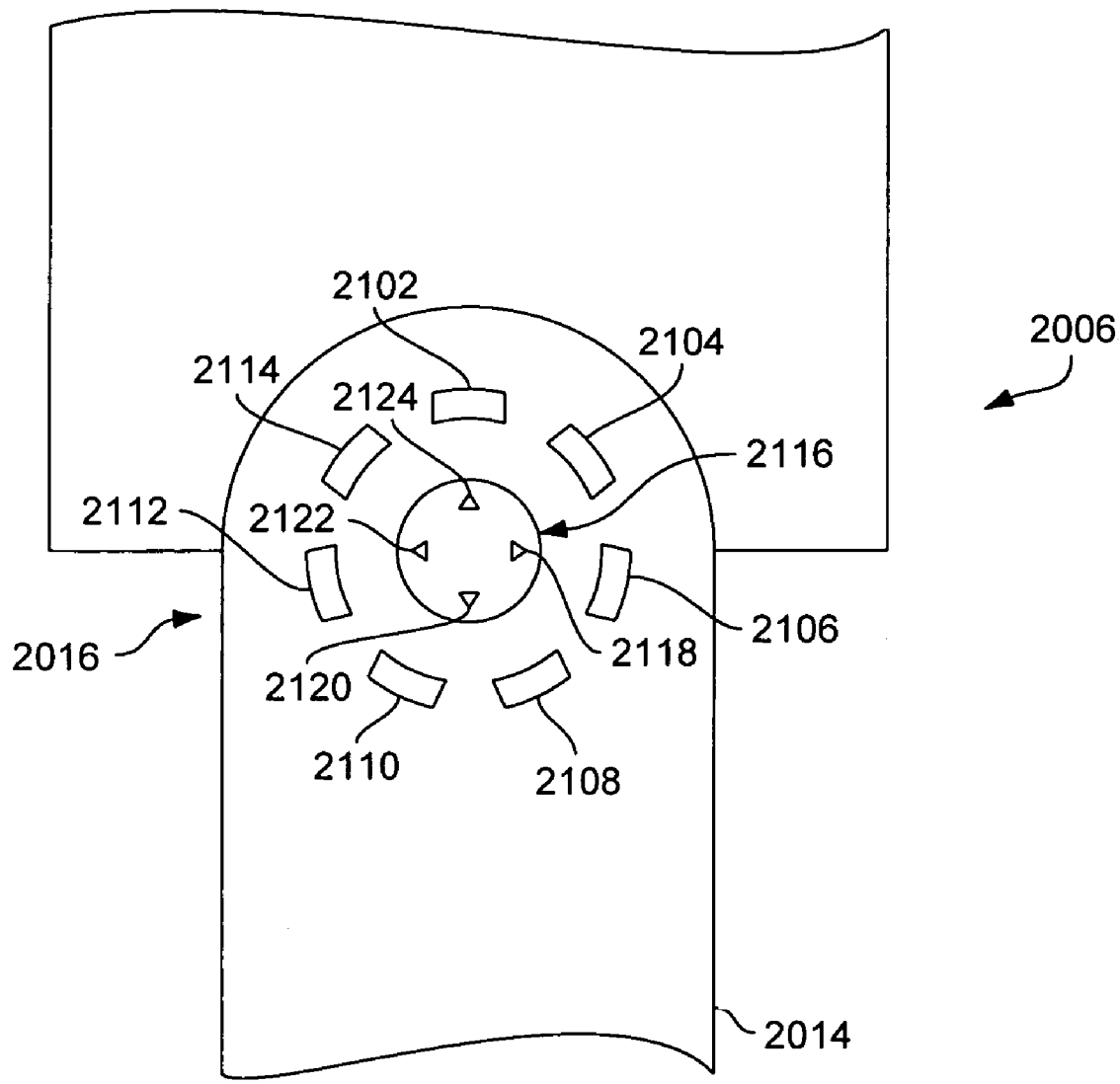
FIG. 21 shows buttons on the display and control unit of the ultrasound system.

FIG. 21 shows buttons 2016 on display and control unit 2006 of ultrasound system 100. In an embodiment, buttons 2016, which are made accessible to the user on display and control unit 2006, may include a start/stop toggle 2102, a back/escape-button 2104, a save button 2106, a first programmable button 2108, a second programmable button 2110, a print button 2112, a select or enter button 2114, and a direction button 2116. Direction button 2116 has a right arrow 2118, a down arrow 2120, a left arrow 2122 and an up arrow 2124.

The buttons and toggles may be multifunctional. For example, start/stop toggle 2102 may be replaced with or double as a freeze/unfreeze toggle. Start/stop toggle 2102 toggles between two states start and stop or freeze and unfreeze. While in or upon being placed into the start or unfreeze state a process may be activated allowed to continue to operate, or screen 2020 may be allowed continue to display a series of images. While in or being placed into the stop or freeze state a process may be stopped temporarily, shutdown, or the screen 2020 may be held frozen on one image.

Back/escape button 2104 returns screen 2020 to a prior view or frame of GUI 208 or may be configured to exit a process in progress. Save button 2106 may be configured so that it saves an image to a file or saves data (e.g., a patient's profile) that was entered, for example.

First programmable button 2108 and second programmable button 2110 can be programmed by the user to perform a user-defined function. Alternatively, the user is allowed to select a function from a list of predefined functions and assign that function to one of the programmable keys. In an embodiment, the user may be allowed to program the programmable buttons to perform any desired function and also given a list of predetermined functions to choose from that can be assigned to the programmable buttons. In another embodiment, a sequence of user actions can be recorded and allocated to a first programmable button 2108 and/or second programmable button 2110. The recorded sequence is started when the user presses the button.

Print button 2112 activates a print action. For example, print button 2112 may activate a printer to print an image or data, such as a patient profile or report. The image or data may be transmitted to the printer by electromagnetic or sound waves traveling through the air or via a cable between a printer and ultrasound system 100, for example. Select or enter button 2114 may be used to select an icon, tab, selection, or file or may be used to enter data typed in at the start of or during the operation of a routine or program. Select or enter button 2114 and the direction button 2116 may be combined into a single control element.

Direction button 2116 can be used to navigate a selection between icons, tabs, text boxes, or to move a cursor within a text box, for example. The movement direction of the cursor or the selection is determined by arrows 2118, 2120, 2122, and/or 2124. Depressing an arrow moves the cursor or selection in the direction of the arrow. Left arrow 2122 moves the cursor or selection to the left. Down arrow 2120 moves the cursor or selection down. Right arrow 2118 moves the cursor or selection to the right. Up arrow 2124 moves the cursor or selection up. Direction button 2116 can be replaced with four direction buttons—one button for each arrow 2118, 2120, 2122, and 2124. The selection and cursor movement up, down, right, and left may be actuated at a variety of speeds that may depend on the context of the action. For example, selecting menu items may be actuated at one speed, while moving a cursor may auto-repeat at continuously increasing speeds. Tactile feedback (feedback related to a person's sense of feeling) is integrated with the selection and movement, such that, for example, it may be more difficult to leave a selection than to move through different selections. In an embodiment, the time required to implement an action is used to convey a sense of the action being more difficult to implemented. By requiring a longer time to implement an action the user is, given more opportunity to change her or his mind as to whether to allow the action to be completed.

In an embodiment, any one of, any two of, or all of display and control unit 2006, imaging module 2010, and docking unit 2008 may have its own on/off button.

In an embodiment, GUI 208 provides for several buttons 2016 accessible with the thumb 2026 of hand 2022 holding display and control unit 2006. Although FIG. 21 illustrates hand 2022 as a left hand and hand 2024 as a right hand either hand could be used for hand 2022 and hand 2024. In other words, buttons 2016 may be used by and/or made to be accessible to any finger of either or both hands. The number and functions of the buttons indicated in this embodiment are for exemplification purposes and do not constitute a limitation of the invention.

Some of buttons 2016 have fixed functionality (hard buttons); i.e., buttons 2016 with fixed functionality always activate the same system function independent of the operation mode. For example, start/stop toggle 2102 (e.g., freeze/unfreeze) may have a fixed function. Other of buttons, such as buttons 2016, may be used to position a cursor on the GUI 208 in the up, down, left, and right directions, such as direction arrows 2118, 2120, 2122, and/or 2124. Select or enter button 2114 may be used to activate the object the cursor points to or to perform a certain system function in accordance to the cursor's position. At least one button, such as back/escape button 2104, may automatically or manually perform a functionality switch. Automatic functionality switches may depend system 100's state (e.g., the present mode or modes in use, the history of which modes were used most recently, how much battery lifetime remains, and/or the history of which functionality the user selected for that button). The two user programmable buttons, first programmable button 2108 and second programmable button 2110, may also be programmed to switch functions depending upon context.

An auto-optimize button and/or an on/off button may also be placed on handle 2014 or elsewhere in addition to buttons 2016 or in place of one of the buttons 2016. In an embodiment, save button 2106 could be replaced with an auto-optimize button, and print button 2112 could be replaced by a print/save button that switches function depending on the context. For example, the print button 2112 may also function as a save button during imaging modes and as a print button during cine mode 1302 (FIG. 13). Whenever the user depresses the auto optimize button, the system settings may be automatically optimized in accordance with several parameters including the system state, the image content, and the type of application.

The invention is not limited to the specific arrangement of buttons 2016 shown in FIGS. 20 and 21. In addition to the arrangement depicted in FIGS. 20 and 21, any of the buttons 2102–2114 may have any of the functions associated with any of the other buttons 2016, or functions not herein discussed. Buttons 2016 could be arranged in rows and columns and/or arranged to form any shape, such as a rectangle, triangle or oval. Buttons 2016 could be replaced with keys on a keyboard.

Returning to FIG. 19, any of one or group of keys and/or buttons of keyboard 1904 may be assigned the functions of buttons 2016. For example, keyboard 1904 may have direction arrows that perform the same functions arrows 2118, 2120, 2122, and 2124. Keyboard 1904 may have a print screen button that performs the same functions as a print/save button, as save button 2106, or print button 2112. Keyboard 1904 may have a pause button that may function as start/stop toggle 2102. Keyboard 1904 may have a backspace button and escape button, which may share the functions of back/escape button 2104. In an embodiment one or both of the backspace and escape buttons may be able to perform all of the functions of back/escape button 2104. In an embodiment, keyboard 1904 is specially designed for use with ultrasound system 100 and has buttons corresponding to buttons 2016. Keyboard 1904 may have one or more function buttons (e.g., F1–F12), any one of, any combination of or all of which may be programmable. Alternatively, any one of, any combination of or all the keys and/or buttons of keyboard 1904 may be programmable. Any of the buttons of keyboard 1904 may be assigned the auto optimize function of the auto optimize button discussed in conjunction with FIG. 21.

Although certain features and/or function of ultrasound system 100 may have been discussed in conjunction embodiment 1900 and not in conjunction with system 2002, system 2002 may also include those features and/or functions. Although certain features and/or function of ultrasound system 100 may have been discussed in conjunction system 2002 and not in conjunction with embodiment 1900, embodiment 1900 may also include those features and/or functions.

Figure 22:
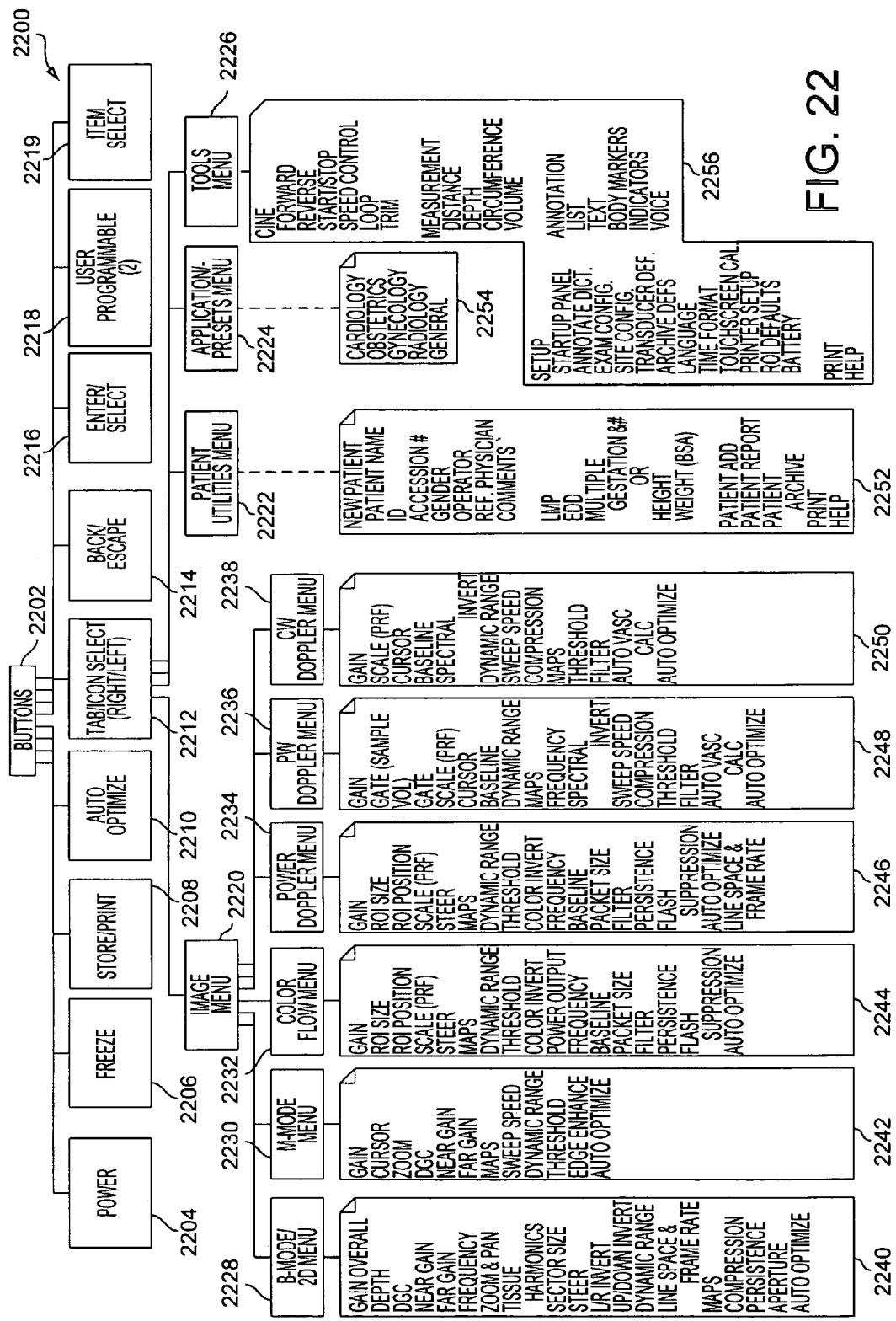
FIG. 22 shows an example of a menu tree according to the invention.

FIG. 22 shows an example of a menu tree 2200 according to the invention, having hard buttons 2202 including a power button 2204, freeze button 2206, store button 2208, auto optimize button 2210, tab/icon select sequences 2212, back/escape button 2214, enter/select button 2216, and user programmable buttons 2218, and item select button 2219. Menu tree 2200 also includes image menu 2220, patient utilities menu 2222, application presets menu 2224, and tools menu 2226. Image menu 2220 has B-mode menu 2228, M-mode menu 2230, color flow menu 2232, power Doppler menu 2234, PW Doppler menu 2236, CW Doppler menu 2238, which in turn have B-mode menu items 2240, M-mode menu items 2242, color flow menu items 2244, power Doppler menu items 2246, PW Doppler menu items 2248, and CW Doppler menu item 2250, respectively. Patient utilities menu 2222, application presets menu 2224, and tools menu 2226 include patient utilities menu items 2252, application presets menu items 2254, and tools menu items 2256, respectively.

Menu tree 2200 is an example of a menu tree for GUI 208 (FIG. 1) of ultrasound system 100 corresponding to main operational modes 300 (FIG. 3).

Hard buttons 2202 correspond to and may be identical to buttons 2016 (FIG. 20). Power button 2204 could be an on/off button. Freeze button 2206 could be start/stop toggle 2102 (FIG. 21). Store button 2208 could be save button 2106 (FIG. 21), and may also function as a print button, depending on the context. User programmable buttons 2218 could be the same first programmable button 2108 (FIG. 21) and second programmable button 2110 (FIG. 21). Enter/select button 2216 could be select or enter button 2114 (FIG. 21). Auto optimize 2210 may be the same as the optional auto optimize button that can be included in buttons 2016 and/or have the same function as nay of the auto optimize modes. Tab/icon select sequences 2212 are sequences of menu navigation operations followed by a select operation choosing a menu item. Tab/icon select sequences 2212 and/or item select button 2219 could be implemented by direction button 2116 (FIG. 21) having right arrow 2118, down arrow 2120, left arrow 2122 and up arrow 2124 for navigating through the menu items or icons on a view of the GUI 208 (FIG. 2). Back/escape button 2214 could be the same as back escape button 2104.

Among the menu items on the image menu 2220 are menu items that select B-mode menu 2228, M-mode menu 2230, color flow menu 2232, power Doppler menu 2234, PW Doppler menu 2236, and CW Doppler menu, which are different imaging modes corresponding to B-mode 602, M-mode 612, color flow mode 604, Power Doppler mode 606, PW Doppler mode 608, and CW Doppler mode 610 (FIG. 6), respectively. The different modes of the display modes of FIGS. 7–13 may have a one-to-one correspondence with the B-mode menu items 2240, M-mode menu items 2242, color flow menu items 2244, power Doppler menu items 2246, PW Doppler menu items 2248, and CW Doppler menu item 2250, respectively.

Patient utilities menu 2222 corresponds to patient information mode 306 (FIG. 3).

Cardiology, obstetrics, gynecology, and radiology menu items of application presets menu items 2254 correspond to different types of users. The menu item general may allow for individual customizing of all or some presets.

Menu items cine, annotation, and measurement of tools menu items 2256 implement cine mode 1302, annotate mode 1304, and measure mode 1306 (FIG. 13), respectively. Setup menu item of tools menu items 2256 implements parts of system configuration mode 304 (FIG. 3). Startup panel menu item corresponds to system defaults mode 406 (FIG. 4) and is used for setting the startup display. Annotate dictionary menu item corresponds to define annotation dictionary mode 408 (FIG. 4). Exam configuration menu item corresponds to assign presets mode 404 (FIG. 4). Site configuration menu item corresponds to set system defaults mode 406 (FIG. 4). Transducer defaults, archive defaults, battery, ROI defaults, and reset configuration menu items may also be included in system defaults mode 406. Language menu item corresponds to language mode 416 (FIG. 4). Touchscreen calibration corresponds to touchscreen calibration mode 410 (FIG. 4). Printer set up menu item corresponds to printer setup mode 412 (FIG. 4).

Figure 23:
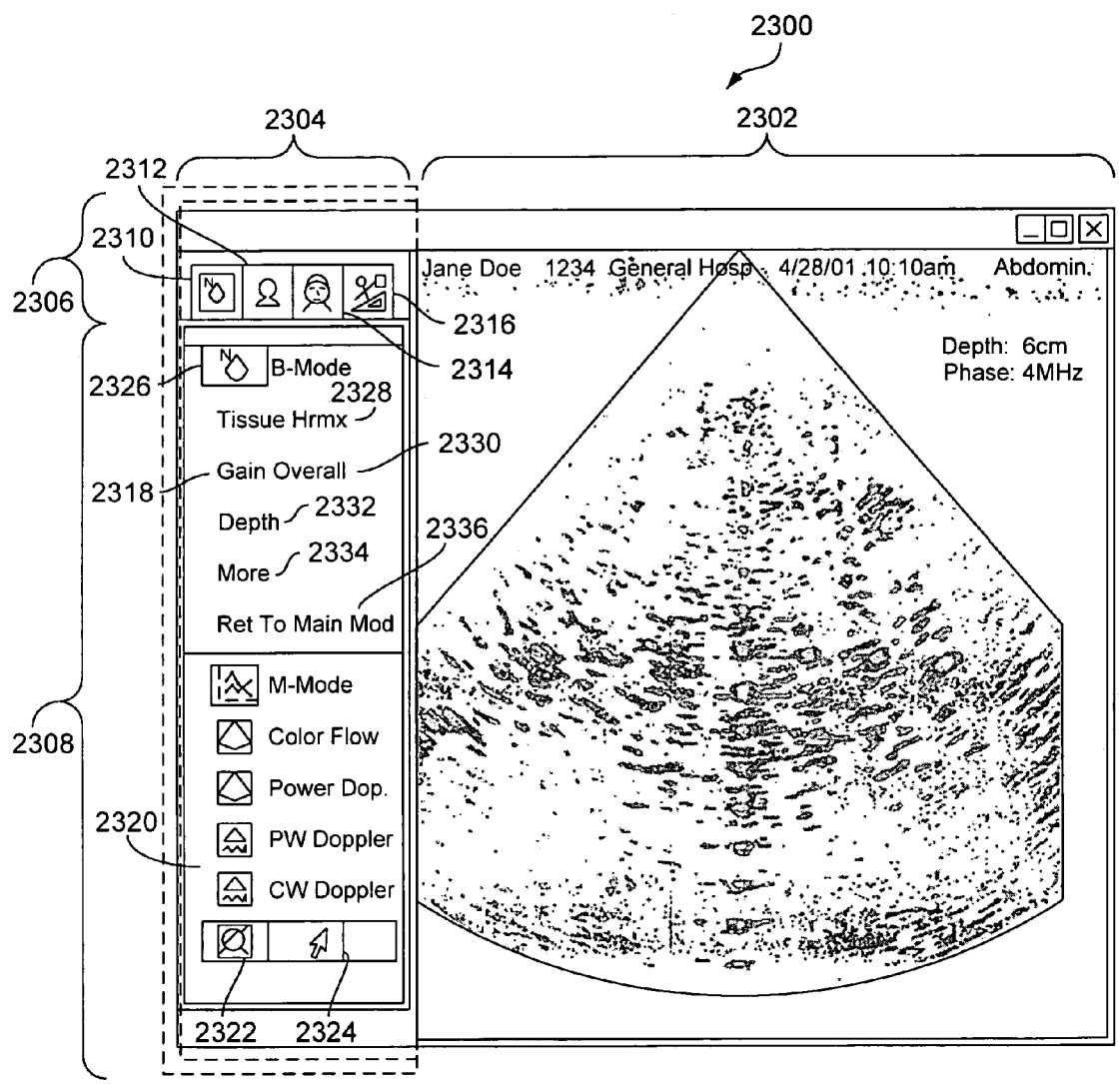
FIG. 23 shows an embodiment of a main display screen.

FIG. 23 shows an embodiment of a main display view 2300 having image area 2302, control area 2304. Control area 2304 has tabbed panel 2306 and sub-panel 2308. Tabbed panel 2306 has imaging mode tab 2310, patient information tab 2312, user defined presets tab 2314, and tools tab 2316, which correspond to the menu items 2220, 2222, 2224, and 2226 (FIG. 22), respectively. Sub-panel 2308 has a selected imaging mode panel, which is B-mode control panel 2318, a menu of imaging modes 2320, and a menu of additional functions including an audio tab 2322, and cursor tab 2324. More tabs can be added or configured by the user, such as a full screen tab. Cursor tab 2324 activates a cursor in the image area 2302. Audio tab 2322 allows messages to be recorded. Ultrasound system 100 starts in B-mode ready for imaging. Sub-panel 2308 may have a hide control button in place of or in addition to audio tab 2322, which hides the control area. B-mode control panel 2318 includes B-mode tab 2326, tissue harmonics tab 2328, gain tab 2330, depth tab 2332, more tab 2334, and return to main mode tab 2336.

In an embodiment, the modes of operation accessible via GUI 208 are divided into four main categories by imaging mode tab 2310, patient information tab 2312, user defined presets tab 2314, and tools tab 2316. In an embodiment, imaging mode tab 2310, patient information tab 2312; user defined presets tab 2314, and tools tab 2316 are accessible in every view of the control panel unless hidden by a window or in full screen mode 618 (FIG. 6), for example. Imaging mode tab 2310 allows a user to select an imaging mode and set the associated parameters. For example, a user could use imaging mode tab 2310 to select B-mode menu 2228, M-mode menu 2230, color flow menu 2232, power Doppler menu 2234, PW Doppler menu 2236, or CW Doppler menu and thereby select the corresponding imaging mode. Selecting imaging mode tab 2310 while viewing the B-mode imaging view, as in FIG. 23 would not affect a change because the default imaging view (e.g., B-mode) is already on screen 2020 or 1914. Selecting imaging mode tab 2310 while viewing an operating mode other than the default imaging mode may cause the view to change to the default imaging mode. Alternatively, selecting imaging mode tab 2310 while already viewing an imaging mode even though it is not the default imaging mode will not cause any change in the display, because GUI 208 is already presenting an imaging mode.

Patient information tab 2312 allows the user to enter patient specific data. User defined presets tab 2314 allows the user to select her or his preferences. User defined preferences may include, for example, the type of user (e.g., OB/GYN, cardiologist, or technician) the sets of measurements, calculations, and/or reports presented to the user and/or the mode of first view that appears upon powering up. Tools tab 2316 allows the user to access cine mode 1302, annotate mode 1304, measure mode 1306, and/or setup other functions. B-mode control panel 2318 includes the menu items of the imaging mode selected. Menu of imaging modes 2320 provides a menu containing menu items that are each a different display mode. Audio tab 2322 allows audio messages to be recorded and/or played back. Cursor tab 2324 activates a cursor in the image area 2302.

B-mode control panel 2318 is activated upon selecting B-mode tab. Tissue harmonics mode 706 (FIG. 7), gain mode 702 (FIG. 7), and depth mode 704 (FIG. 7), are selected by selecting tissue harmonics tab 2328, gain tab 2330, and depth tab 2332, respectively. Selecting more tab 2334 accesses another set of B-mode menu items, causing them to appear on B-mode control panel 2318. Return to main mode tab 2336 returns ultrasound system 100 to the system's default imaging mode. If ultrasound system 100 is already in its default mode, no change occurs. Although in this example tissue harmonics tab 2328 is just a menu item on the B-mode control panel 2318, it could be its own display mode. Similarly, any of the menu items could have its own display mode.

FIG. 23 represents an example of the first view that is presented to the user upon powering up ultrasound system 100. Consequently, FIG. 23 is in B-mode, because users often perform significant portions of their work in B-mode. However, ultrasound system 100 could have any mode instead of B-mode control panel 2318 upon powering up, depending upon how ultrasound system 100 is configured.

In an embodiment, GUI 208 of FIG. 23 includes on screen 1914 or 2020 several elements each of which may be active and/or intelligent elements. Those elements that are active have information processing capabilities that are a function of input, context, and history, for example. Intelligent elements have interactions between elements and between the user and the elements are auto-adaptive (i.e., the intelligent elements are automatically optimized depending on a number of parameters, including system state, user habits, etc.). Some examples of context dependent user interactions are selecting a patient's name may automatically open a patient information dialog window, and selecting a measurement result may automatically open a measurements summary page. Also, selecting a battery icon may open a window with details about the battery charge status including how much time of operation is still available. Another example of a context dependent user interaction is selecting the logo of the manufacturer of ultrasound system 100 may open up a window allowing the user to connect to the manufacturer's website via the Internet through, for example, a mini web browser available on ultrasound system 100.

An embodiment of ultrasound system 100 is the combination of active and/or intelligent elements designed to facilitate one-hand and/or one-thumb controlled imaging. As an example, the tabbed panel 2306 on the top left hand side of the screen representation of FIG. 23 can be selected by using right arrow 2118 and left arrow 2122 or right and left direction buttons on keyboard 1904. The entries on one tab can be selected by using up arrow 2124 and down arrow 2120 or up and down direction buttons on keyboard 1904, for example. The icons audio tab 2322 and cursor tab 2324 on the toolbar on the bottom right hand side of the screen can be selected by navigating and selecting with right arrow 2118 and left arrow 2122 or right and left direction buttons on keyboard 1904, for example. Image area 2302 may be an active element. Changing input focus from the left hand side tab to the right hand side image element can be achieved using a combination of right arrow 2118 and left arrow 2122 or right and left direction buttons on keyboard 1904, for example.

In order to support the user in learning and operating ultrasound system 100, context sensitive help is provided. The help refers to either the ultrasound system 100's functionality or to the interpretation of image data, for example.

In another embodiment, the user interface provides for random access to any of the active elements through a touchscreen. In the one-handed operation mode, the user can utilize the thumb or any other finger to "touch" and activate any screen elements. In addition, a stylus or another pointing device can be used in a two-handed operation mode.

In order to minimize the time for setting up and configuring the system, according to this invention, the user interface provides for application and/or user dependent presets, which are optimized based on several factors (e.g., user behavior, image quality, etc.).

Figure 24:
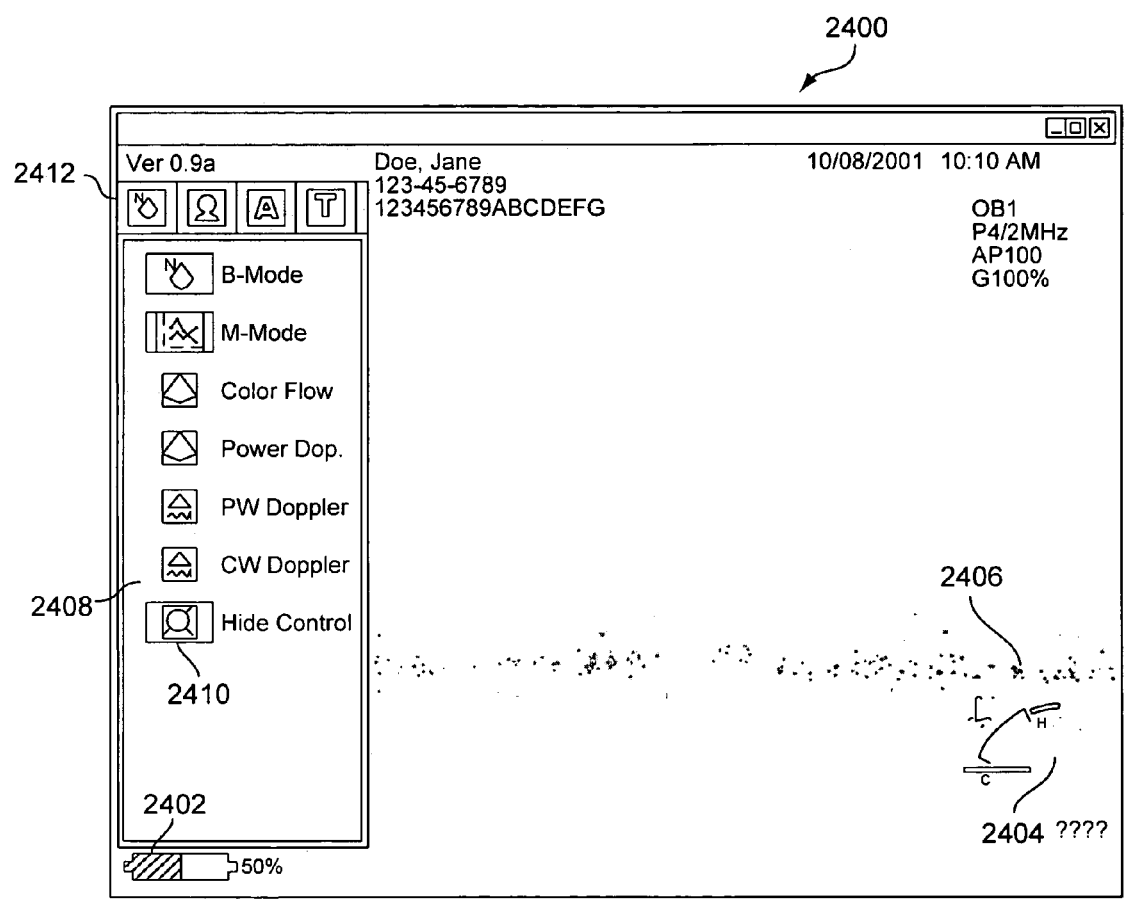
FIG. 24 shows an embodiment of the main display screen.

FIG. 24 shows an embodiment of the main display view 2400 having battery status indicator 2402, temperature gauge 2404, thermometer 2406, control panel 2408, hide control tab 2410, and tabbed panel 2412.

Battery status indicator 2402 shows how much energy or life remains in the battery. Battery status indicator 2402 is part of battery function mode 1802 (FIG. 18). When the battery change reaches a predefined threshold, the system initiates an orderly and/or controlled shutdown operation including leaving specified data in non-volatile memory. Temperature gauge 2404 and thermometer 2406 indicate the temperature of the processing unit and/or the processor system 108 (FIG. 1). One or both of temperature gauge 2404 and thermometer 2406 may be supplemented or replaced with a numerical representation of temperature, for example. Temperature gauge 2404 and thermometer 2406 are part of diagnostic mode 1806 (FIG. 18). One or both of temperature gauge 2404 and thermometer 2406 may provide the temperature of the ultrasound system 100. In this embodiment control panel 2408 has a hide control tab 2410. Hide control tab 2410 could be used to hide all or any part of control panel 2408. Hide control tab 2410 may control which menu items appear on control panel 2408. In an alternative embodiment, control panel 2408 may have an audio tab instead of or in addition to the hide control tab 2410. The audio tab may activate and/or deactivate an audio input for navigating through the menus of GUI 208 and/or for inputting data in text fields when in report mode 314, for example. Tabbed panel 2310 differs from tabbed panel 2306 only in that the icons used on the tabs are different. No cursor tab is shown because there is no image. Alternatively, a cursor tab could be displayed even when there is no image. Optionally, ultrasound system 100 may be combined with a system for taking a patients temperature, in which case temperature gauge 2404 and/or thermometer 2406 may be used for displaying the temperature of the patient. Tabbed panel 2412 and 2310 differ only in the icons used for the tabs.

Figure 25:
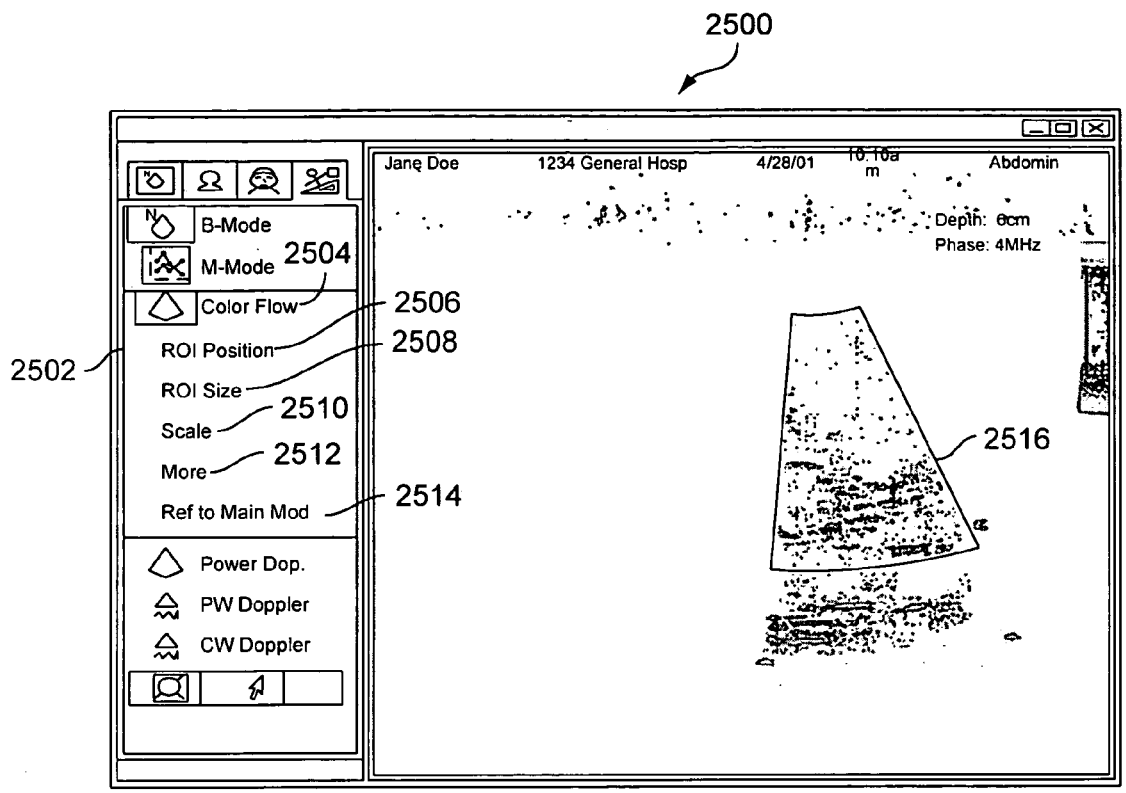
FIG. 25 shows a view having a color flow control panel.

FIG. 25 shows a view 2500 having a color flow control panel 2502, color flow tab 2504, Region Of Interest (ROI) position tab 2506, ROI size tab 2508, scale tab 2510, more tab 2512, and return to main mode 2514. View 2500 also has ROI 2516.

Color flow tab 2504 activates color flow control panel 2502. ROI position tab 2506 and ROI size tab 2508 activate ROI mode 802 (FIG. 8) and ROI size mode 808 (FIG. 8), which control position and size, respectively, of ROI 2516. Scale tab 2510 activates scale mode 806. Selecting more tab 2512 causes an additional set of color flow-mode menu items to appear, similar to more tab 2334 (FIG. 23). Return to main mode tab 2514 returns the ultrasound system 100 to the default imaging mode (e.g., B-mode 602 of main display view 2300), similar to return to main menu tab 2336 (FIG. 23).

FIG. 26A shows a view 2600 having a PW Doppler control panel 2602, PW Doppler tab 2604, gate setup tab 2606, gain tab 2608, B-mode controls tab 2610, color flow controls 2612, and more tab 2614. View 2600 also has the Doppler line 2616, ROI 2618, baseline 2620, and amplitude axis 2622, and sample volume or gate 2617 marked with a Z along the dotted line of sample volume or gate 2617.

The gate associated with view 2600 is the section along the Doppler line 2616 in which data is gathered. The section of Doppler line 2616 over which data gathered is that part of Doppler line 2616 that is within ROI 2618. The data gathered from the sample volume or gate 2617 defined by ROI 2618 and Doppler line 2616 may be plotted above baseline 2620 using amplitude axis 2622. Sample volume or gate 2617 may be an active graphic element or object. The gate position, size, and angle can be modified by selecting the appropriate menu items and changing the current menu values using the direction button 2116 and select or enter button 2114 (FIG. 21) or direction buttons and enter button on keyboard 1904. The user can position a cursor over sample volume or gate 2617 and select it using select or enter button 2114 or enter button on keyboard 1904. The size of the sample volume or gate 2617 can be modified graphically using right arrow 2118 and/or left arrow 2122 of direction button 2116 or right and/or left direction arrows of keyboard 1904, for example. The depth sample volume or gate 2617 can be modified interactively and/or graphically using down arrow 2120 and/or up arrow 2124 of direction button 2116 or up and/or down direction arrows of keyboard 1904. The angle of the sample volume can be automatically adjusted by the system to obtain the maximum intensity signal and/or sharpest image.

While PW Doppler tab 2604 is selected all color flow mode menu items and all M-mode menu items can be accessed using B-mode controls tab 2610 and color flow controls tab 2612. PW Doppler tab 2604 activates PW Doppler control panel 2602. Gate setup tab 2606 controls the size, position, and angle of the sample volume or gate 2617 for gathering data. Selecting more tab 2614 causes another set of PW Doppler mode menu items to appear, similar to more tab 2334 (FIG. 23). The return to main mode tab can be accessed by selecting more tab 2614. Alternatively, a return to main mode tab could replace any one of the other tabs of PW Doppler control panel 2602.

FIG. 26B shows a view 2650 having CW. Doppler mode 610 having a color flow image 2652 including line 2654 and ROI 2656. View 9650 also includes plots 2664 and 2666 sharing a vertical axis 2660. Plot 2664 has horizontal axis 2658, and plot 2666 has horizontal axis 2662. Control area 2665 has mode select region 2667 and panel 2668. Panel 2668 includes new patient tab 2670, application preset tab 2672, tools tab 2674, hide control and/or audio tab 2676, save tab 2678, and stop tab 2680.

The information used for plots 2664 and 2666 may be gathered from the gate defined by the portion of line 2654 subtended by ROI 2656. Plot 2664 displays spectral information using the horizontal axis 2658 for frequency and the vertical axis for amplitude. Plot 2666 is an Echo Cardio Gram (ECG) signal used to monitor heart activity and to synchronize ultrasound acquisition with heat movements.

Control area 2665 represents a different embodiment than control area 2304 (FIG. 23) having a different mixture of icons and tabs. Panel 2668 replaces tabbed panel 2306 (FIG. 23). New patient tab 2670 corresponds to new patient mode 504 (FIG. 5) and will be discussed further in connection with FIG. 27. Application preset tab 2672 corresponds to assign preset mode 404 (FIG. 4) and application presets menu items 2254 (FIG. 22). Tools tab 2674 corresponds to tools mode 320 (FIG. 3) and to tools menu items 2256 (FIG. 22). Hide control and/or audio tab 2676 corresponds to hide control tab 2410 (FIG. 24). Save tab 2678 allows the user to save the image and/or the data gathered to a file, similar to save button 2106 (FIG. 21) or a corresponding button on keyboard 1904. Stop tab 2680 may be used to stop the data acquisition and/or freeze the image similar to start/stop toggle 2102 (FIG. 21) or pause button on keyboard 1904, for example.

Figure 26C:
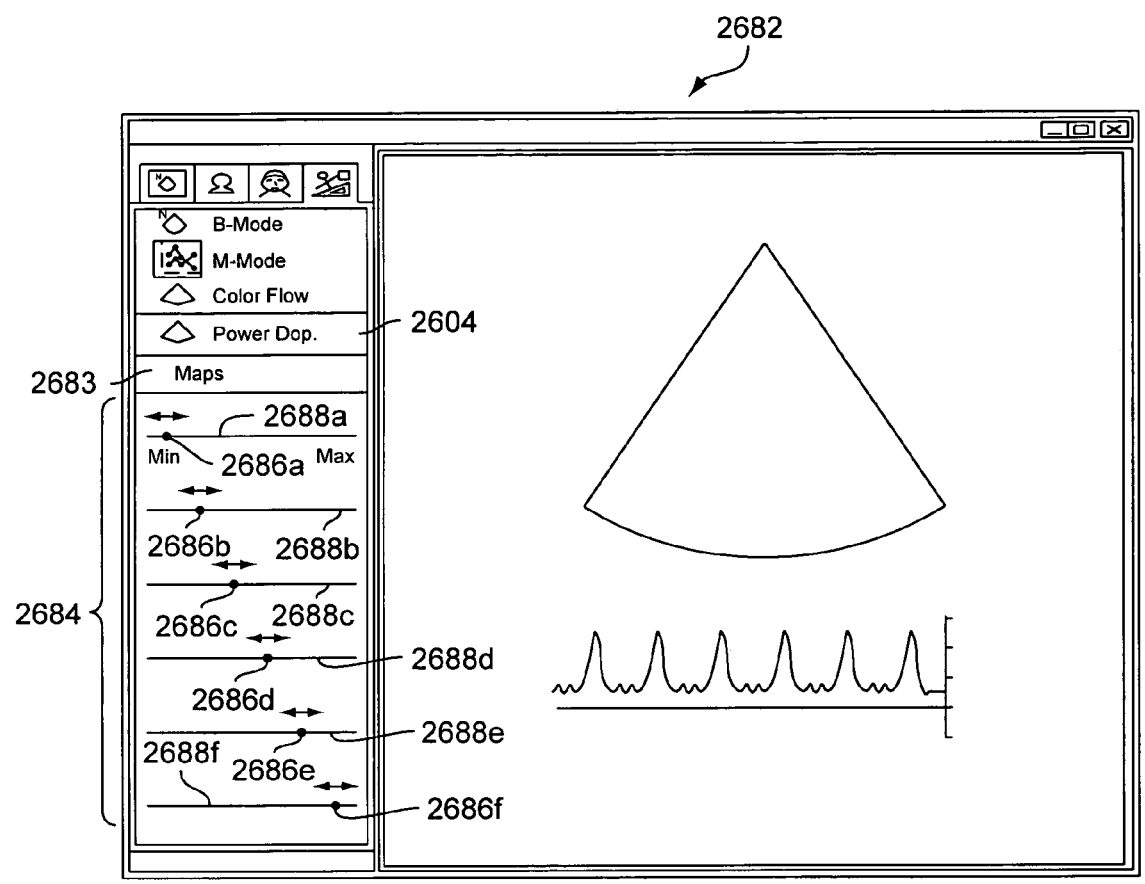
FIG. 26C shows a view having maps tab selected.

FIG. 26C shows a view 2682 having maps tab 2683 selected and power Doppler tab 2685 selected showing mapping controls 2684 which in turn has points 2686*a*–*f* and lines 2688*a*–*f*.

In an embodiment, although mapping controls 2684 of FIG. 26C cover only part of a side panel, mapping controls 2684 may be a dedicated user interface window that covers the entire screen, for example. The user can input any mapping curve through mapping controls 2684. The user can adjust the horizontal position of each of the points 2686*a*–*f* by using the left arrow 2122 and right arrow 2118 (FIG. 21) or left and right direction buttons of keyboard 1904. The user can select any of the points 2686*a*–*f* by using the up arrow 2124 and down arrow 2120 (FIG. 21) or up and down direction buttons of keyboard 1904. Alternatively, points 2686*a*–*f* can be moved by clicking and dragging using a mouse 1906 (FIG. 19), finger, and/or stylus.

Each horizontal position along lines 2688*a*–*f* corresponds to a level of magnitude between a Minimum (MIN) and Maximum (MAX) level. There can be more or less than six points 2686*a*–*f* and lines 2688*a*–*f*.

Figure 27:
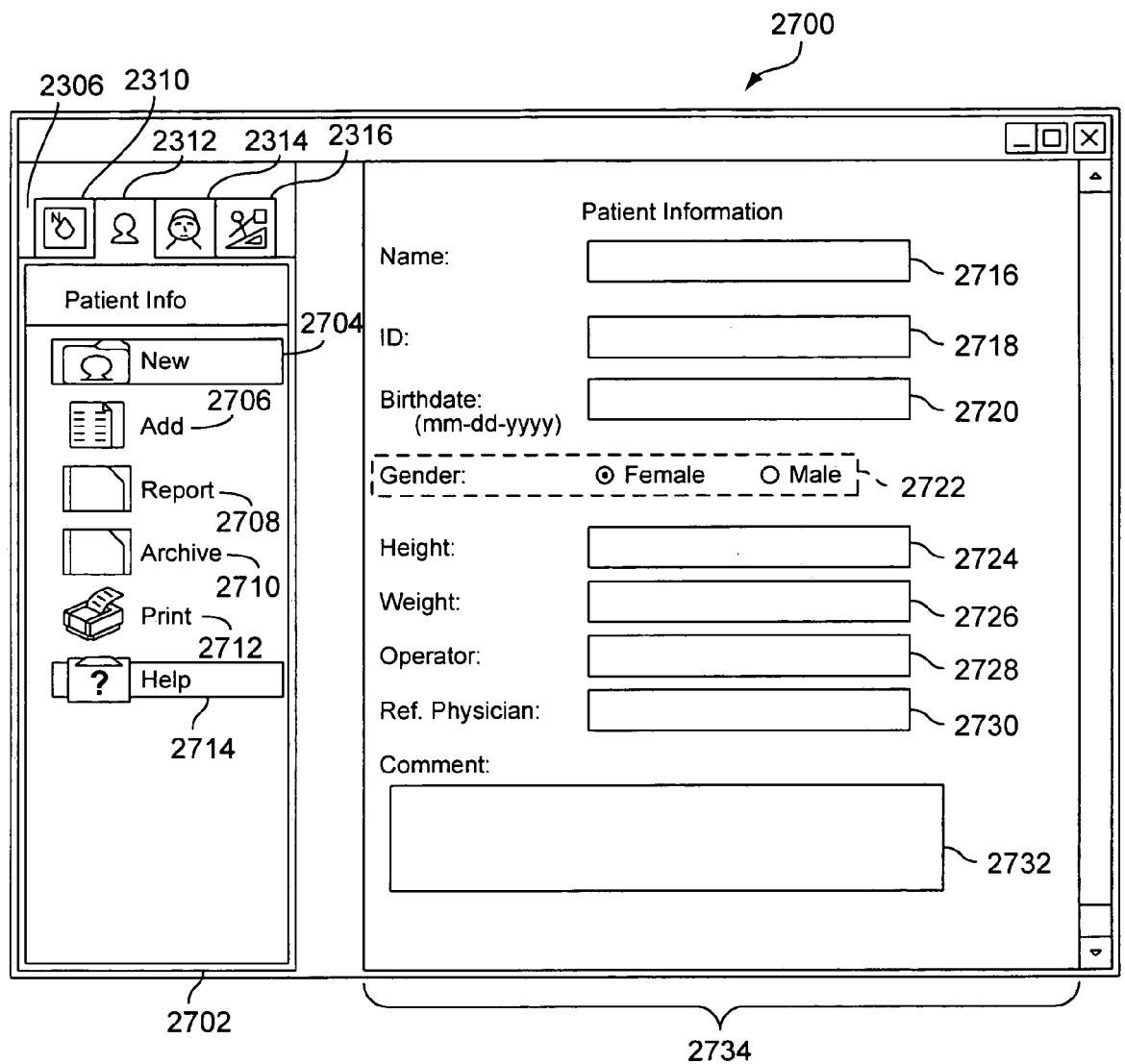
FIG. 27 is an example of a new patient view of the Graphical User Interface (GUI)

FIG. 27 is an example of a new patient view 2700 of the GUI 208 for entering information for a new patient having tabbed panel 2306 with imaging mode tab 2310, patient information tab 2312, user defined presets tab 2314, and Tools tab 2316, similar to FIG. 23. New patient view 2700 also has patient information panel 2702 and patient information area 2734. Patient information panel 2702 has new tab 2704, add tab 2706, report tab 2708, archive tab 2710, print tab 2712, and help tab 2714. Patient information area has name box 2716, ID box 2718, birthdate box 2720, gender selection 2722, height box 2724, weight box 2726, operator box 2728, referring physician box 2730, and comment box 2732.

New tab 2704 is for changing which patient's information is being displayed, designating a different patient already in the system or adding a different patient not already in the system. Add tab 2706 is for adding a new patient to the database. Report tab 2708 is for producing a report such as a medical report for an insurance company. Report tab 2708 corresponds to reporting mode 1704 (FIG. 17). Archive tab 2710 is for sending patient information to storage. Upon pressing archive tab 2710 ultrasound system 100 may decide upon a classification for the patient and an optimum location or set of locations to store the patient information. The classification for the patient may depend upon the patient's disease, place of origin, physical features, age, physician and/or location in a hospital, for example. Print tab 2712 is for printing the current view or the report and corresponds to print image/data mode 1702 (FIG. 17). Help tab 2714 is for obtaining help about any topic or may be for obtaining help about using the view being displayed. Help tab 2714 corresponds to get help mode 1804 (FIG. 18). Name box 2716, ID box 2718, birthdate box 2720, gender selection 2722, height box 2724, weight box 2726, operator box 2728, referring physician box 2730, and comment box 2732 are for entering or editing the new patient's name, identification, birthday, gender, height, weight, operator, referring physician, and comments, respectively, and are contained within patient information area 2734. The identification may be a social security number or a number assigned by the institution examining the patient. The operator may refer to the user taking or entering the data. The dotted box around gender selection 2722 is not part of the GUI 208, but was added to clarify which items are being referred to by the designation gender selection 2722. The text boxes 2716–2732 correspond to the menu items under the new patient menu item in patient utilities menu items 2252 (FIG. 22).

All the text fields of the patient information area 2734 (e.g., the name box 2716 or the "Date and Time" fields such as birthdate box 2720) may be active elements. They can be selected using the buttons, and once selected they show active and/or intelligent behavior. In an embodiment, entries can be made to any of the text boxes of patient information area 2734 using voice recognition and/or free hand writing with a stylus for example and automatic character recognition. For example, selecting the birthdate box 2720 allows the user to enter the patient's birth date using any available means such as a virtual keyboard (e.g., keyboard 2800, FIG. 28 to be discussed below), voice recognition, or free hand writing. Alternatively, given sufficient other information ultrasound system 100 will find the birth date in the database and fill in birthdate box 2720. Selecting the name box 2716 can open the database interface and retrieve the corresponding patient's records.

In an embodiment, new patient view 2700 as well as other views are configured to optimize one-hand and one-thumb operations. The patient information panel 2702 is a database interface and is configured such that database fields are selectable using the left arrow 2122, right arrow 2118, up arrow 2124 and down arrow 2120. The navigation interface with its hierarchical structure provides for up and down navigation at the same level in the hierarchy and left right navigation to move between hierarchy levels. Thus left arrow 2122 may function like a return to the previous menu, escape or back tab, and right arrow 2118 may function like a forward tab or a selection of a menu item bringing the GUI 208 to the next menu. The same multifunctional concept applies to all hierarchically structured active elements. Although not necessarily suitable for one-handed operations embodiment 1900 may be configured such that the direction buttons of keyboard 1904 have the same navigation and selection functions as arrows 2118, 2120, 2122, and 2124 described above.

Figure 28:
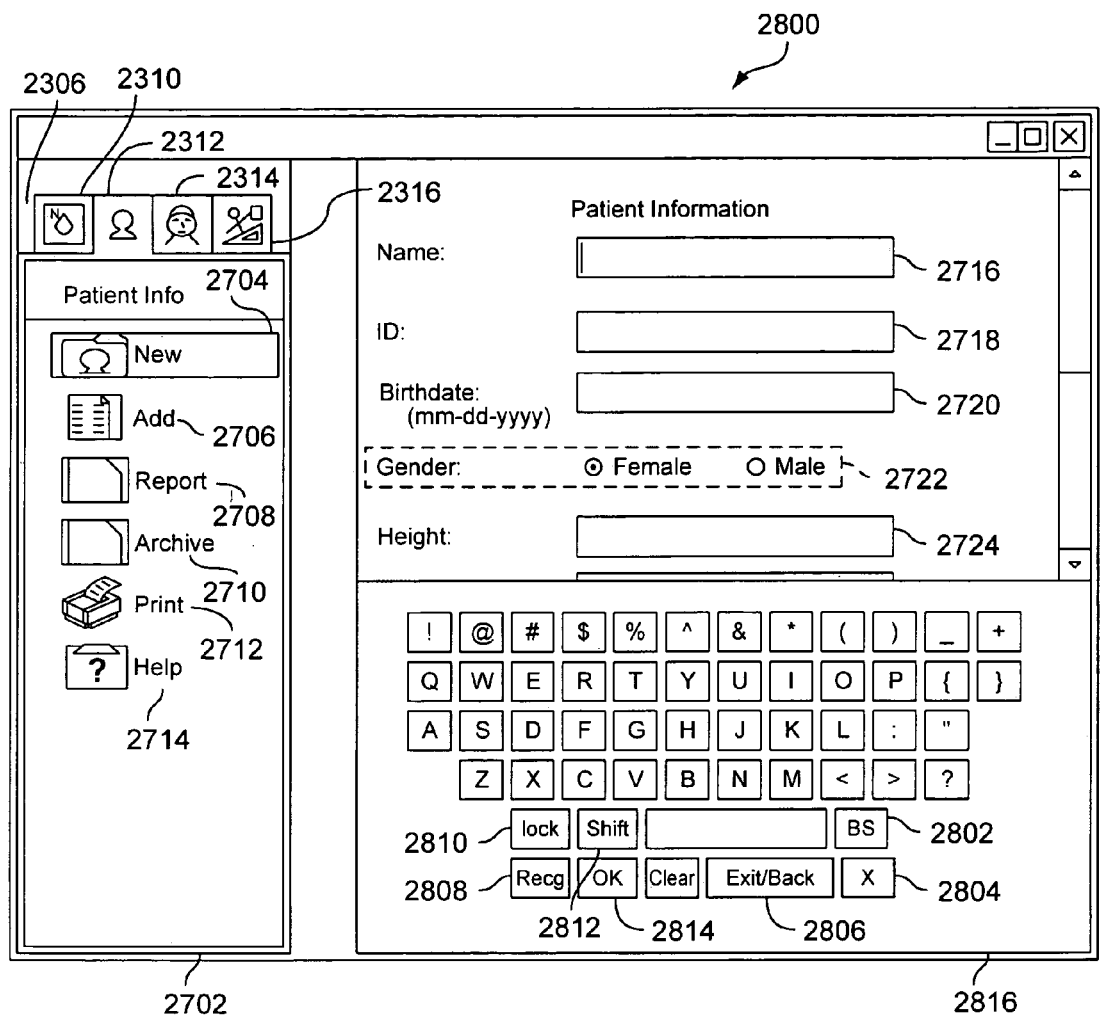
FIG. 28 is an example of the new patient view partially hidden by a virtual keyboard.

FIG. 28 is an example of the new patient view 2700 partially hidden by a virtual keyboard, keyboard 2800. The components of new patient view 2700 are the same as in FIG. 27. Keyboard 2800 has keys BS key 2802, X key 2804, exit/back key 2806, recg key 2808, lock key 2810, shift key 2812, OK key 2814 and as well as other typical keyboard keys that are not labeled, for example. Other virtual keys may be added as appropriate. For example, a new patient virtual shortcut key may be added to keyboard 2800, which may have the same function as new tab 2704 (FIG. 27). As another example, keyboard 2800 may include a key labeled search for searching a database.

BS key 2802 is a backspace key. X key 2804 is an exit key for closing 11 keyboard 2800. Exit/back key 2806 is for exiting a view or an application or for going back to the previous view or frame. Recg key 2808 is for enabling a recognitions function. Recg key 2808 may enable, for example, ultrasound system 100 to fill in remaining fields in new patient view 2700 after one or some of the boxes have already been filled in. Similarly, Recg key 2808 could enable a word match or word complete feature, which could complete partially typed or entered words with the closest match in the database. Lock key 2810 is used in combination with other keys such as shift key 2812 for a caps lock. Lock key 2810 could also be used for number lock, for example. In an embodiment, lock key 2810 can be used with recg key 2808 so that the user never needs to finish entering a word, name, or field if ultrasound system 100 can locate it first.

In an embodiment, a virtual keyboard (keyboard 2800) is provided in order to facilitate one-handed and/or potentially one-thumb alphanumeric data entry. The user can select any alphanumeric key on the keyboard by using the left arrow 2122, right arrow 2118, up arrow 2124, and/or down arrow 2120. Select or enter button 2114 may have the same effect as the enter key of the keyboard. Although not necessarily suitable for one-handed operation the direction buttons and enter button of keyboard 1904 may be used to navigate and select the keys of virtual keyboard 2800 similar to the way arrows 2118, 2120, 2122, and 2124 and enter button 2114 are used. Alternatively, pressing a key or button on keyboard 1904 may activate a corresponding key on virtual keyboard 2800.

Figure 29:
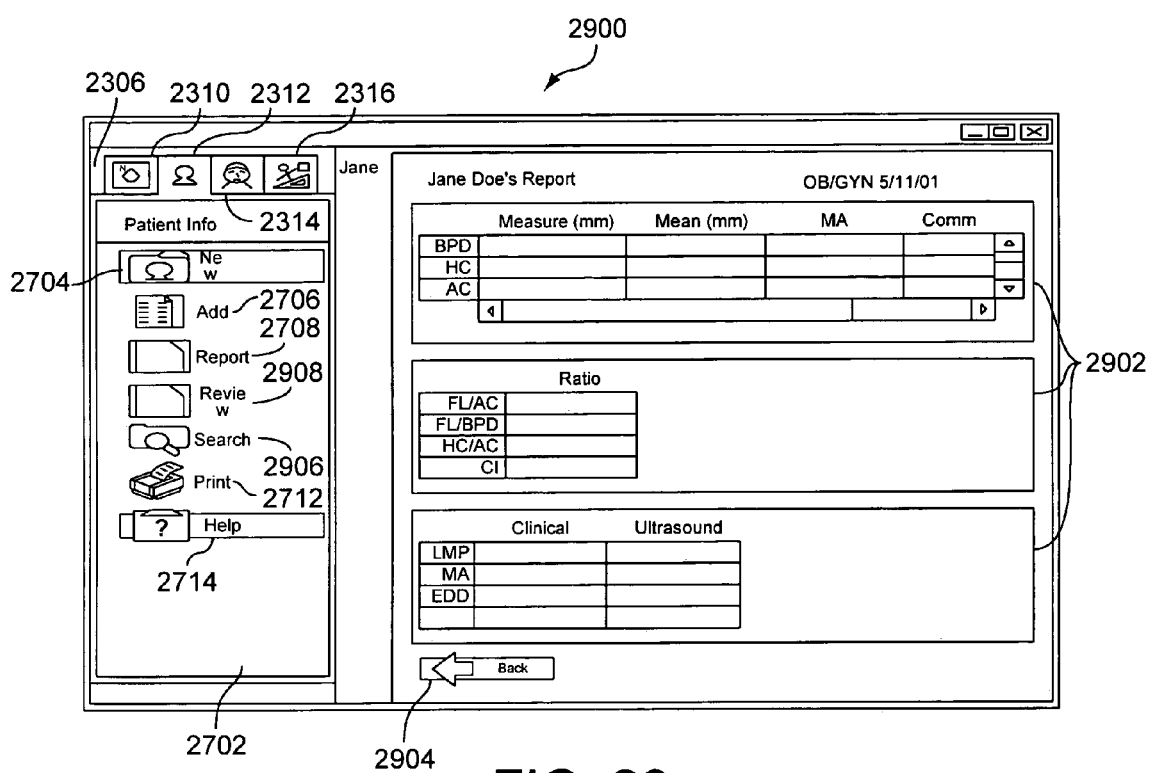
FIG. 29 is a page of a selected patient's report.

FIG. 29 is a page of a selected patient's report 2900 having patient information tables 2902 and patient information panel 2702 having back tab 2904, search tab 2906, and review tab 2908, (not present in previous FIGs.) in addition to having new tab 2704, add tab 2706, report tab 2708, print tab 2712, and help tab 2714 already described in connection with FIG. 27.

In the view of the embodiment shown in FIG. 29 patient information tables 2902 are specialized for an OB/GYN examination, but could be specialized for any type of user or customized for a particular user. Back tab 2904 brings ultrasound system 100 back to new patient view 2700. Search tab 2906 allows the user to search through ultrasound 100's database. For example, search tab 2906 may allow the user to search any one of, any combination of, or all of the record of the patient whose report is being viewed, search through the database for a specific person's report, and/or search for text in a field of all reports or a subset of reports of the database. Review tab 2908, maybe used to allow the user to review data already entered into ultrasound system 100, a related database, or an unrelated database. For example, review tab 2908 may be used to allow the report to be edited and/or the rest of the report to be reviewed.

Figure 30:
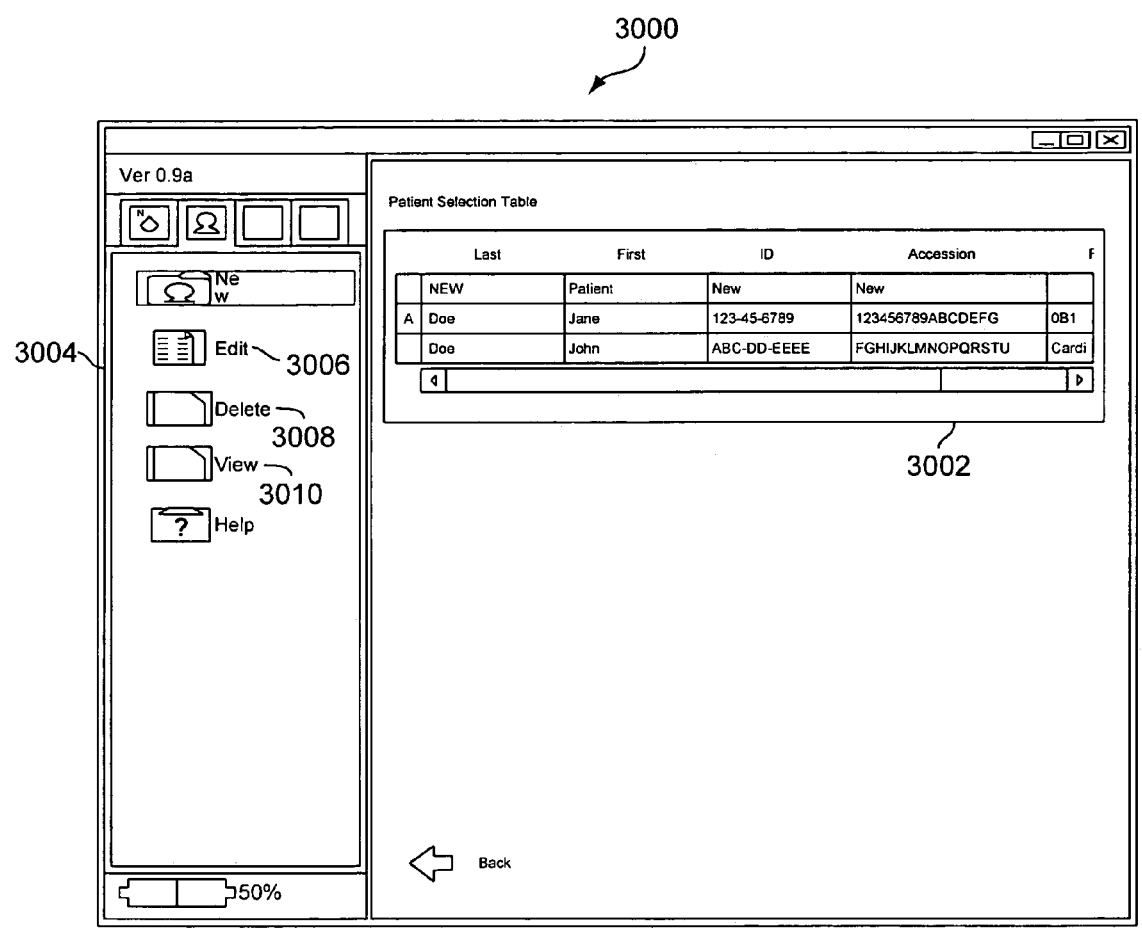
FIG. 30 shows a view for selecting a new patient.

FIG. 30 shows a view 3000 for selecting a new patient having selection table 3002, control panel 3004, edit tab 3006, delete tab 3008, and view tab 3010.

Control panel 3004 is essentially the same as sub-panel 2308 except that different icons are used. In view 3000 tabs are presented that are associated with word processing features of ultrasound system 100. Edit tab 3006 allows the user to edit a patient's records. Delete tab 3008 allows the user to delete a patient's records. View tab 3010 allows the user to view the patients in ultrasound system 100's records or another system's records. In an embodiment, selection table 3002 can be accessed by selecting review tab 29 (FIG. 29).

Figure 31A:
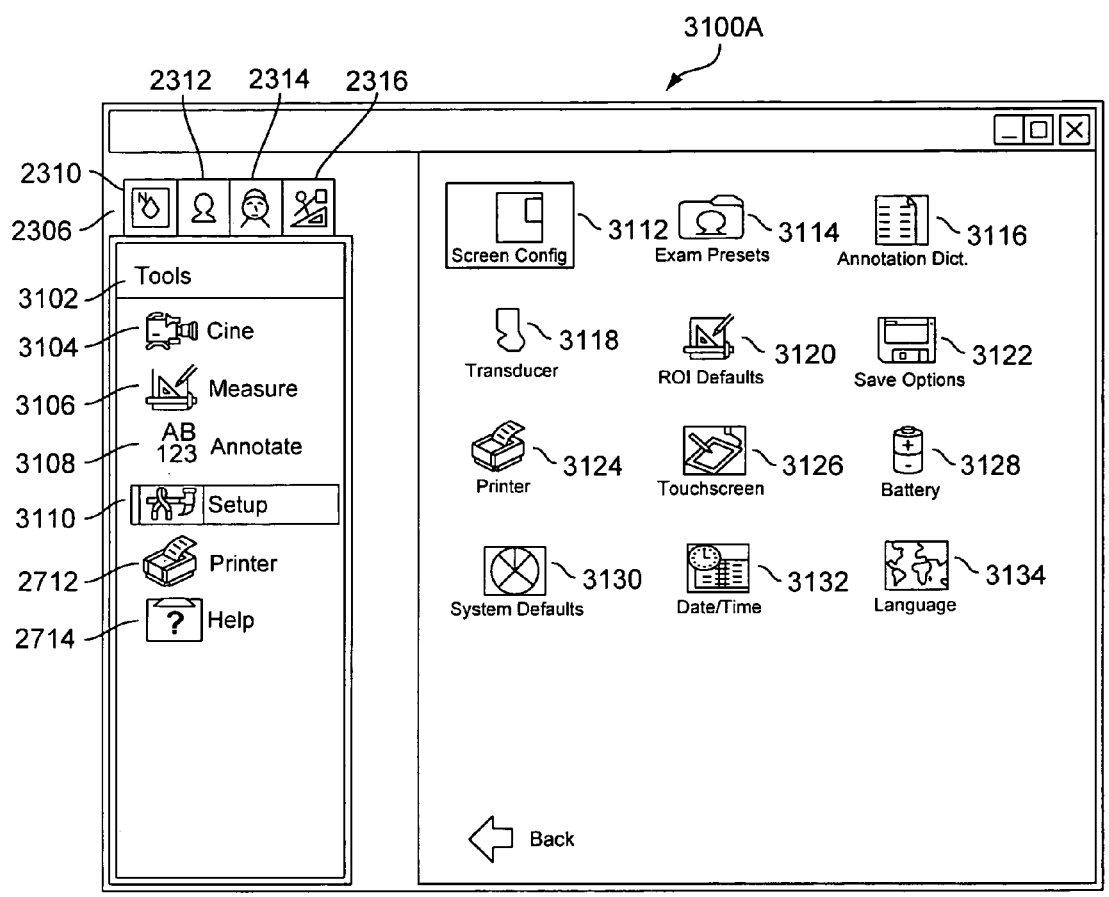
FIG. 31A shows a view of the tools panel.

FIG. 31A shows a view 3100 A of the tools panel 3102 having print tab 2712 and help tab 2714, similar to FIG. 27, and also having cine tab 3104, measure tab 3106, annotate tab 3108, setup tab 3110, screen configuration icon 3112, exam presets icon 3114, annotation dictionary icon 3116, transducer icon 3118, ROI defaults icon 3120, save options icon 3122, printer icon 3124, touchscreen icon 3126, battery icon 3128, system defaults icon 3130, date/time icon 3132, and language icon 3134.

Although not shown, additional operational icons may be included in a start up panel. For example, an export/import or upload/download icon, a reset configuration icon, an ROI defaults icon, and/or a battery icon may be included in the icons of the start up panel associated with setup tab 3110. The series of icons 3112–3134 are displayed upon selecting setup tab 3110. Screen configuration icon 3112 allows the user to configure the screen by changing its colors, locations of the control area and/or image area and/or otherwise retile the display. Screen configuration icon 3112 may also control which items appear in the start up panel. The type and position of the information displayed on the screen, e.g. menu items, measurement results, etc., can be customized and included in a preset. Icons 3112–3134 have a one-to-one correspondence with the menu items under setup in tools menu items 2256.

Figure 31B:
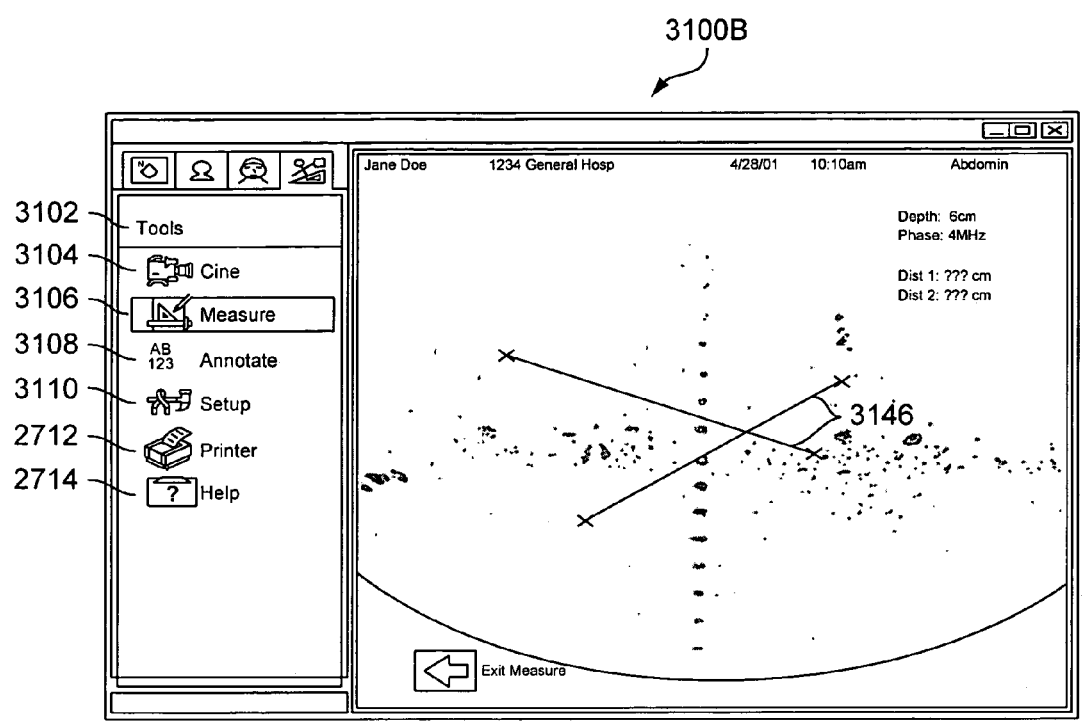
FIG. 31B shows a view having the measure menu item selected.

FIG. 31B shows a view 3100 B having measure menu item selected. Distance may be calculated along lines 3146, which were drawn by the user.

Each line 3146 is an active GUI object, and can be selected, deleted, repositioned, and resized using select or enter button 2114, up arrow 2124, down arrow 2120, left arrow 2122, right arrow 2118, and back/escape button 2104 or the direction, escape, and/or backspace buttons of keyboard 1904, for example. The each line 3146 is associated with context information; e.g., each line behaves differently if other lines are present or according to the type of calculation the user indicates she or he wants to perform. Depending on the application, for example, a ratio between the two distances may be output and automatically calculated each time one of the two lines is modified. Alternatively, the system may assist and/or instruct a user in a step by step interactive process in order to perform a sequence of measurements required by a more complicated calculation of a clinically relevant parameter.

Figure 31C:
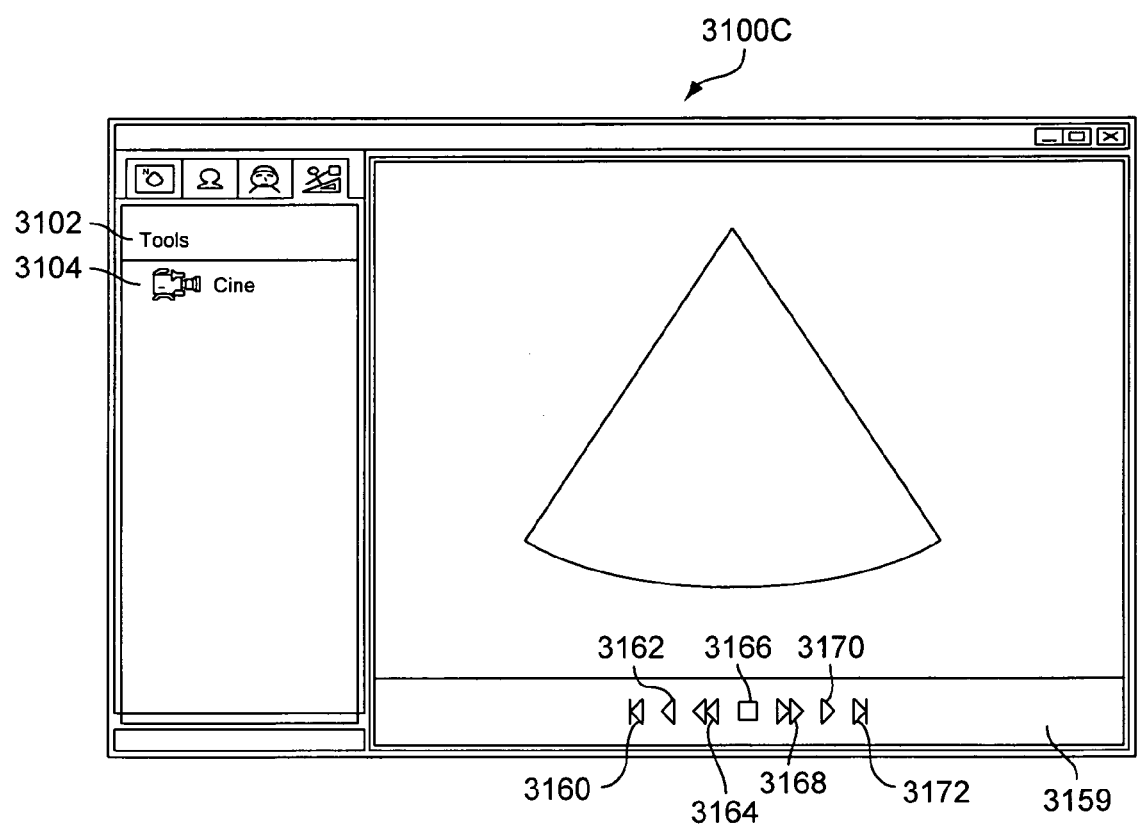
FIG. 31C shows an embodiment with video-like controls.

FIG. 31C shows an embodiment with video-like controls including tools panel 3102 having cine tab 3104 selected having video control bar 3159 including single step backward 3160, backward playback 3162, fast rewind 3164, stop 3166, fast forward 3168, forward playback 3170, single step forward 3172.

Single step backward 3160 and single step forward 3172 step one frame backward and forward, respectively. Backward playback 3162 and forward playback 3170 playback the images at a temporally realistic speed backward and forward, respectively. Fast rewind 3164 and fast forward 3168 playback the images at a fast rate backward and forward, respectively. Fast forward 3168 and fast rewind 3164 may be replaced with or may be provided in addition to a variable speed rewind or a variable speed forward, respectively. Video controls 3162–3172 may be placed under cine tab 3104 or may be placed anywhere else on the screen. Other sets of icons may be used instead of or in addition to the ones displayed in FIG. 31C. The cine control icons (e.g., video controls 3162–3172) may be selected and arranged so that they are easy navigate through and select via buttons 2016 or direction buttons and/or other buttons of keyboard 1904 and/or buttons 2016 and direction buttons and/or other buttons of keyboard 1904 may directly control how ultrasound system 100 steps through and/or plays back the frames.

Figure 32:
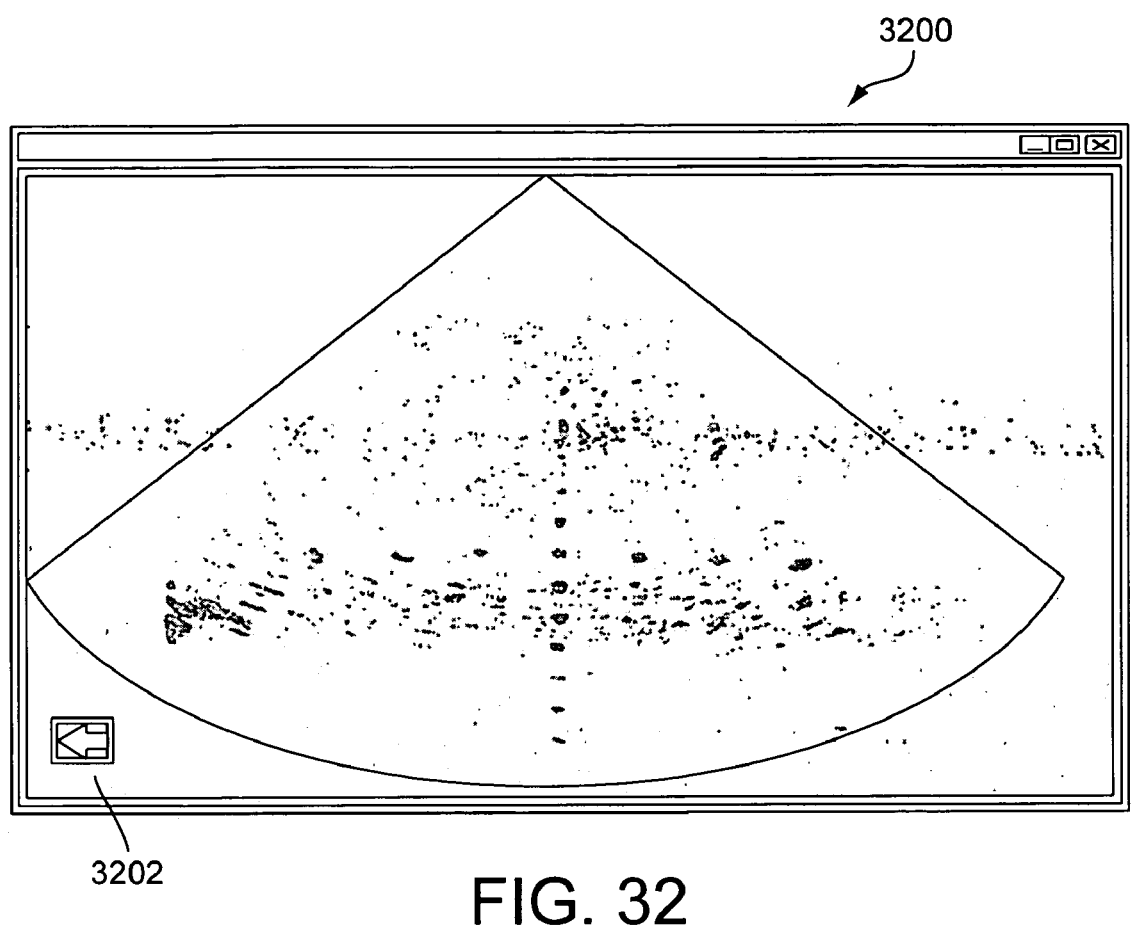
FIG. 32 shows an example of a full screen image.

FIG. 32 shows an example of a full screen image 3200 having back tab 3202, which brings back the sub-panel 2308 (FIG. 23), or 3302 (FIG. 33, below) depending upon which was the previous control panel.

In order to minimize user interactions the hide control tab 2410 of FIG. 24 allows the user to directly switch to an imaging mode, where the image occupies the full screen as in FIG. 32, using fill screen mode 618. Full screen mode 618 may show the user a bigger image, where the details are clearer than other viewing modes.

Figure 33:
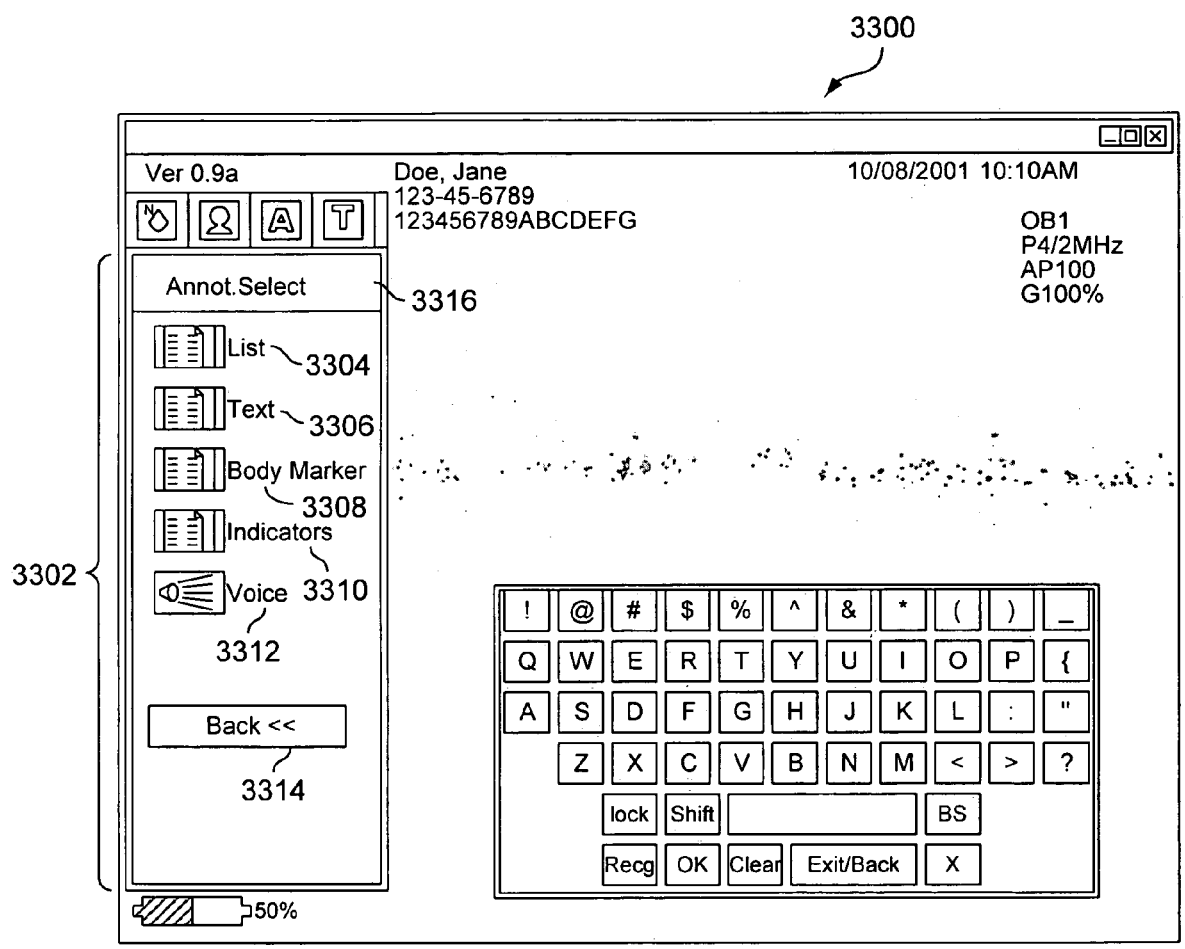
FIG. 33 shows an example of a view including an annotation control panel.

FIG. 33 shows an example of a view 3300 including an annotation control panel 3302 having annotate select tab 3316 selected showing a list tab 3304, text tab 3306, body markers tab 3308, indicators tab 3310, voice tab 3312, and back tab 3314.

List tab 3304 may bring the ultrasound system 100 to a list of user options, for example, which may include a list of predefined annotations. An item in the list can be selected by using up arrow 2124, down arrow 2120, left arrow 2122, right arrow 2118, select or enter button 2114, direction and enter buttons of keyboard 1904, a stylus, and/or speaking the item into the microphone, for example. The system may recognize words and automatically select the appropriate item. Alternatively, the system may present the item to the user in alphabetical order or labeled with letter and/or numbers. The user may then pronounce one or more letters and/or numbers, and ultrasound systems 100 automatically searches the list for all annotations starting with that letter, number, or sequence of letters and/or numbers. Ultrasound system 100 then presents the items found to the user in alphabetical and/or numerical order. Text tab 3306 allows the user to enter text onto the image by using either keyboard 1904, virtual keyboard 2800, voice input, and/or the free hand character recognition. In an embodiment, the text can be moved anywhere on the image by dragging and dropping. Body markers tab 3308 gives the user a list of icons representing various body parts that can be placed on the image. Indicators tab 3310 is used to indicate the diagnosis of the patient. Voice tab 3312 is used to attach a voice message to the image. Back tab 3314 brings the ultrasound system 100 back to the previous view.

Figure 34:
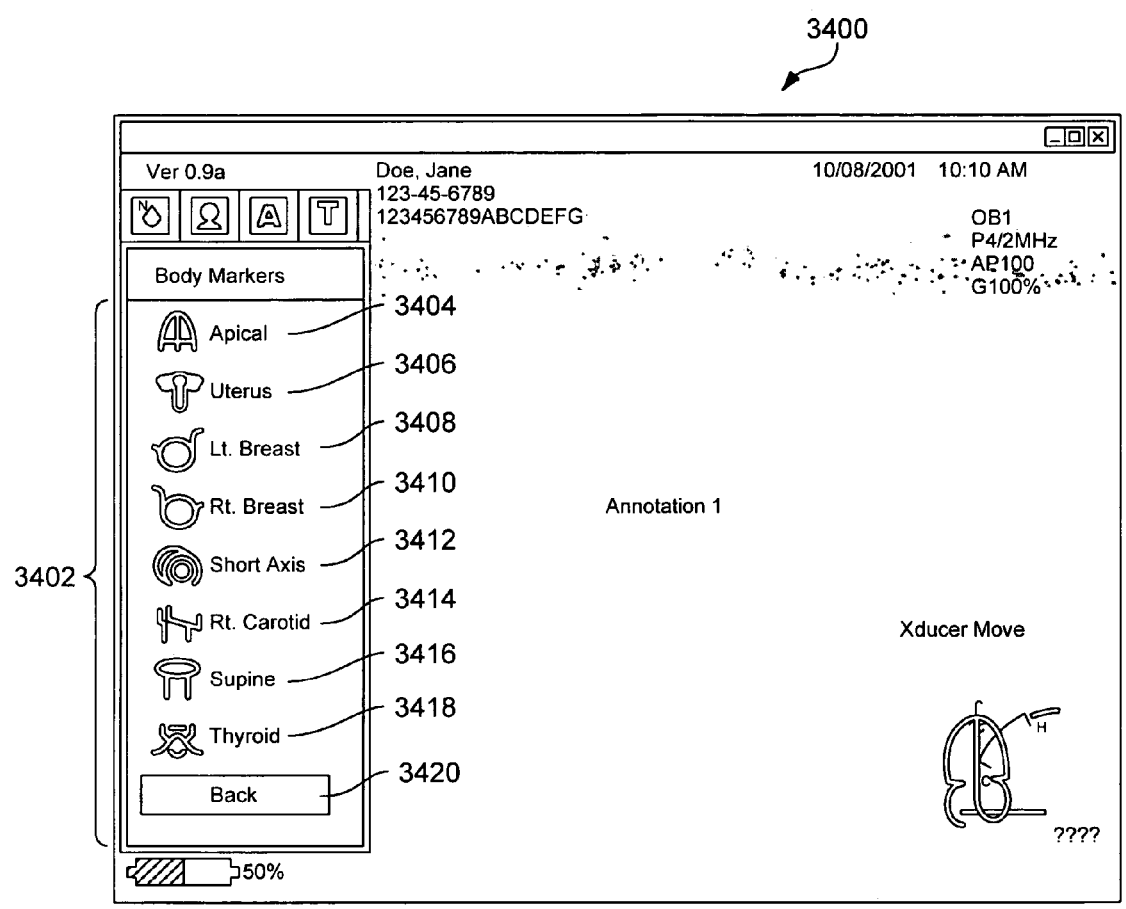
FIG. 34 shows an example of a view including an annotation list for an OB/GYN.

FIG. 34 shows an example of a view 3400 including an annotation list 3402. As an example, annotation list 3402 of FIG. 34 is a list of body markers for an OB/GYN, but could be focused differently for another user and/or is just one view of several, each for a different type of examination, measurement, and/or user. Annotation list 3402 includes an apical 4 marker 3404, uterus marker 3406, left breast body marker 3408, right breast body marker 3410, short axis marker 3412, right carotid marker 3414, supine marker 3416, and thyroid marker 3418, for example. View 3400 also has a back tab 3420.

Annotation list 3402 can be used to select a body part marker, for example thyroid marker 3418, which appears on the image. The body part marker can be moved by dragging and dropping using a cursor arrow, for example. Back tab 3420 brings the ultrasound system 100 back to the previous view. Body markers can be static and/or, animated graphical objects. For example, an animated body marker can be used to represent more clearly what is the relative portion of the body being imaged by the ultrasound transducer.

Figure 35:
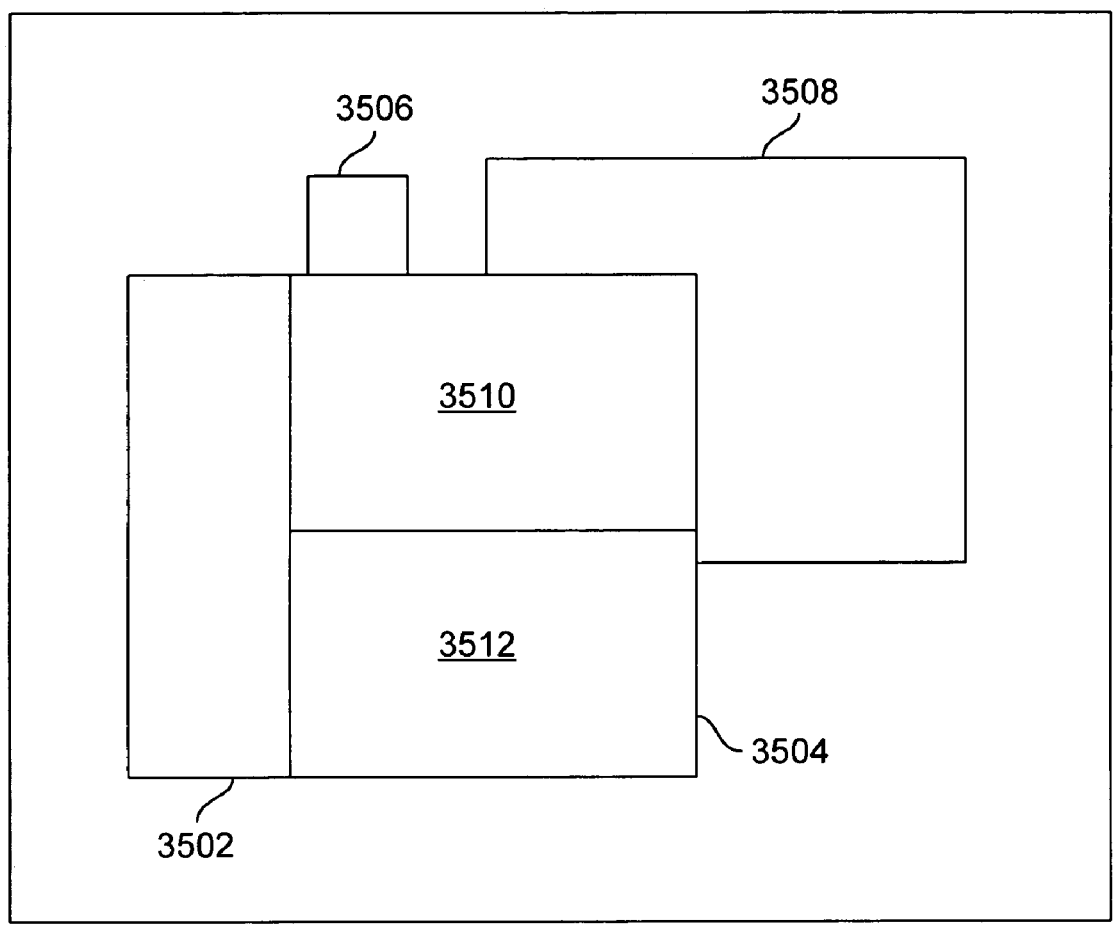
FIG. 35 shows a view of a handheld ultrasound system having a windows based operating system.

FIG. 35 shows a view 3500 of a handheld ultrasound system having a windows based GUI having control area #1 3502, image area #1 3504, control area #2 3506, and image area #2 3508. Control area #1 3502 and image area #1 3504 are attached to one another, while control area #2 3506 and image area #2 3508 are detached. In this embodiment the user can attach and detach the image areas and control panels and retile the screen as desired. Image area #1 3504 may contain a B-mode type image, while image area #2 3508 may contain a patient information view similar to view 2734. Additionally, image area #1 3504 or any other image area may be divided into a data area 3510 containing data such as patient information and a picture area 3512 containing ultrasound images and/or plots. The screen can be tiled to view two image areas simultaneously, for example. The windows can be moved by dragging and dropping them with a cursor.

Although many of the embodiments of the GUI 208 and of the operation of ultrasound system 100 were described in conjunction with the embodiment of FIGS. 20 and 21, the embodiment of FIG. 19 can also be used for the same embodiments described in conjunction with FIGS. 20 and 21.

Although each of the modes 602–618 of image mode selection mode 308 is depicted as containing a different set of modes, any mode of contained within any of modes 608 could be used within any of the other of modes 602–618.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

What is claimed is:

1. A handheld user interface for an ultrasonic imaging system, the user interface comprising:
    a set of display and user interaction areas comprising:
        an image area configured to display ultrasonic images;
        a control area comprising elements configured to enable a user to access a plurality of operation modes single-handedly, the elements having active behavior that provides timely user control of the ultrasonic imaging system whereby each of the display areas can interact with the user independently in order to provide timely response to specific user requests; and
    means for causing the user interface to automatically optimize display settings in accordance with a plurality of parameters.

2. The user interface of claim 1, wherein the image area is further configured to display patient information fields.

3. The user interface of claim 1, wherein the image area is further configured to display patient information retrieved from a patient information database using active database components.

4. The user interface of claim 1, wherein the image area is further configured to display system configuration information using active display elements.

5. The user interface of claim 1, wherein the active behavior of the elements comprises behavior based on context.

6. The user interface of claim 1, wherein the active behavior of the elements comprises behavior based on a history of user interactions with the ultrasonic imaging system.

7. The user interface of claim 1, wherein the active behavior of the elements comprises behavior based on a state of the ultrasonic imaging system.

8. The user interface of claim 1, wherein the elements are configured to accept input comprising voice commands.

9. The user interface of claim 1, further comprising a virtual keyboard configured to allow the user to interact with the elements.

10. The user interface of claim 9, wherein the virtual keyboard comprises user programmable function keys.

11. The user interface of claim 9, wherein the virtual keyboard is configured to accept input comprising voice commands.

12. The user interface of claim 9, wherein the virtual keyboard is configured to accept input via a touchscreen.

13. The user interface of claim 1, wherein the plurality of operation modes comprises a patient information mode, an image mode selection mode, an image acquisition mode, and a system configuration mode.

14. The user interface of claim 1, wherein the plurality of operation modes comprises an archive mode configured to enable patient information to be saved to a patient information database.

15. The user interface of claim 1, wherein the plurality of operation modes comprises an annotation mode configured to enable the user to attach annotations to a stored ultrasonic image.

16. The user interface of claim 15, wherein the annotation mode enables the user to attach a text annotation to the stored ultrasonic image.

17. The user interface of claim 15, wherein the annotation mode enables the user to attach a voice annotation to the stored ultrasonic image.

18. The user interface of claim 1, wherein the ultrasonic imaging system is portable.

19. The user interface of claim 1, wherein the control area comprises at least one tab selectable by the user to select one of the plurality of operation modes.

20. The user interface of claim 1, wherein the control area comprises a tab selectable by the user to expand the image area to a full screen view.

21. A handheld user interface for an ultrasonic imaging system, the user interface comprising:
 a set of display and user interaction areas comprising:
  an image area configured to display ultrasonic images;
  a control area comprising elements configured to enable a user to access a plurality of operation modes single-handedly, the elements having intelligent behavior that provides optimized user control of the ultrasonic imaging system whereby each of the display areas can interact with the user independently in order to provide timely response to specific user requests; and
 means for causing the user interface to automatically optimize display settings in accordance with a plurality of parameters.

22. The user interface of claim 21, wherein the image area is further configured to display patient information fields.

23. The user interface of claim 21, wherein the image area is further configured to display patient information retrieved from a patient information database.

24. The user interface of claim 21, wherein the image area is further configured to display system configuration information.

25. The user interface of claim 21, wherein the intelligent behavior of the elements comprises auto-adaptive behavior.

26. The user interface of claim 21, wherein the intelligent behavior of the elements comprise behavior based on context.

27. The user interface of claim 21, wherein the intelligent behavior of the elements comprises behavior based on a history of user interactions with the ultrasonic imaging system.

28. The user interface of claim 21, wherein the intelligent behavior of the elements comprises behavior based on a state of the ultrasonic imaging system.

29. The user interface of claim 21, wherein the elements are configured to accept input comprising voice commands.

30. The user interface of claim 21, further comprising a virtual keyboard configured to allow the user to interact with the elements.

31. The user interface of claim 30, wherein the virtual keyboard comprises user programmable function keys.

32. The user interface of claim 30, wherein the virtual keyboard is configured to accept input comprising voice commands.

33. The user interface of claim 30, wherein the virtual keyboard is configured to accept input via a touchscreen.

34. The user interface of claim 21, wherein the plurality of operation modes comprises a patient information mode, an image mode selection mode, an image acquisition mode, and a system configuration mode.

35. The user interface of claim 21, wherein the plurality of operation modes comprises an archive mode configured to enable patient information to be saved to a patient information database.

36. The user interface of claim 21, wherein the plurality of operation modes comprises an annotation mode configured to enable the user to attach annotations to a stored ultrasonic image.

37. The user interface of claim 36, wherein the annotation mode enables the user to attach a text annotation to the stored ultrasonic image.

38. The user interface of claim 36, wherein the annotation mode enables the user to attach a voice annotation to the stored ultrasonic image.

39. The user interface of claim 21, wherein the ultrasonic imaging system is portable.

40. The user interface of claim 21, wherein the control area comprises at least one tab selectable by the user to select one of the plurality of operation modes.

41. The user interface of claim 21, wherein the control area comprises a tab selectable by the user to expand the image area to a full screen view.

42. A handheld user interface for an ultrasonic imaging system, the user interface comprising:

a plurality of display areas, at least one of the plurality of display areas comprising at least one independent element configured to be operated single-handedly, the at least one independent element operable to receive user input and maintain a history of user interaction, and the at least one independent element having behavior that depends upon input and the history of user interaction; and means for causing the user interface to automatically optimize display settings in accordance with a plurality of parameters.

43. The user interface of claim 42, wherein each of the plurality of display areas is resizable by a user.

44. The user interface of claim 42, wherein each of the plurality of display areas is repositionable by a user.

45. The user interface of claim 42, wherein at least one of the plurality of display areas is configured to display ultrasonic image data.

46. The user interface of claim 42, wherein at least one of the plurality of display areas is configured to display system information.

47. A handheld user interface comprising:
a plurality of operation modes comprising an image acquisition mode, a system configuration mode, a measure and annotate mode, an archiving mode, and a system services mode;
a display view shown on a display device, the display view comprising an image area and a control area, the image area configured to display an image generated in accordance with the image acquisition mode, and the control area configured to enable selection of one of the plurality of operation modes single-handedly; and
means for causing the user interface to automatically optimize display settings in accordance with a plurality of parameters.

48. The user interface of claim 47, wherein the display view comprises a plurality of windows, each of the windows being resizable and repositionable within the display view.

49. The user interface of claim 48, wherein the control area is configured to enable a user to hide all windows in the display view except for the image area, which then automatically expands to occupy the entire display view.

50. The user interface of claim 47, wherein the control area comprises at least one tab selectable by a user to select one of the plurality of operation modes.

51. The user interface of claim 50, wherein the control area comprises at least one tab selectable by the user to select at least one mode within a selected operation mode.

52. The user interface of claim 47, wherein the control area comprises a virtual keyboard.

53. A handheld user interface comprising:
an image view configured to display an ultrasound image;
a control view configured to present controls to a user, the controls configured to be operated single-handedly, the control view comprising active elements, each active element having context-dependent behavior, and each active element configured to maintain a history of user interactions with that active element; the control view further comprising intelligent elements, each intelligent element configured to provide auto-adaptive interactions between the user and the user interface; and
means for causing the user interface to automatically optimize display settings in accordance with a plurality of parameters.

* * * * *